(12) United States Patent
Jorcyk et al.

(10) Patent No.: US 11,633,457 B2
(45) Date of Patent: Apr. 25, 2023

(54) PHARMACEUTICAL COMPOSITIONS COMPRISING ONCOSTATIN M (OSM) ANTAGONIST DERIVATIVES AND METHODS OF USE

(71) Applicant: Boise State University, Boise, ID (US)

(72) Inventors: Cheryl Jorcyk, Boise, ID (US); Don Warner, Boise, ID (US); Matthew David King, Boise, ID (US); Lisa Warner, Boise, ID (US)

(73) Assignee: Boise State University, Boise, ID (US)

( * ) Notice: Subject to any disclaimer, the term of this patent is extended or adjusted under 35 U.S.C. 154(b) by 306 days.

(21) Appl. No.: 16/846,073

(22) Filed: Apr. 10, 2020

(65) Prior Publication Data

US 2020/0323960 A1    Oct. 15, 2020

Related U.S. Application Data

(60) Provisional application No. 62/832,384, filed on Apr. 11, 2019.

(51) Int. Cl.
*A61P 35/00* (2006.01)
*A61K 45/06* (2006.01)
*A61K 38/20* (2006.01)

(52) U.S. Cl.
CPC .......... *A61K 38/204* (2013.01); *A61K 45/06* (2013.01); *A61P 35/00* (2018.01)

(58) Field of Classification Search
CPC .. C07D 215/00; C07D 239/72; C07D 277/00; C07D 307/00; C07D 277/02; C07D 307/02; A61K 31/34; A61K 31/47; A61K 31/426; A61K 31/517; A61P 35/00
See application file for complete search history.

(56) References Cited

U.S. PATENT DOCUMENTS

| | | | |
|---|---|---|---|
| 5,925,740 A | 7/1999 | Mosley et al. | |
| 6,074,643 A | 6/2000 | Barbera-Guillem | |
| 6,706,266 B1 | 3/2004 | Life | |
| 7,291,332 B2 | 11/2007 | Life | |
| 7,572,896 B2 | 8/2009 | Mather et al. | |
| 7,858,753 B2 | 12/2010 | Ellis et al. | |
| 7,947,653 B1 | 5/2011 | Sordella et al. | |
| 8,003,101 B2 | 8/2011 | Life et al. | |
| 8,216,578 B2 | 7/2012 | Mather et al. | |
| 8,470,316 B2 | 6/2013 | Yasunami | |
| 9,550,828 B2 * | 1/2017 | Jorcyk | A61K 45/06 |
| 10,286,070 B2 * | 5/2019 | Jorcyk | A61K 31/4184 |
| 2006/0171951 A1 | 8/2006 | Mather et al. | |
| 2006/0276440 A1 | 12/2006 | An et al. | |
| 2007/0286861 A1 | 12/2007 | Ellis et al. | |
| 2010/0113297 A1 | 5/2010 | Lidereau et al. | |
| 2010/0189721 A1 | 7/2010 | Brisbane et al. | |
| 2011/0245470 A1 | 10/2011 | Ellis et al. | |
| 2012/0093833 A1 | 4/2012 | Almagro et al. | |
| 2012/0121579 A1 | 5/2012 | Braun et al. | |
| 2012/0121594 A1 | 5/2012 | Smith | |
| 2012/0128626 A1 | 5/2012 | Smith | |
| 2012/0183539 A1 | 7/2012 | Maeda | |
| 2012/0189629 A1 | 7/2012 | Smith | |
| 2012/0294852 A1 | 11/2012 | Smith | |
| 2013/0028860 A1 | 1/2013 | Smith et al. | |
| 2013/0251724 A1 | 9/2013 | Bembridge et al. | |
| 2014/0099315 A1 | 4/2014 | Almagro et al. | |
| 2015/0093391 A1 * | 4/2015 | Jorcyk | A61K 31/4184 514/263.21 |

FOREIGN PATENT DOCUMENTS

| | | |
|---|---|---|
| CN | 103127503 A | 6/2013 |
| EP | 1849478 A2 | 10/2007 |
| WO | 0136472 A2 | 5/2001 |
| WO | 2006074192 A2 | 7/2006 |
| WO | 2010139742 A1 | 12/2010 |
| WO | 2012069433 A2 | 5/2012 |
| WO | 2013019690 A1 | 2/2013 |

OTHER PUBLICATIONS

Whitehouse (Biochemical Pharmacology vol. 16 pp. 753-760. Published 1967). (Year: 1967).*
Bolin et al., "Oncostatin M Promotes Mammary Tumor Metastasis to Bone and Osteolytic Bone Degradation", Genes & Cancer 3(2), 117-130. Sep. 6, 2012.
Jorcyk et al., "Oncostatin M induces cell detachment and enhances the metastatic capacity of T-47D human breast carcinoma cells", Cytokine, vol. 33, pp. 323-336, 2006.
Migita et al., "CP690,550 inhibits oncostatin M-induced JAK/STAT signaling pathway in rheumatoid synoviocytes", Arthritis Research & Therapy, pp. 1-10. 2011.
Nawa et al., "Discovering small molecules that inhibit adipogenesis and promote osteoblastogenesis: Unique screening and Oncostatin M-like activity", Differentiation 86, 65-74. Aug. 30, 2013.
Nishimoto et al., "Oncostatin M, Leukemia inhibitory factor, and interleukin 6 induce the proliferation of human plasmacytoma cells via the common signal transducer, GP130", J. Exp. Med., vol. 179, pp. 1343-1347, Apr. 1994.

(Continued)

*Primary Examiner* — Theodore R. Howell
*Assistant Examiner* — George W Kosturko
(74) *Attorney, Agent, or Firm* — McKee, Voorhees & Sease, PLC

(57) ABSTRACT

A method of treating cancer or metastasis is provided involving administering at least one oncostatin M (OSM) antagonist to a subject, wherein the subject has been diagnosed with cancer. Administration of an OSM antagonist such as a small molecule pharmaceutical is provided as well as an anti-OSM antibody, an anti-OSM aptamer, and an OSM mRNA antagonist. The OSM antagonists were found to inhibit or prevent tumor cell detachment, progression, proliferation and metastasis in several cancer types.

31 Claims, 9 Drawing Sheets

Specification includes a Sequence Listing.

(56) References Cited

OTHER PUBLICATIONS

Queen et al., "Breast cancer cells stimulate neutrophils to produce Oncostatin M: potential implications for tumor progression", Cancer Res., vol. 65(19), pp. 8896-8904, Oct. 1, 2005.
Rhodes et al., "The generation and characterization of antagonist RNA aptamers to human Oncostatin M", Journal of Biological Chemistry, vol. 275, No. 37, pp. 28555-28561, Sep. 15, 2000.
Stead et al, "Discovery of novel ansamycins possessing potent inhibitory activity in a cell-based Oncostatin M signalling assay", The Journal of Antibiotics, vol. 53, No. 7, pp. 657-663, Jul. 7, 2000.
Weiss et al., "Oncostatin M and IL-6 Induce u-PA and VEGF in prostate cancer cells and correlate in vivo", Anticancer Research, vol. 31, pp. 3273-3278, 2011.

* cited by examiner

PHARMACEUTICAL COMPOSITIONS COMPRISING ONCOSTATIN M (OSM) ANTAGONIST DERIVATIVES AND METHODS OF USE

CROSS-REFERENCE TO RELATED APPLICATIONS

This application claims priority under 35 U.S.C. § 119 to provisional application Ser. No. 62/832,384, filed Apr. 11, 2019, herein incorporated by reference in its entirety.

REFERENCE TO GOVERNMENT SUPPORT

This invention was made with government support under Grant No. GM103408 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on May 18, 2020, is named P12887US01_SEQLISTING_05-18-20_ST25.txt and is 5,222 bytes in size.

FIELD OF THE INVENTION

The present disclosure generally relates to treatment of cancer, and, more specifically, to the inhibition of signaling molecules implicated in the invasion and metastasis of cancer cells.

BACKGROUND OF THE INVENTION

Metastasis or metastatic disease is the spread of a disease from one organ or part to another non-adjacent organ or part. Metastatic disease is primarily but not uniquely associated with malignant tumor cells and infections relating to cancer. (Klein, 2008, Science 321(5897):1785-88; Chiang & Massague, 2008, New Engl. J. Med. 359(26):2814-23).

Cancer occurs after a single cell in a tissue is genetically damaged in ways that result in the formation of a putative cancer stem cell possessing a malignant phenotype. These cancer stem cells are able to undergo uncontrolled abnormal mitosis, which serves to increase the total number of cancer cells at that location. When the area of cancer cells at the originating site become clinically detectable, it is called primary tumor. Some cancer cells also acquire the ability to penetrate and infiltrate surrounding normal tissues in the local area, forming a new tumor. The newly formed tumor in the adjacent site within the tissue is called a local metastasis.

Some cancer cells acquire the ability to penetrate the walls of lymphatic and/or blood vessels, after which they are able to circulate through the bloodstream (circulating tumor cells) to other sites and tissues in the body. This process is known (respectively) as lymphatic or hematogenous spread. After the tumor cells come to rest at another site, they re-penetrate through the vessel or walls (extravasation), continue to multiply, and eventually another clinically detectable tumor is formed. This new tumor is known as a metastatic (or secondary) tumor. Metastasis is one of the hallmarks of malignancy. Most tumors and other neoplasms can metastasize, although in varying degrees (e.g. basal cell carcinoma rarely metastasizes) (Kumar et al., 2005, "Robbins and Cotran Pathologic Basis of Disease", 7th ed., Philadelphia: Elsevier Saunders).

Metastatic tumors are very common in the late stages of cancer. The most common places for the metastases to occur are the lungs, liver, brain, and the bones. There is also a propensity for a tumor to seed in particular organs. For example, prostate cancer usually metastasizes to the bones. In a similar manner, colon cancer has a tendency to metastasize to the liver. Stomach cancer often metastasizes to the ovaries in women. Breast tumor cells often metastasize to bone tissue. Studies have suggested that these tissue-selective metastasis processes are due to specific anatomic and mechanical routes.

Oncostatin M (OSM) is a 28 kDa multifunctional member of the IL-6 family of cytokines secreted by monocytes, macrophages, neutrophils and activated T-lymphocytes (Tanaka & Miyajima, Rev Physiol Biochem Pharmacol 149: 39-53, 2003). Proteolytic cleavage near the carboxy-terminus of the secreted OSM yields the fully active form of OSM, 209 amino acids length having two N-linked glycosylation sites. OSM belongs to the IL-6 family of cytokines that includes (IL-6, IL-11, leukemia inhibitory factor (LIF), cardiotrophin-1, ciliary neutotrophic factor (CNTF) and cardiotrophin-like cytokine (CLC)) which share a common receptor subunit, gp130 protein. In humans, OSM signals through receptor heterodimers consisting of gp130 and the LIFRα subunit or gp130 and the OSMRβ subunit. In contrast to the other cytokines of the IL-6 family, OSM binds gp130 directly and in the absence of any additional membrane-bound co-receptor (Gearing et al., Science 255: 1434-1437, 1992). Following OSM binding to gp130, OSMRβ or LIFRα are recruited to form a high-affinity signaling complex (Mosley et al., J Biol. Chem. 271: 32635-32643, 1996). Activation of either receptor results in signaling via the JAK/STAT pathway (Auguste et al., J Biol. Chem. 272: 15760-15764, 1997).

OSM is produced primarily by cells of immune system origin and, has been a target for diseases associated with autoimmune disorders. Previous work has shown that several OSM antagonists may reduce tumor detachment and reduce STAT3, JNK, ERK, and AKT phosphorylation in a number of cancer cell lines (U.S. patent application Ser. No. 15/403,965, herein incorporated by reference in its entirety).

It is an object of the present in invention to provide novel OSM antagonist pharmaceutical compositions and their use in preventing cancer metastasis.

SUMMARY OF THE INVENTION

To achieve these and other advantages, and in accordance with the purposes of the present invention, as embodied and broadly described herein, the present invention relates to a method of reducing tumor cell detachment, proliferation and/or metastasis involving administering at least one OSM antagonist or OSM receptor antagonist to a subject. In a preferred embodiment the tumor cells are those associated with prostate or breast cancer.

Any number of OSM or OSM receptor antagonists may be employed, alone, or in combination with other therapies for treating or reducing metastasis and tumor cell migration. OSM antagonists may include small molecules, antibodies, antibody-derived reagents, or chimeric molecules. Included in the definition of antagonist is a structural or functional mimetic of any such molecule described above. Also contemplated are nucleic acid molecules such as DNA or RNA aptamers.

The antagonist may function by blocking OSM from interaction with the OSM receptor gp130, or the other OSM receptors, OSMrβ chain or LIFr, or by blocking formation of heterodimers of these proteins, and as such prevent OSM binding and signaling thereby reducing synthesis of cytokines and/or matrix metalloproteinases (MMPs). The antagonist according to the invention may therefore be a ligand for either OSM or one or more of the OSM receptors (gp130, OSMrβ or LIFr) or an agent capable of interfering with these interactions in a manner which affects OSM biological activity. Hereinafter reference to an antagonist to OSM can be taken to mean either an antagonist to OSM itself or to one of its receptors.

Administration of at least one OSM or OSM receptor antagonist, alone, or in combination with one or more therapies can be administered to a patient in need thereof to reduce tumor cell detachment, proliferation and/or metastasis.

Other embodiments provide a pharmaceutical composition including an OSM antagonist in an amount effective to inhibit or reduce tumor cell detachment, proliferation and/or metastasis. Another embodiment provides methods for inhibiting tumor cell detachment, proliferation and/or metastasis by administering an OSM antagonist. Preferably, the OSM antagonist specifically binds to OSM or the OSM receptor and inhibits or reduces OSM biological activity. Another embodiment provides methods for identifying inhibitors of OSM.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION OF THE INVENTION

Figure 1:
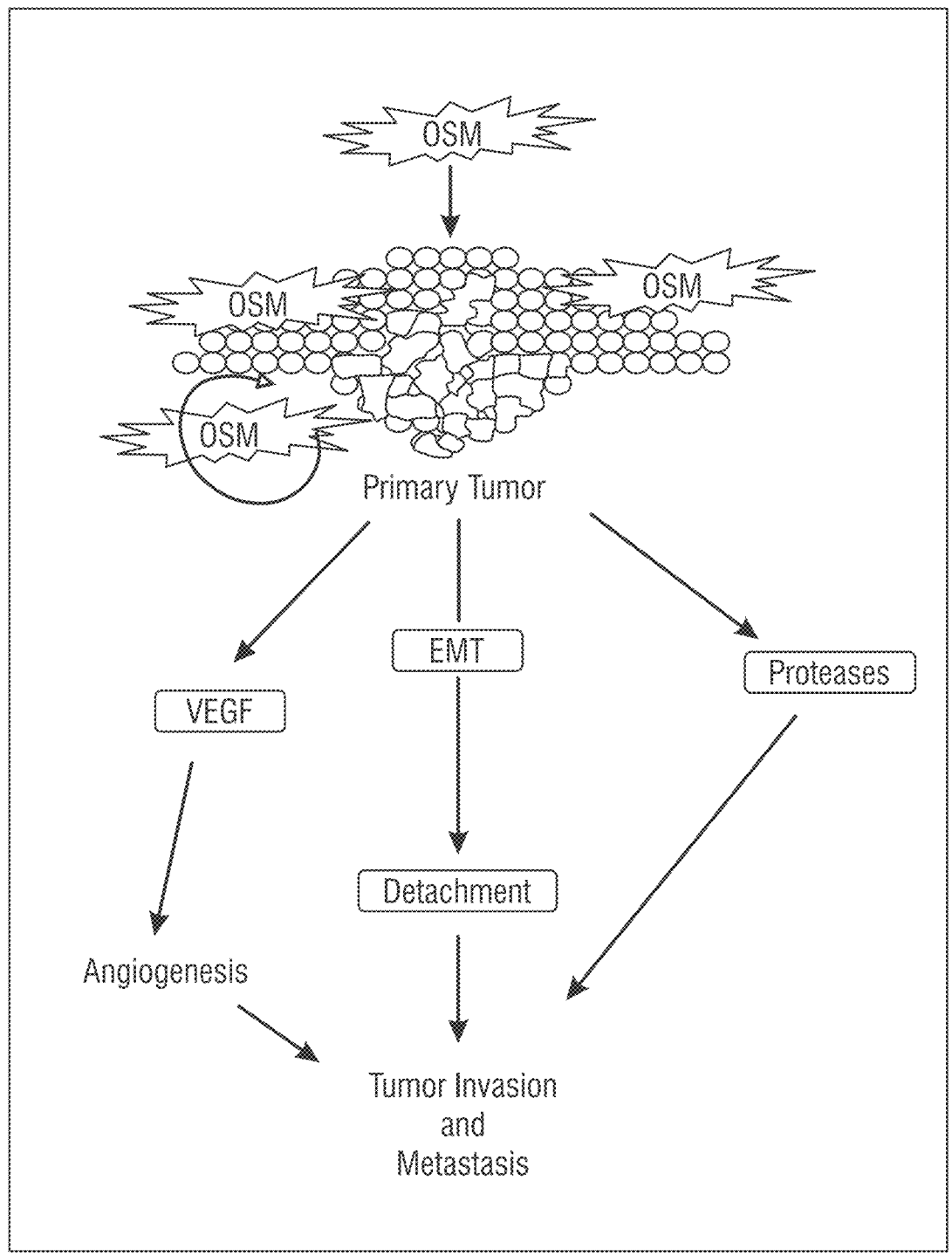
FIG. 1 shows a schematic of the mechanism by which OSM is presumed to promote the metastasis and progression of prostate tumors.

The present disclosure generally relates to treatment of cancer, and, more specifically, to the inhibition of signaling molecules implicated in the invasion and metastasis of cancer. Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification are approximations that may vary depending upon the desired properties sought to be obtained by the present embodiments. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the features disclosed herein are presented below. Not all features of a physical implementation are necessarily described or shown in this application for the sake of clarity. It is to be understood that in the development of a physical embodiment incorporating the embodiments of the present disclosure, numerous implementation-specific decisions can be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill the art and having benefit of this disclosure.

While compositions and methods are described herein in terms of "comprising" various components or steps, the compositions and methods can also "consist essentially of" or "consist of" the various components and steps.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease. Disease and disorder are used interchangeably herein.

The terms "inhibit" and "antagonize", as used herein, mean to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

As used herein, the terms "effective amount" or "therapeutically effective amount" or "pharmaceutically effective amount" of a compound are used interchangeably to refer to the amount of the compound which is sufficient to provide a beneficial effect to the subject to which the compound is administered. The term to "treat," as used herein, means reducing the frequency with which symptoms are experienced by a patient or subject or administering an agent or compound to reduce the severity with which symptoms are experienced. An appropriate therapeutic amount in any individual case may be determined by one of ordinary skill in the art using routine experimentation. By the term "specifically bind" or "specifically binds," as used herein, is meant that a first molecule (e.g., an antibody) preferentially binds to a second molecule (e.g., a particular antigenic epitope), but does not necessarily bind only to that second molecule. As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration. The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound and are physiologically acceptable to the subject. Supplementary active compounds may also be incorporated into the compositions.

As used herein, the term "antagonist" generally refers to the property of a molecule, compound or other agent to, for example, interfere with the binding of one molecule with another molecule or the stimulation of one cell by another cell either through steric hindrance, conformational alterations or other biochemical mechanisms. In one regard, the term antagonist relates to the property of an agent to prevent the binding of a receptor to its ligand, e.g., the binding of OSM with gp 130 or other OSM receptors, thereby inhibiting the signal transduction pathway triggered by OSM. The term antagonist is not limited by any specific action mechanism, but, rather, refers generally to the functional property presently defined. Antagonists of the present invention include but are not limited to small molecules and chemical compounds that bind to OSM or one of its receptors as well as OSM antibodies and fragments, muteins, and modifications thereof, peptides, and nucleic acid molecules such as antisense or RNAi compounds that inhibit expression of OSM.

As used herein, the term "heavy chain antibody" or "heavy chain antibodies" comprises immunoglobulin molecules derived from camelid species, either by immunization with an antigen and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease or prepared by the cloning and expression of VH (variable heavy chain immunoglobulin) genes from an animal.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

By the term "applicator," as the term is used herein, is meant any device including, but not limited to, a hypodermic syringe, a pipette, and the like, for administering the compounds and compositions of the invention.

As used herein, "aptamer" refers to a small molecule that can bind specifically to another molecule. Aptamers are typically either polynucleotide- or peptide-based molecules. A polynucleotidal aptamer is a DNA or RNA molecule, usually comprising several strands of nucleic acids, that adopt highly specific three-dimensional conformation designed to have appropriate binding affinities and specificities towards specific target molecules, such as peptides, proteins, drugs, vitamins, among other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

As used herein "endogenous" refers to any material from or produced inside an organism, cell, tissue or system.

As used herein, the term "exogenous" refers to any material introduced from or produced outside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly five amino acids and/or sugars in size. One skilled in the art understands that generally the overall three-dimensional structure, rather than the specific linear sequence of the molecule, is the main criterion of antigenic specificity and therefore distinguishes one epitope from another.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides. The term "peptide" typically refers to short polypeptides. Conventional notation is used herein to portray polypeptide sequences: the left-hand end of a polypeptide sequence is the amino-terminus; the right-hand end of a polypeptide sequence is the carboxyl-terminus.

As used herein, a "peptidomimetic" is a compound containing non-peptidic structural elements that is capable of mimicking the biological action of a parent peptide. A peptidomimetic may or may not comprise peptide bonds.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

I). OSM Antagonists

The antagonist may function by blocking OSM from interaction with the OSM receptor gp130, or the other OSM receptors, OSMrβ chain or LIFr, or by blocking formation of heterodimers of these proteins, and as such prevent OSM binding and signaling thereby reducing synthesis of cytokines and/or MMPs. The antagonist according to the invention may therefore be a ligand for either OSM or one or more of the OSM receptors (gp130, OSMrβ or LIFr) or an agent capable of interfering with these interactions in a manner which affects OSM biological activity. Hereinafter reference to an antagonist to OSM can be taken to mean either an antagonist to OSM itself or to one of its receptors.

Nucleic acid and amino acid sequences are known and generally available to those of skill in the art at places such as Gen bank, Swiss Prot, and EMBL. They are also disclosed herein as SEQ ID NOS:1 and 2. Further, amino acid residues which are important for OSM's interaction with gp130 have been identified. From the published amino acid sequence of OSM (Malik et al., 1989, Mol. Cell. Biol., 9(7), 2847-53, DNA sequence entry M27288 in EMBL database, protein sequence entry P13725 in Swissprot) these are G120, Q16 and Q20; N123 and N124 may also play a part. The first 25 residues are a signal peptide, and the mature protein begins at the sequence AAIGS. The sequence is numbered from the first amino acid of the mature protein as shown ion SEQ ID NO: 1.

The invention therefore further provides an antagonist or agent capable of interacting with one or more of these specific residues and/or the binding sites they help to define on OSM to alter OSM biological activity.

Potential antagonists of OSM include small organic molecules, ions which interact specifically with OSM for example a substrate possibly a natural substrate, a cell membrane component, a receptor or a natural ligand, a fragment thereof or a peptide or other proteinaceous molecule, particularly preferred is a non-signaling mutant form of OSM which will block binding of OSM to the OSM receptor, but also modified OSM molecules. Such antagonists may be in the form of DNA encoding the protein or peptide and may be delivered for in vivo expression of said antagonist. Antagonists may be vaccines comprising such protein or peptide molecules or DNA, designed to produce an antagonistic effect towards OSM via induction of antibody responses in vivo targeted towards native OSM. Such antagonists may also include antibodies, antibody-derived reagents or chimeric molecules. Included in the definition of antagonist is a structural or functional mimetic of any such molecule described above. Also contemplated are nucleic acid molecules such as DNA or RNA aptamers.

OSM antagonists of the present invention include, where applicable, functional equivalents. For example, molecules may differ in length, structure, components, etc., but may still retain one or more of the defined functions. Preferred OSM antagonist small molecules may be modified to include side groups, or other chemical additions which do not affect the antagonist activity.

Further, functional equivalents of the antibodies, antibody fragments or peptides of the present invention may include mimetic compounds, i.e., constructs designed to mimic the proper configuration and/or orientation for antigen binding.

OSM antagonists may optionally be modified by addition of side groups, etc., e.g., by amino terminal acylation, carboxy terminal amidation or by coupling of additional groups to amino acid side chains. Antagonists may also comprise one or more conservative amino acid substitutions. By "conservative amino acid substitutions" is meant those changes in amino acid sequence that preserve the general charge, hydrophobicity/hydrophilicity and/or steric bulk of the amino acid substituted. For example, substitutions between the following groups are conservative: Gly/Ala, Val/Ile/Leu, Asp/Glu, Lys/Arg, Asn/Gln, Ser/Cys/Thr, and Phe/Trp/Tyr. Such modifications will not substantially diminish the efficacy of the OSM antagonists and may impart such desired properties as, for example, increased in vivo half-life or decreased toxicity. The invention is also intended to include polypeptides bearing modifications other than the insertion, deletion, or substitution of amino acid residues. By way of example, the modifications may be covalent in nature, and include for example, chemical bonding with polymers, lipids, other organic, and inorganic moieties. Such derivatives may be prepared to increase circulating half-life of a polypeptide or may be designed to improve targeting capacity for the polypeptide to desired cells, tissues, or organs. Similarly, the invention further embraces OSM or OSMR polypeptides that have been covalently modified to include one or more water soluble polymer attachments such as polyethylene glycol, polyoxyethylene glycol, or polypropylene glycol.

A. OSM Small Molecules

Preferred antagonists include small organic molecules. Such compounds may be from any class of compound but will be selected on the basis of their ability to affect the biological activity of OSM through one of the mechanisms described above and will be physiologically acceptable (non-toxic or demonstrating an acceptable level of toxicity or other side-effects). One class of compounds which may provide useful antagonists are ribonucleosides such as N-(1H-pyrazolo[3,4-d]pyrimidin-4-yl) benzamide); Davoll and Kerridge, J. Chem Soc., 2589, 1961).

Small molecules, including OSM-SMI-8, OSM-SMI-10, OSM-SMI-11, OSM-SMI-23, OSM-SMI-26, and OSM-SMI-27 have been predicted and OSM-SMI-8, OSM-SMI-10, and OSM-SMI-11 have also been shown to inhibit OSM induced prostate tumor cell detachment and other phosphorylation of proteins related to metastasis, including STAT3, JNK, ERK, and AKT.

According to the invention, other OSM small molecule antagonists, include those listed herein, with a similar structure to OSM-SMI-8, OSM-SMI-10, OSM-SMI-23, OSM-SMI-26, and OSM-SMI-27 may also have the same inhibition of OSM induced detachment and phosphorylation. Several of these structures are listed in Tables 1 to 5. Any stereochemistry depicted in the formula's in Tables 1 to 5 is intended to be informative only and non-limiting. Any compound with the same basic chemical formula is intended to be included as are derivatives, isomers, and modifications.

TABLE 1

OSM-SMI-8 and compounds based thereupon.

| Compound Number | Compound Structure |
| --- | --- |
| OSM-SMI-8 | 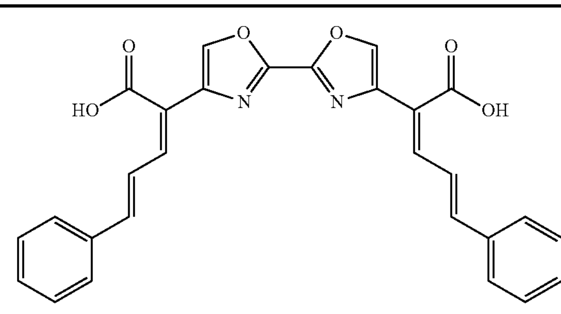 |
| OSM-SMI-8A | 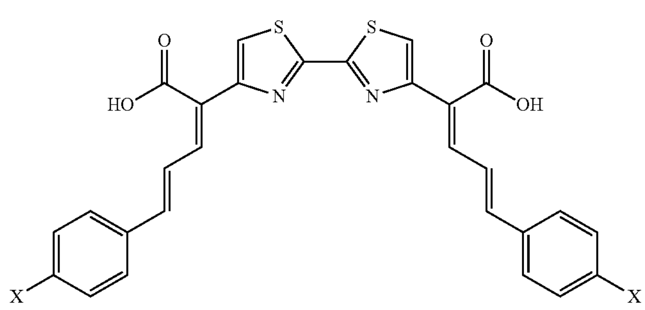 |

TABLE 1-continued

OSM-SMI-8 and compounds based thereupon.

| Compound Number | Compound Structure |
|---|---|
| OSM-SMI-8B | 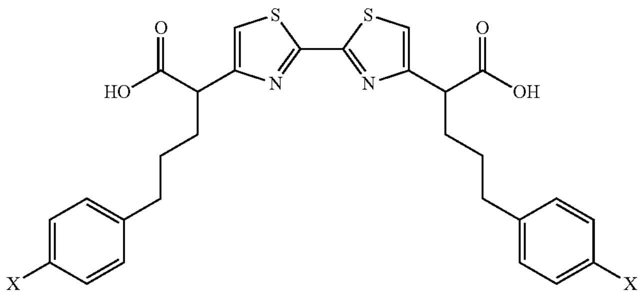 |
| OSM-SMI-8C | 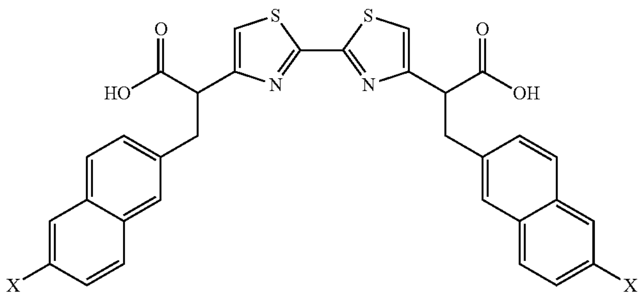 |
| OSM-SMI-8D | 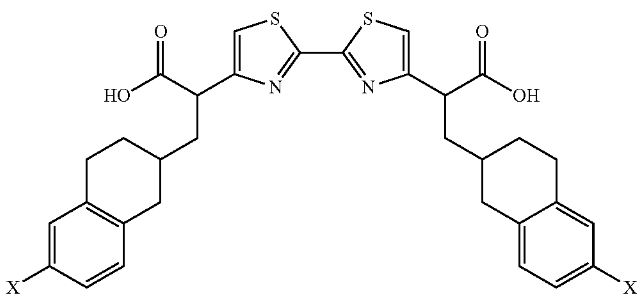 |
| OSM-SMI-8E | 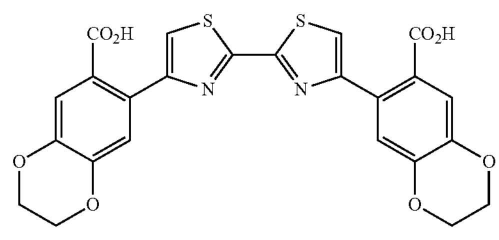 [SMILES: O=C(O)c1cc2c(cc1-c1csc(-c3nc(-c4cc5c(cc4C(=O)O)OCCO5)cs3)n1)OCCO2] |
| OSM-SMI-8F | 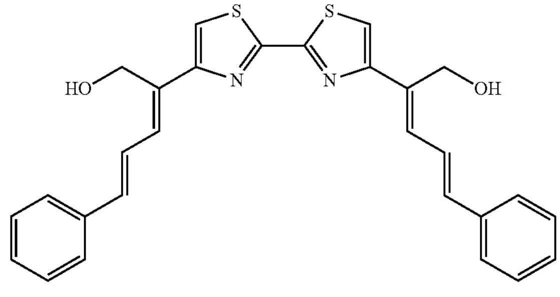 [SMILES: OC/C(=C\C=C\c1ccccc1)c1csc(-c2nc(/C(=C/C=C/c3ccccc3)CO)cs2)n1] |

TABLE 1-continued

OSM-SMI-8 and compounds based thereupon.

| Compound Number | Compound Structure |
|---|---|
| OSM-SMI-8G | 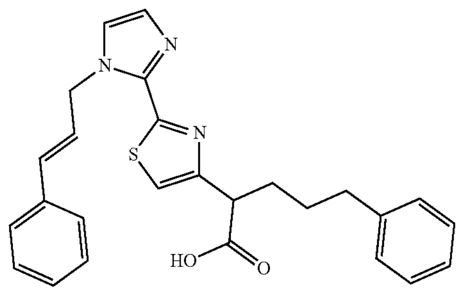 [SMILES: O=C(O)C(CCCc1ccccc1)c1csc(-c2nccn2C/C=C/c2ccccc2)n1] |
| OSM-SMI-8H | 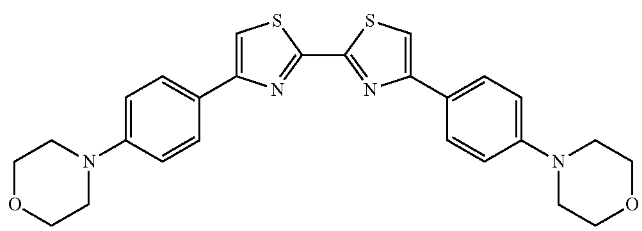 [SMILES: c1cc(N2CCOCC2)ccc1-c1csc(-c2nc(-c3ccc(N4CCOCC4)cc3)cs2)n1] |
| OSM-SMI-8I | 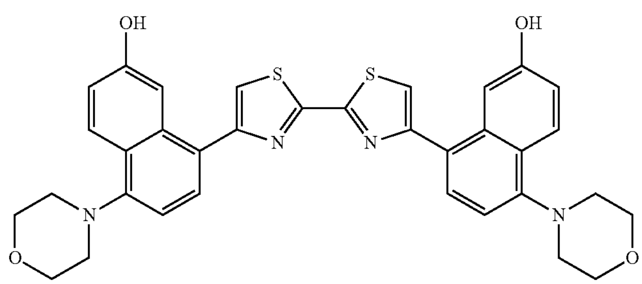 [SMILES: Oc1ccc2c(N3CCOCC3)ccc(-c3csc(-c4nc(-c5ccc(N6CCOCC6)c6ccc(O)cc56)cs4)n3)c2c1] |
| OSM-SMI-8J | 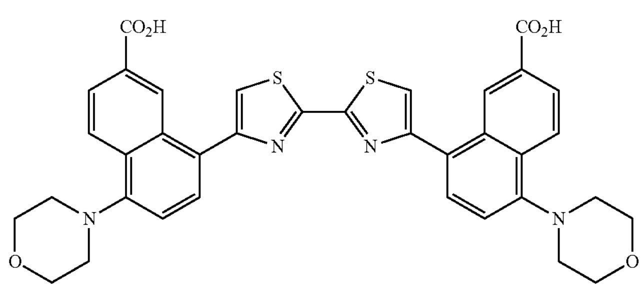 [SMILES: O=C(O)c1ccc2c(N3CCOCC3)ccc(-c3csc(-c4nc(-c5ccc(N6CCOCC6)c6ccc(C(=O)O)cc56)cs4)n3)c2c1] |

Where X may be the same or different and be any functional group, such as, but not limited to, H, $CF_3$, $CH_3$, $OCH_3$, and/or $NO_2$.

TABLE 2
OSM-SMI-10 and compounds based thereupon.
| Compound Number | Compound Structure |
|---|---|
| OSM-SMI-10 | 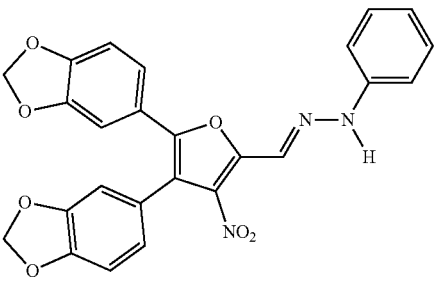 [SMILES: O=[N+]([O-])c1c(/C=N/Nc2ccccc2)oc(-c2ccc3c(c2)OCO3)c1-c1ccc2c(c1)OCO2] |
| OSM-SMI-10A | 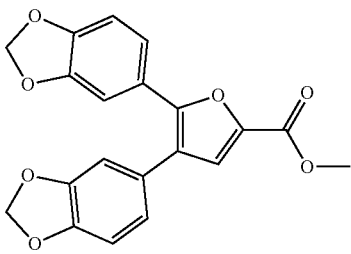 [SMILES: COC(=O)c1cc(-c2ccc3c(c2)OCO3)c(-c2ccc3c(c2)OCO3)o1] |
| OSM-SMI-10B | 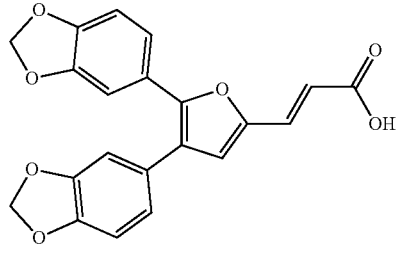 [SMILES: O=C(O)/C=C/c1cc(-c2ccc3c(c2)OCO3)c(-c2ccc3c(c2)OCO3)o1] |
| OSM-SMI-10C | 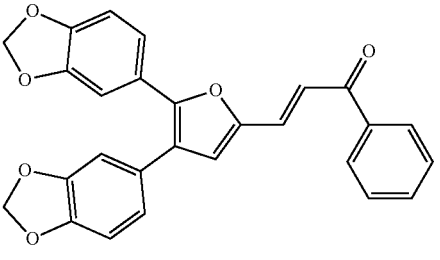 [SMILES: O=C(/C=C/c1cc(-c2ccc3c(c2)OCO3)c(-c2ccc3c(c2)OCO3)o1)c1ccccc1] |
| OSM-SMI-10D | 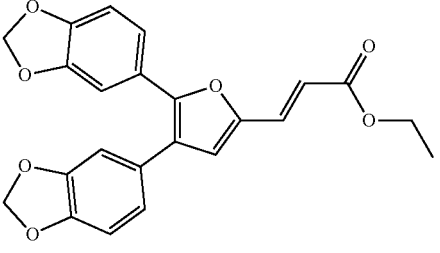 [SMILES: CCOC(=O)/C=C/c1cc(-c2ccc3c(c2)OCO3)c(-c2ccc3c(c2)OCO3)o1] |

TABLE 2-continued
OSM-SMI-10 and compounds based thereupon.
| Compound Number | Compound Structure |
|---|---|
| OSM-SMI-10E | 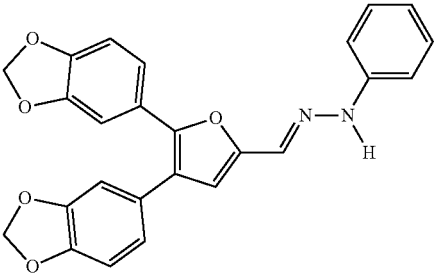 [SMILES: C(=N\Nc1ccccc1)/c1cc(-c2ccc3c(c2)OCO3)c(-c2ccc3c(c2)OCO3)o1] |
| OSM-SMI-10F | 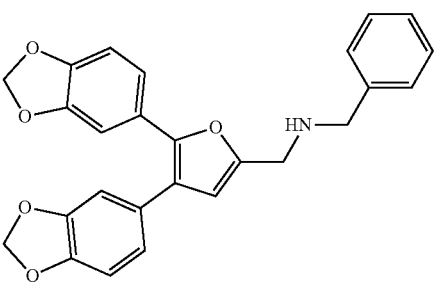 [SMILES: c1ccc(CNCc2cc(-c3ccc4c(c3)OCO4)c(-c3ccc4c(c3)OCO4)o2)cc1] |
| OSM-SMI-10G | 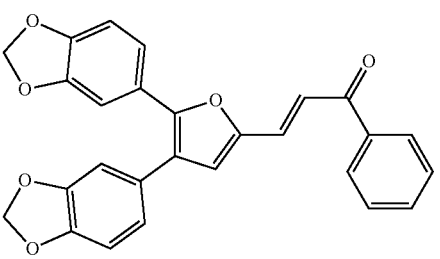 [SMILES: O=C(/C=C/c1cc(-c2ccc3c(c2)OCO3)c(-c2ccc3c(c2)OCO3)o1)c1ccccc1] |
| OSM-SMI-10H | 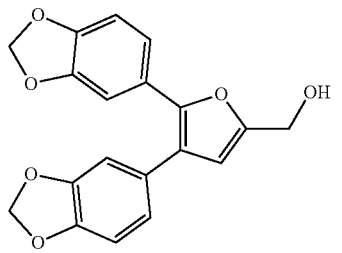 [SMILES: OCc1cc(-c2ccc3c(c2)OCO3)c(-c2ccc3c(c2)OCO3)o1] |
| OSM-SMI-10I | 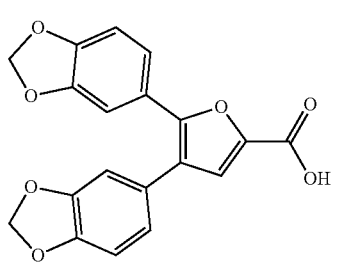 [SMILES: O=C(O)c1cc(-c2ccc3c(c2)OCO3)c(-c2ccc3c(c2)OCO3)o1] |

TABLE 2-continued
OSM-SMI-10 and compounds based thereupon.
| Compound Number | Compound Structure |
|---|---|
| OSM-SMI-10J | 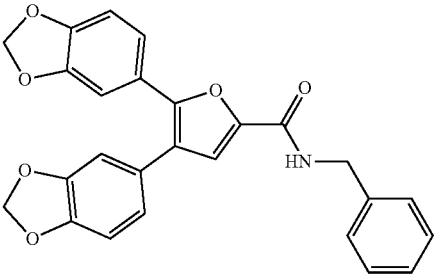 [SMILES: O=C(NCc1ccccc1)c1cc(-c2ccc3c(c2)OCO3)c(-c2ccc3c(c2)OCO3)o1] |
| OSM-SMI-10B-3 | 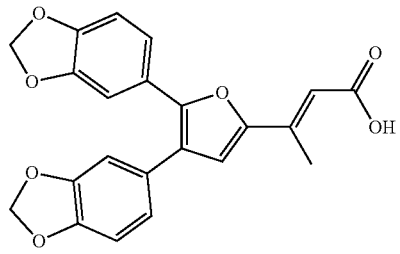 [SMILES: C/C(=C\C(=O)O)c1cc(-c2ccc3c(c2)OCO3)c(-c2ccc3c(c2)OCO3)o1] |
| OSM-SMI-10B-5 | 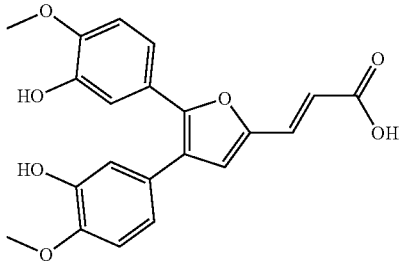 [SMILES: COc1ccc(-c2cc(/C=C/C(=O)O)oc2-c2ccc(OC)c(O)c2)cc1O] |
| OSM-SMI-10B-6 | 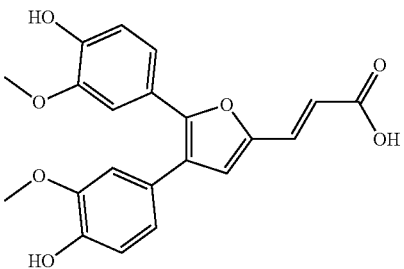 [SMILES: COc1cc(-c2cc(/C=C/C(=O)O)oc2-c2ccc(O)c(OC)c2)ccc1O] |
| OSM-SMI-10B-4 | 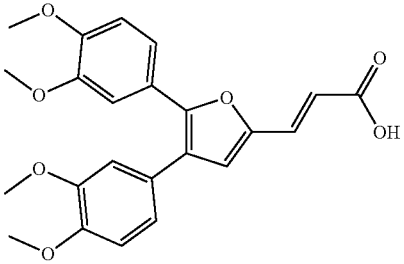 [SMILES: COc1ccc(-c2cc(/C=C/C(=O)O)oc2-c2ccc(OC)c(OC)c2)cc1OC] |

TABLE 2-continued

OSM-SMI-10 and compounds based thereupon.

| Compound Number | Compound Structure |
| --- | --- |
| OSM-SMI-10B-10 | 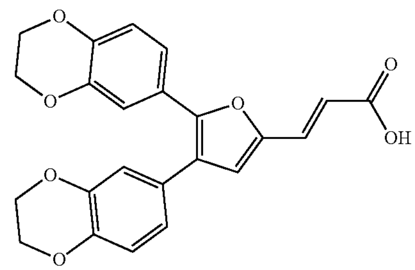 [SMILES: O=C(O)/C=C/c1cc(-c2ccc3c(c2)OCCO3)c(-c2ccc3c(c2)OCCO3)o1] |
| OSM-SMI-10B-11 | 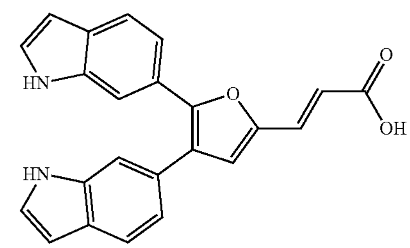 [SMILES: O=C(O)/C=C/c1cc(-c2ccc3cc[nH]c3c2)c(-c2ccc3cc[nH]c3c2)o1] |
| OSM-SMI-10B-7 | 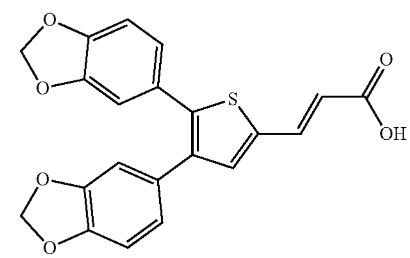 [SMILES: O=C(O)/C=C/c1cc(-c2ccc3c(c2)OCO3)c(-c2ccc3c(c2)OCO3)s1] |
| OSM-SMI-10B-9 | 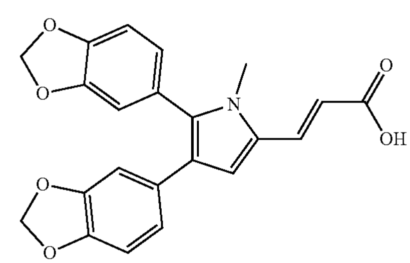 [SMILES: Cn1c(/C=C/C(=O)O)cc(-c2ccc3c(c2)OCO3)c1-c1ccc2c(c1)OCO2] |
| OSM-SMI-10B-8 | 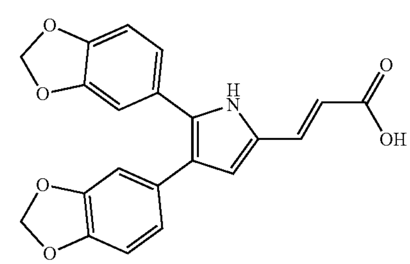 [SMILES: O=C(O)/C=C/c1cc(-c2ccc3c(c2)OCO3)c(-c2ccc3c(c2)OCO3)[nH]1] |
| OSM-SMI-10B-12 | 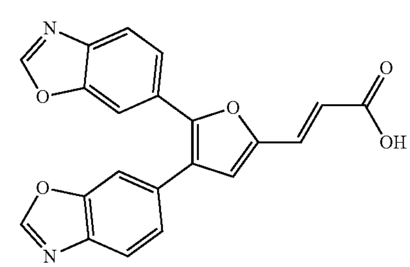 [SMILES: O=C(O)/C=C/c1cc(-c2ccc3ncoc3c2)c(-c2ccc3ncoc3c2)o1] |

TABLE 2-continued

OSM-SMI-10 and compounds based thereupon.

| Compound Number | Compound Structure |
| --- | --- |
| OSM-SMI-10B-17 | 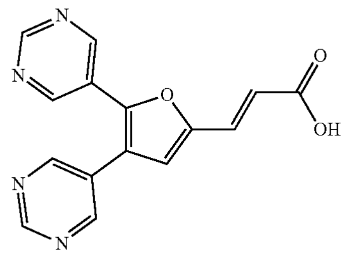 [SMILES: O=C(O)/C=C/c1cc(-c2cncnc2)c(-c2cncnc2)o1] |
| OSM-SMI-10B-13 | 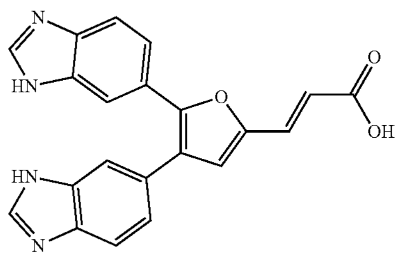 [SMILES: O=C(O)/C=C/c1cc(-c2ccc3nc[nH]c3c2)c(-c2ccc3nc[nH]c3c2)o1] |
| OSM-SMI-10B-14 | 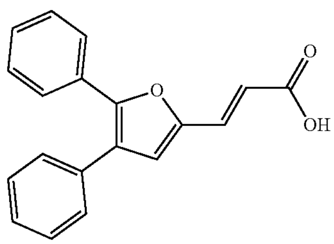 [SMILES: O=C(O)/C=C/c1cc(-c2ccccc2)c(-c2ccccc2)o1] |
| OSM-SMI-10B-15 | 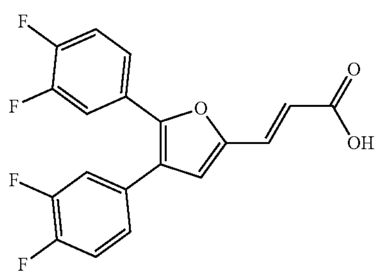 [SMILES: O=C(O)/C=C/c1cc(-c2ccc(F)c(F)c2)c(-c2ccc(F)c(F)c2)o1] |
| OSM-SMI-10B-20 | 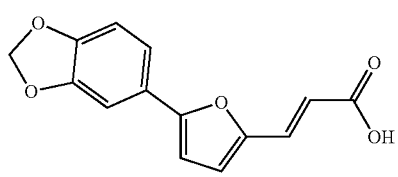 [SMILES: O=C(O)/C=C/c1ccc(-c2ccc3c(c2)OCO3)o1] |
| OSM-SMI-10B-21 | 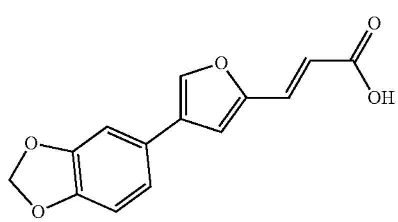 [SMILES: O=C(O)/C=C/c1cc(-c2ccc3c(c2)OCO3)co1] |

TABLE 2-continued
OSM-SMI-10 and compounds based thereupon.
| Compound Number | Compound Structure |
|---|---|
| OSM-SMI-10B-16 | 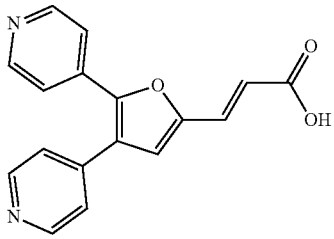 [SMILES: O=C(O)/C=C/c1cc(-c2ccncc2)c(-c2ccncc2)o1] |
| OSM-SMI-10B-26 | 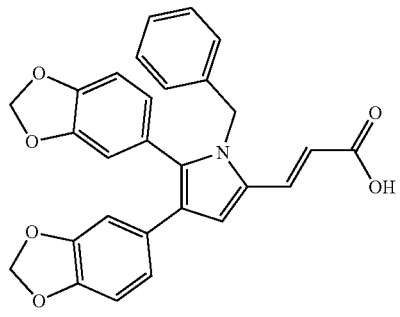 [SMILES: O=C(O)/C=C/c1cc(-c2ccc3c(c2)OCO3)c(-c2ccc3c(c2)OCO3)n1Cc1ccccc1] |
| OSM-SMI-10J-1 | 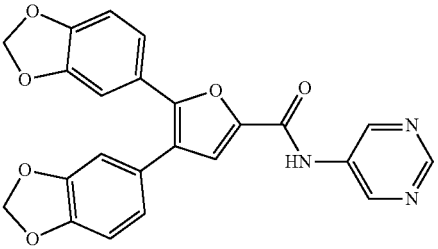 [SMILES: O=C(Nc1cncnc1)c1cc(-c2ccc3c(c2)OCO3)c(-c2ccc3c(c2)OCO3)o1] |
| OSM-SMI-10J-2 | 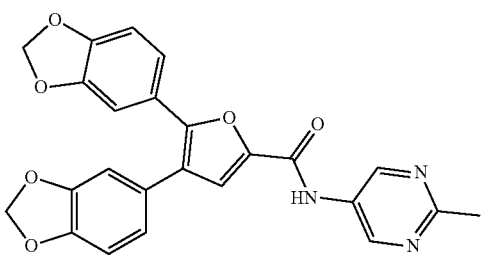 [SMILES: Cc1ncc(NC(=O)c2cc(-c3ccc4c(c3)OCO4)c(-c3ccc4c(c3)OCO4)o2)cn1] |
| OSM-SMI-10J-3 | 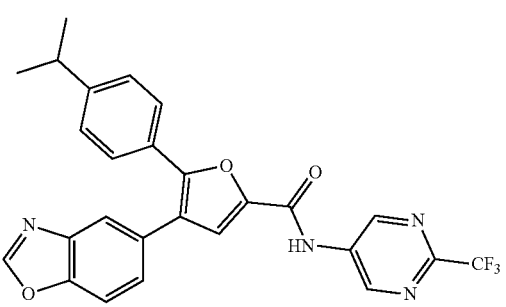 [SMILES: CC(C)c1ccc(-c2oc(C(=O)Nc3cnc(C(F)(F)F)nc3)cc2-c2ccc3ocnc3c2)cc1] |

TABLE 2-continued

OSM-SMI-10 and compounds based thereupon.

| Compound Number | Compound Structure |
| --- | --- |
| OSM-SMI-10J-4 | (structure: 5-(4-methylphenyl)-4-(benzo[d]oxazol-5-yl)-furan-2-carboxamide linked to N-(2-(trifluoromethyl)pyrimidin-5-yl)) |
| OSM-SMI-10J-5 | (structure: 5-(4-methylphenyl)-4-(2,3-dihydrobenzo[b][1,4]dioxin-6-yl)-furan-2-carboxamide linked to N-(2-(trifluoromethyl)pyrimidin-5-yl)) |
| OSM-SMI-10J-6 | (structure: 5-(4-isopropylphenyl)-4-(2,3-dihydrobenzo[b][1,4]dioxin-6-yl)-furan-2-carboxamide linked to N-(2-(trifluoromethyl)pyrimidin-5-yl)) |
| OSM-SMI-10B-1 | (structure: 5-(benzo[d][1,3]dioxol-5-yl)-4-(benzo[d][1,3]dioxol-5-yl)-furan-2-yl acrylate, sodium salt) |
| OSM-SMI-10B-2 | (structure: 5-(benzo[d][1,3]dioxol-5-yl)-4-(benzo[d][1,3]dioxol-5-yl)-furan-2-yl acrylate, triethylammonium salt) |

TABLE 2-continued

OSM-SMI-10 and compounds based thereupon.

| Compound Number | Compound Structure |
|---|---|
| OSM-SMI-10B-18 | 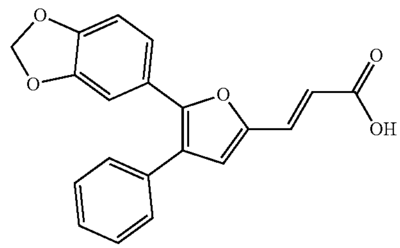 [SMILES: O=C(O)/C=C/c1cc(-c2ccccc2)c(-c2ccc3c(c2)OCO3)o1] |
| OSM-SMI-10B-19 | 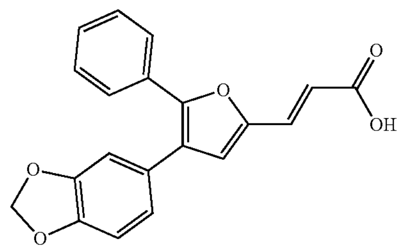 [SMILES: O=C(O)/C=C/c1cc(-c2ccc3c(c2)OCO3)c(-c2ccccc2)o1] |
| OSM-SMI-10B-22 | 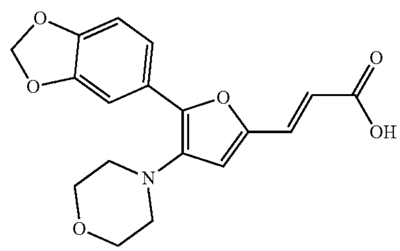 [SMILES: O=C(O)/C=C/c1cc(N2CCOCC2)c(-c2ccc3c(c2)OCO3)o1] |
| OSM-SMI-10B-23 | 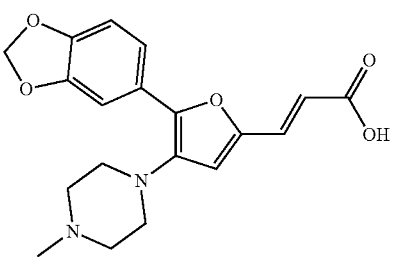 [SMILES: CN1CCN(c2cc(/C=C/C(=O)O)oc2-c2ccc3c(c2)OCO3)CC1] |
| OSM-SMI-10B-24 | 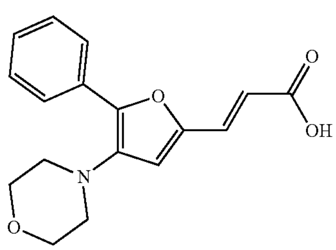 [SMILES: O=C(O)/C=C/c1cc(N2CCOCC2)c(-c2ccccc2)o1] |
| OSM-SMI-10B-25 | 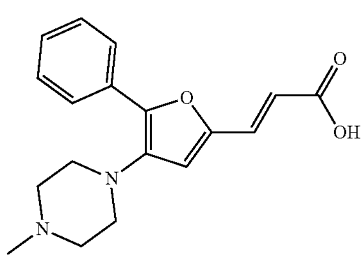 [SMILES: CN1CCN(c2cc(/C=C/C(=O)O)oc2-c2ccccc2)CC1] |

TABLE 2-continued

OSM-SMI-10 and compounds based thereupon.

| Compound Number | Compound Structure |
|---|---|
| OSM-SMI-10K-1 | 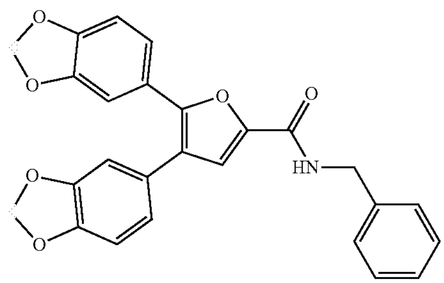 |
| OSM-SMI-10K-2 | 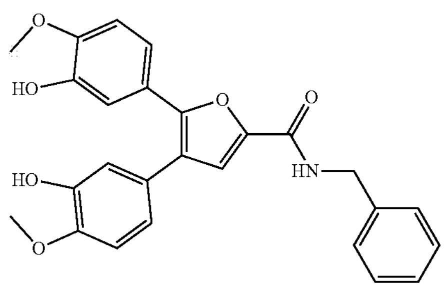 [SMILES: COc1ccc(-c2cc(C(=O)NCc3ccccc3)oc2-c2ccc(OC)c(O)c2)cc1O] |
| OSM-SMI-10K-3 | 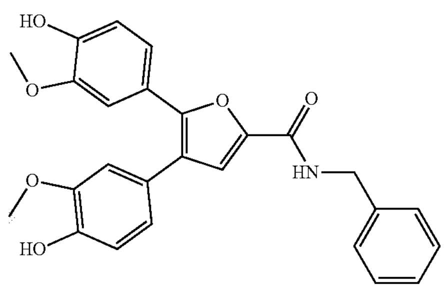 [SMILES: COc1cc(-c2cc(C(=O)NCc3ccccc3)oc2-c2ccc(O)c(OC)c2)ccc1O] |
| OSM-SMI-10K-4 | 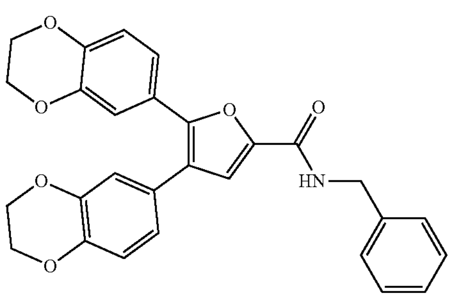 [SMILES: O=C(NCc1ccccc1)c1cc(-c2ccc3c(c2)OCCO3)c(-c2ccc3c(c2)OCCO3)o1] |
| OSM-SMI-10K-5 | 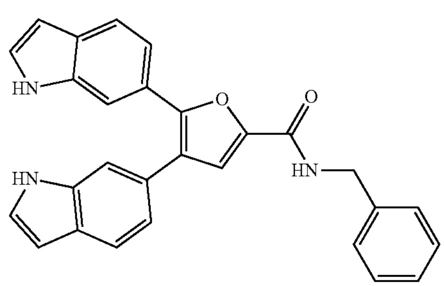 [SMILES: O=C(NCc1ccccc1)c1cc(-c2ccc3cc[nH]c3c2)c(-c2ccc3cc[nH]c3c2)o1] |

TABLE 2-continued
OSM-SMI-10 and compounds based thereupon.
| Compound Number | Compound Structure |
|---|---|
| OSM-SMI-10K-6 | 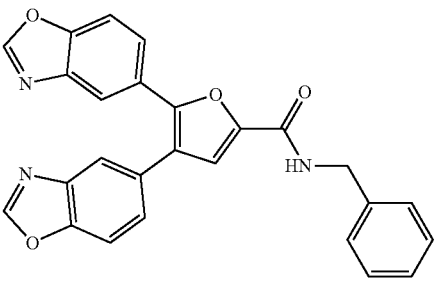 [SMILES: O=C(NCc1ccccc1)c1cc(-c2ccc3ocnc3c2)c(-c2ccc3ocnc3c2)o1] |
| OSM-SMI-10K-7 | 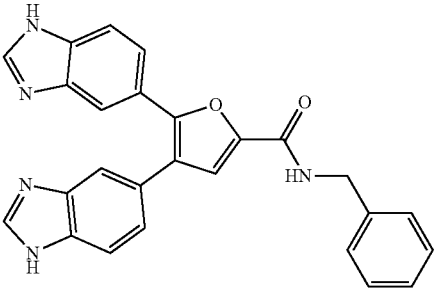 [SMILES: O=C(NCc1ccccc1)c1cc(-c2ccc3[nH]cnc3c2)c(-c2ccc3[nH]cnc3c2)o1] |
| OSM-SMI-10L | 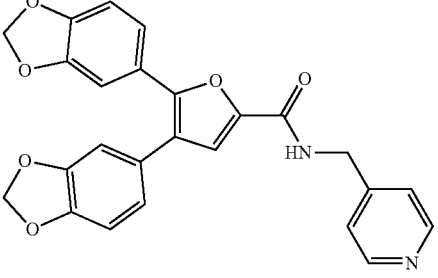 |
| OSM-SMI-10M | 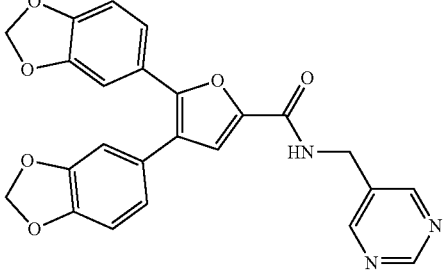 |
| OSM-SMI-10N | 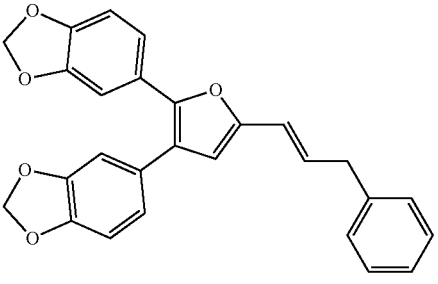 [SMILES: C(=C\c1cc(-c2ccc3c(c2)OCO3)c(-c2ccc3c(c2)OCO3)o1)/Cc1ccccc1] |

TABLE 2-continued
OSM-SMI-10 and compounds based thereupon.
| Compound Number | Compound Structure |
|---|---|
| OSM-SMI-10O | 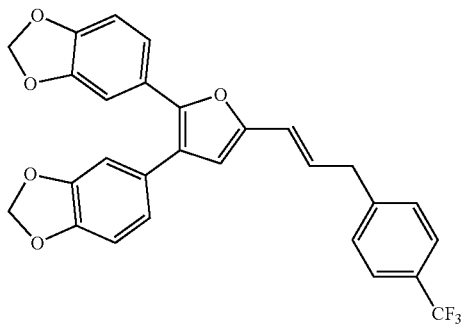 [SMILES: FC(F)(F)c1ccc(C/C=C/c2cc(-c3ccc4c(c3)OCO4)c(-c3ccc4c(c3)OCO4)o2)cc1] |
| OSM-SMI-10P | 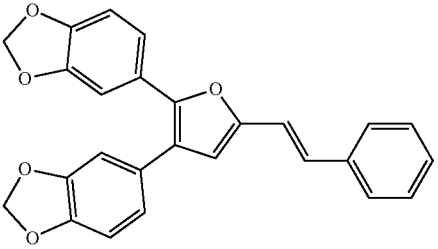 [SMILES: C(=C\c1cc(-c2ccc3c(c2)OCO3)c(-c2ccc3c(c2)OCO3)o1)/c1ccccc1] |
| OSM-SMI-10Q | 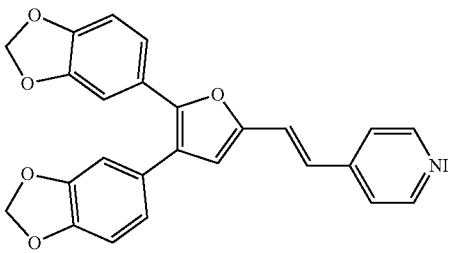 |
| OSM-SMI-10R | 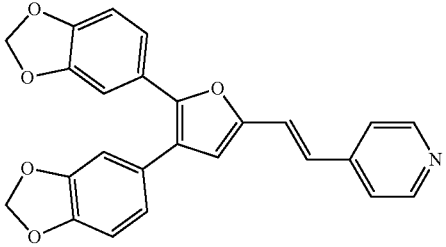 [SMILES: C(=C\c1cc(-c2ccc3c(c2)OCO3)c(-c2ccc3c(c2)OCO3)o1)/c1ccncc1] |
| OSM-SMI-10B-27 | 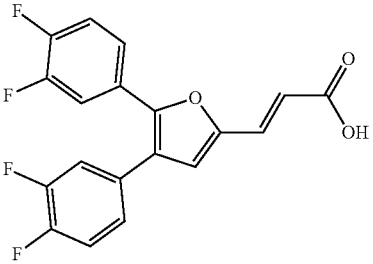 [SMILES: O=C(O)/C=C/c1cc(-c2ccc(F)c(F)c2)c(-c2ccc(F)c(F)c2)o1] |

TABLE 2-continued

OSM-SMI-10 and compounds based thereupon.

| Compound Number | Compound Structure |
| --- | --- |
| OSM-SMI-10B-28 | 5-(4-chlorophenyl)-4-(4-chlorophenyl)furan-2-yl acrylic acid |
| OSM-SMI-10B-29 | 5-(4-methylphenyl)-4-(4-methylphenyl)furan-2-yl acrylic acid |
| OSM-SMI-10B-30 | 5-(3-chlorophenyl)-4-(3-chlorophenyl)furan-2-yl acrylic acid |
| OSM-SMI-10B-31 | 5-(4-methoxyphenyl)-4-(4-methoxyphenyl)furan-2-yl acrylic acid |
| OSM-SMI-10B-32 | 5-(4-dimethylaminophenyl)-4-(4-dimethylaminophenyl)furan-2-yl acrylic acid |

TABLE 2-continued

OSM-SMI-10 and compounds based thereupon.

| Compound Number | Compound Structure |
| --- | --- |
| OSM-SMI-10B-33 | 2,3-bis(3-(dimethylamino)phenyl)furan-5-yl acrylic acid |
| OSM-SMI-10B-34 | 2,3-bis(4-nitrophenyl)furan-5-yl acrylic acid |
| OSM-SMI-10B-35 | 2,3-bis(4-nitro-3-(trifluoromethyl)phenyl)furan-5-yl acrylic acid |
| OSM-SMI-10B-36 | 2,3-bis(4-tert-butylphenyl)furan-5-yl acrylic acid |

TABLE 2-continued
OSM-SMI-10 and compounds based thereupon.
| Compound Number | Compound Structure |
|---|---|
| OSM-SMI-10B-37 | 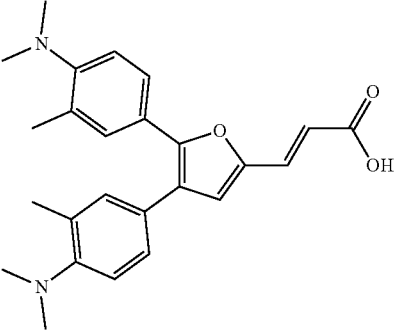 [SMILES: Cc1cc(-c2cc(/C=C/C(=O)O)oc2-c2ccc(N(C)C)c(C)c2)ccc1N(C)C] |
| OSM-SMI-10S-1 | 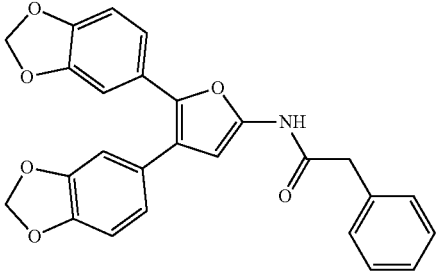 [SMILES: O=C(Cc1ccccc1)Nc1cc(-c2ccc3c(c2)OCO3)c(-c2ccc3c(c2)OCO3)o1] |
| OSM-SMI-10S-2 | 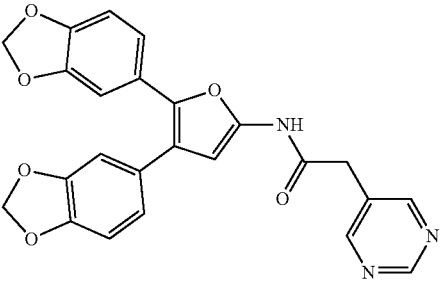 [SMILES: O=C(Cc1cncnc1)Nc1cc(-c2ccc3c(c2)OCO3)c(-c2ccc3c(c2)OCO3)o1] |
| OSM-SMI-10S-3 | 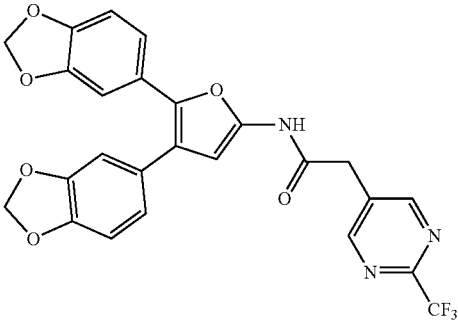 [SMILES: O=C(Cc1cnc(C(F)(F)F)nc1)Nc1cc(-c2ccc3c(c2)OCO3)c(-c2ccc3c(c2)OCO3)o1] |
| OSM-SMI-10K-8 | 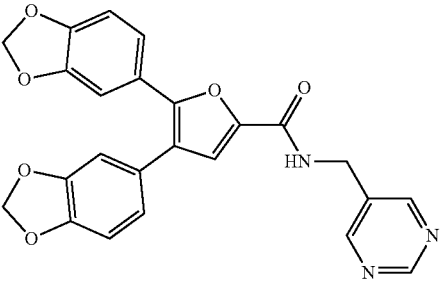 [SMILES: O=C(NCc1cncnc1)c1cc(-c2ccc3c(c2)OCO3)c(-c2ccc3c(c2)OCO3)o1] |

TABLE 2-continued

OSM-SMI-10 and compounds based thereupon.

| Compound Number | Compound Structure |
|---|---|
| OSM-SMI-10K-9 | *structure* |

TABLE 3

OSM-SMI-23 and compounds based thereupon.

| Compound Number | Compound Structure |
|---|---|
| OSM-SMI-23 | *structure* |
| OSM-SMI-23A | *structure* |
| OSM-SMI-23A-1 | *structure* |

TABLE 3-continued
OSM-SMI-23 and compounds based thereupon.
| Compound Number | Compound Structure |
|---|---|
| OSM-SMI-23A-2 | 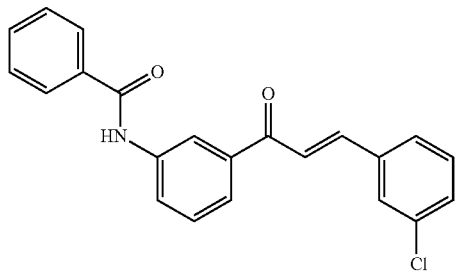 [SMILES: O=C(/C=C/c1cccc(Cl)c1)c1cccc(NC(=O)c2ccccc2)c1] |
| OSM-SMI-23A-3 | 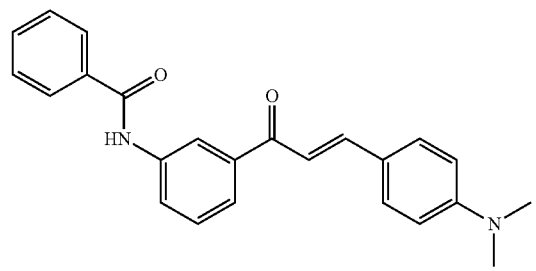 [SMILES: CN(C)c1ccc(/C=C/C(=O)c2cccc(NC(=O)c3ccccc3)c2)cc1] |
| OSM-SMI-23A-4 | 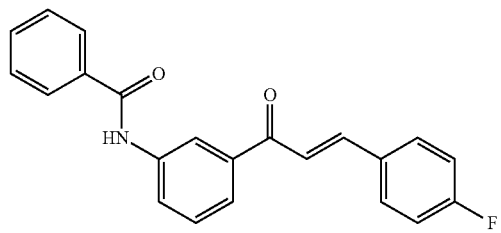 [SMILES: O=C(/C=C/c1ccc(F)cc1)c1cccc(NC(=O)c2ccccc2)c1] |
| OSM-SMI-23A-5 | 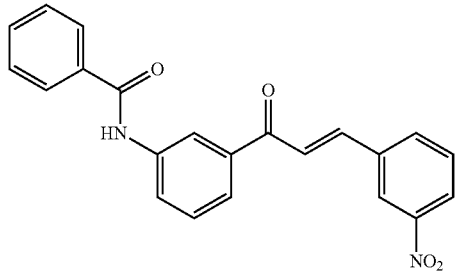 [SMILES: O=C(/C=C/c1cccc([N+](=O)[O-])c1)c1cccc(NC(=O)c2ccccc2)c1] |
| OSM-SMI-23A-6 | 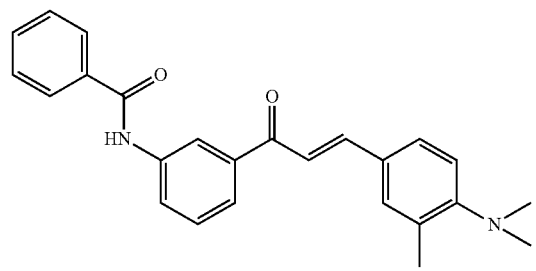 [SMILES: Cc1cc(/C=C/C(=O)c2cccc(NC(=O)c3ccccc3)c2)ccc1N(C)C] |

TABLE 3-continued

OSM-SMI-23 and compounds based thereupon.

| Compound Number | Compound Structure |
| --- | --- |
| OSM-SMI-23A-7 | (structure) |
| OSM-SMI-23B | (structure) |
| OSM-SMI-23B-1 | (structure) |
| OSM-SMI-23B-2 | (structure) |
| OSM-SMI-23B-3 | (structure) |

TABLE 3-continued
OSM-SMI-23 and compounds based thereupon.
| Compound Number | Compound Structure |
|---|---|
| OSM-SMI-23B-4 | 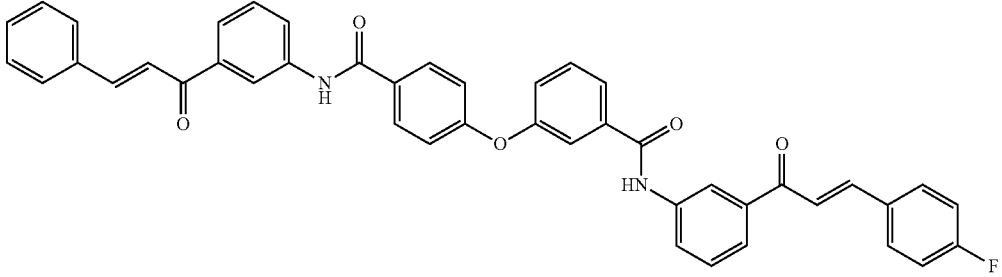 [SMILES: O=C(/C=C/c1ccccc1)c1cccc(NC(=O)c2ccc(Oc3cccc(C(=O)Nc4cccc(C(=O)/C=C/c5ccc(F)cc5)c4)c3)cc2)c1] |
| OSM-SMI-23B-5 | 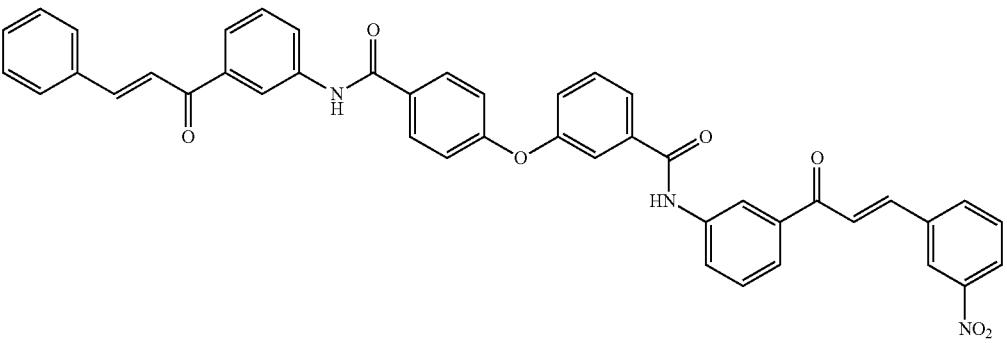 [SMILES: O=C(/C=C/c1ccccc1)c1cccc(NC(=O)c2ccc(Oc3cccc(C(=O)Nc4cccc(C(=O)/C=C/c5cccc([N+](=O)[O-])c5)c4)c3)cc2)c1] |
| OSM-SMI-23B-6 | 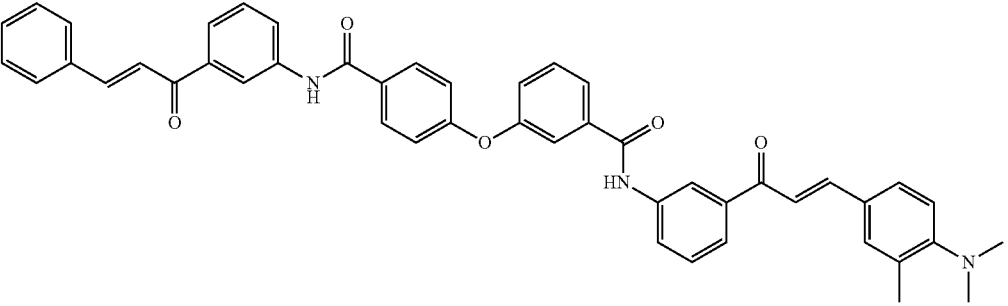 |
| OSM-SMI-23B-7 | 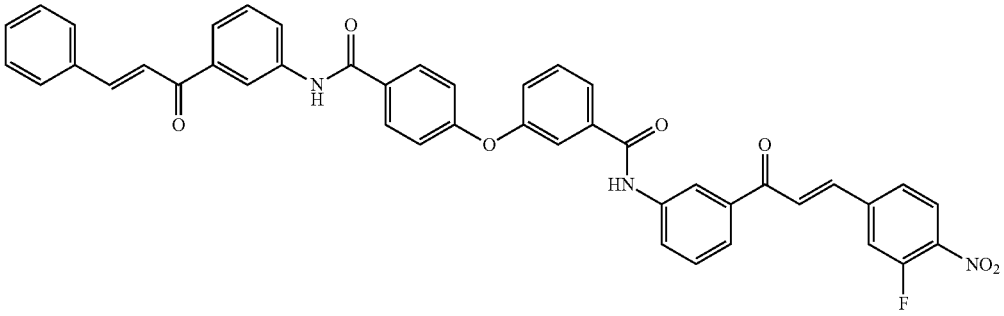 [SMILES: O=C(/C=C/c1ccccc1)c1cccc(NC(=O)c2ccc(Oc3cccc(C(=O)Nc4cccc(C(=O)/C=C/c5ccc([N+](=O)[O-])c(F)c5)c4)c3)cc2)c1] |
| OSM-SMI-23C | 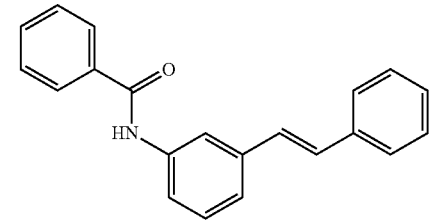 [SMILES: O=C(Nc1cccc(/C=C/c2ccccc2)c1)c1ccccc1] |

TABLE 3-continued

OSM-SMI-23 and compounds based thereupon.

| Compound Number | Compound Structure |
| --- | --- |
| OSM-SMI-23D | 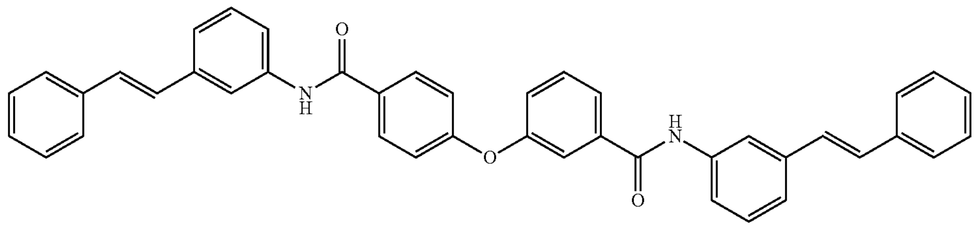 [SMILES: O=C(Nc1cccc(/C=C/c2ccccc2)c1)c1ccc(Oc2cccc(C(=O)Nc3cccc(/C=C/c4ccccc4)c3)c2)cc1] |
| OSM-SMI-23F | |
| OSM-SMI-23F | |
| OSM-SMI-23G | 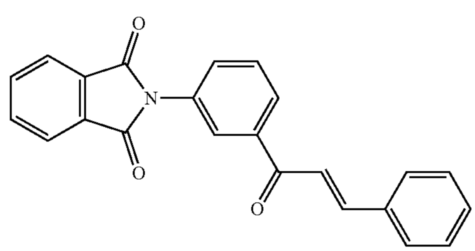 [SMILES: O=C(/C=C/c1ccccc1)c1cccc(N2C(=O)c3ccccc3C2=O)c1] |
| OSM-SMI-23H | 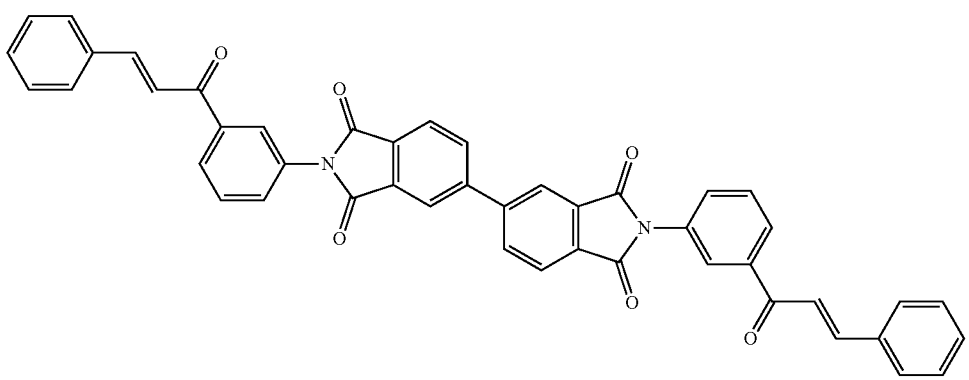 [SMILES: O=C(/C=C/c1ccccc1)c1cccc(N2C(=O)c3ccc(-c4ccc5c(c4)C(=O)N(c4cccc(C(=O)/C=C/c6ccccc6)c4)C5=O)cc3C2=O)c1] |

TABLE 3-continued

OSM-SMI-23 and compounds based thereupon.

| Compound Number | Compound Structure |
| --- | --- |
| OSM-SMI-23I | 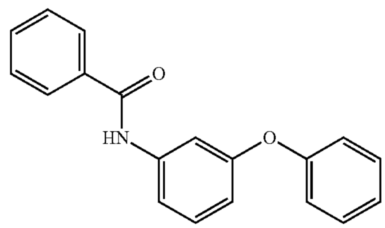 [SMILES: O=C(Nc1cccc(Oc2ccccc2)c1)c1ccccc1] |
| OSM-SMI-23J | 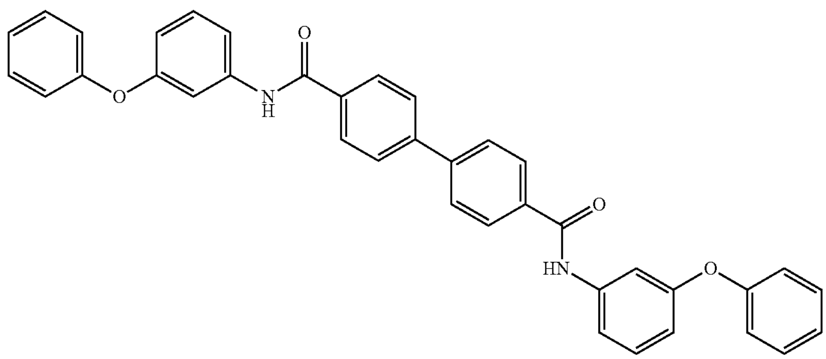 [SMILES: O=C(Nc1cccc(Oc2ccccc2)c1)c1ccc(-c2ccc(C(=O)Nc3cccc(Oc4ccccc4)c3)cc2)cc1] |
| OSM-SMI-23K | 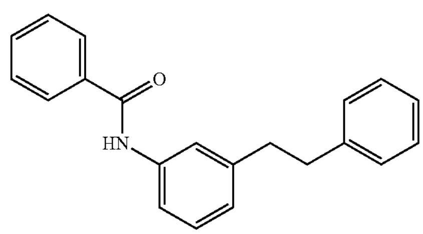 [SMILES: O=C(Nc1cccc(CCc2ccccc2)c1)c1ccccc1] |
| OSM-SMI-23L | 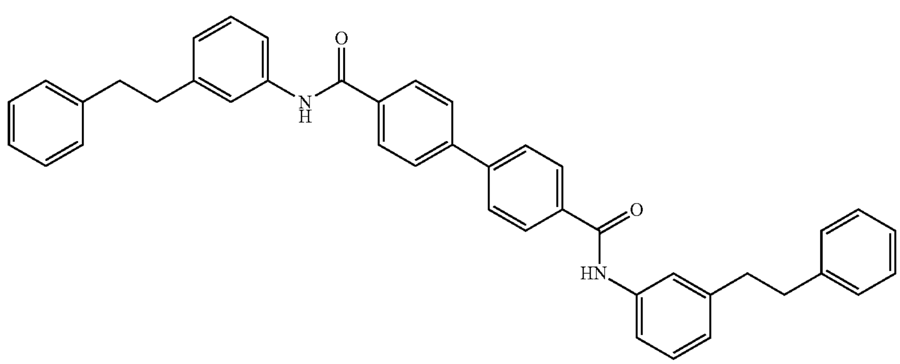 [SMILES: O=C(Nc1cccc(CCc2ccccc2)c1)c1ccc(-c2ccc(C(=O)Nc3cccc(CCc4ccccc4)c3)cc2)cc1] |
| OSM-SMI-23M | 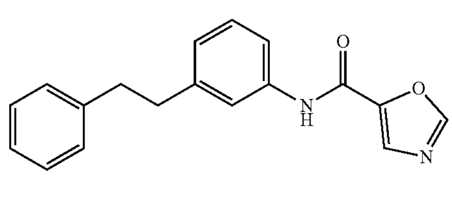 [SMILES: O=C(Nc1cccc(CCc2ccccc2)c1)c1cnco1] |

TABLE 3-continued

OSM-SMI-23 and compounds based thereupon.

| Compound Number | Compound Structure |
|---|---|
| OSM-SMI-23N | 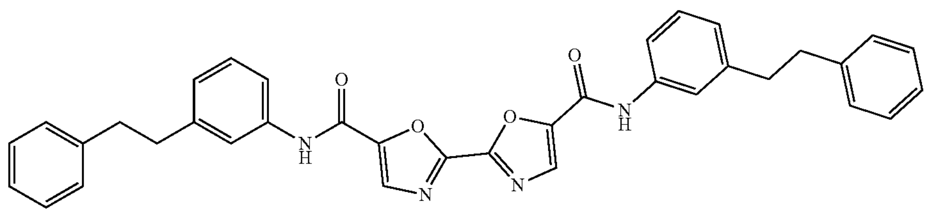 [SMILES: O=C(Nc1cccc(CCc2ccccc2)c1)c1cnc(-c2ncc(C(=O)Nc3cccc(CCc4ccccc4)c3)o2)o1] |
| OSM-SMI-23O | 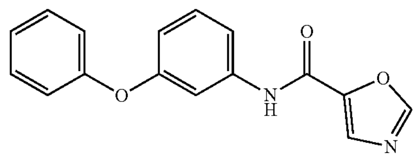 [SMILES: O=C(Nc1cccc(Oc2ccccc2)c1)c1cnco1] |
| OSM-SMI-23P | 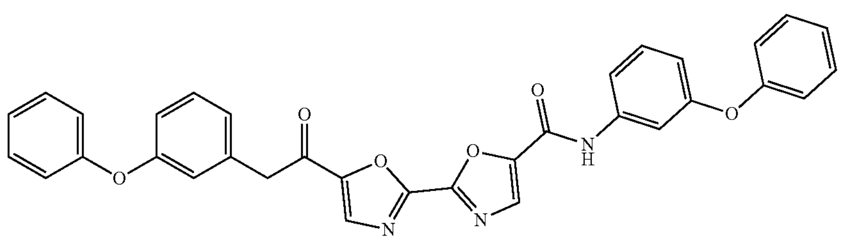 [SMILES: O=C(Cc1cccc(Oc2ccccc2)c1)c1cnc(-c2ncc(C(=O)Nc3cccc(Oc4ccccc4)c3)o2)o1] |
| OSM-SMI-23Q | 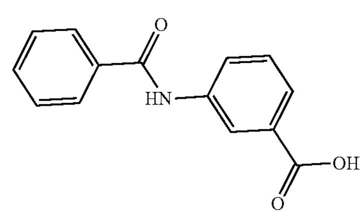 [SMILES: O=C(O)c1cccc(NC(=O)c2ccccc2)c1] |
| OSM-SMI-23R | 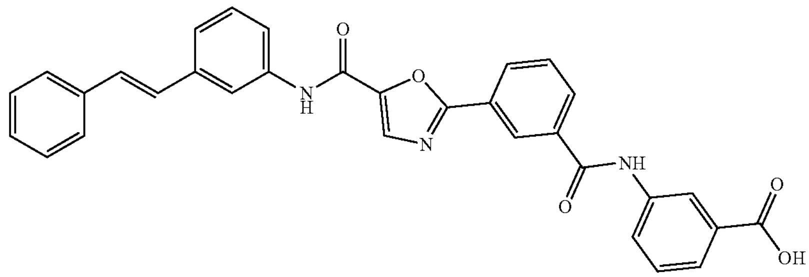 [SMILES: O=C(O)c1cccc(NC(=O)c2cccc(-c3ncc(C(=O)Nc4cccc(/C=C/c5ccccc5)c4)o3)c2)c1] |

TABLE 4
OSM-SMI-26 and compounds based thereupon.
| Compound Number | Compound Structure |
|---|---|
| OSM-SMI-26 (SMI-26) | 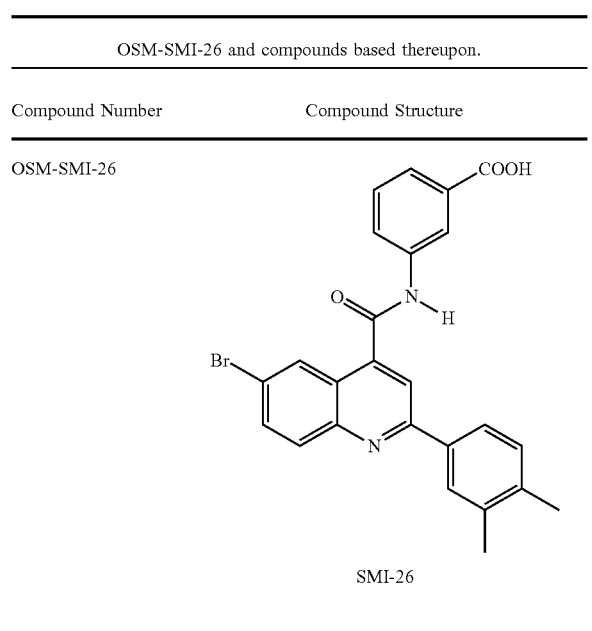 |
| OSM-SMI-26A | |
| OSM-SMI-26B | |
| OSM-SMI-26C | 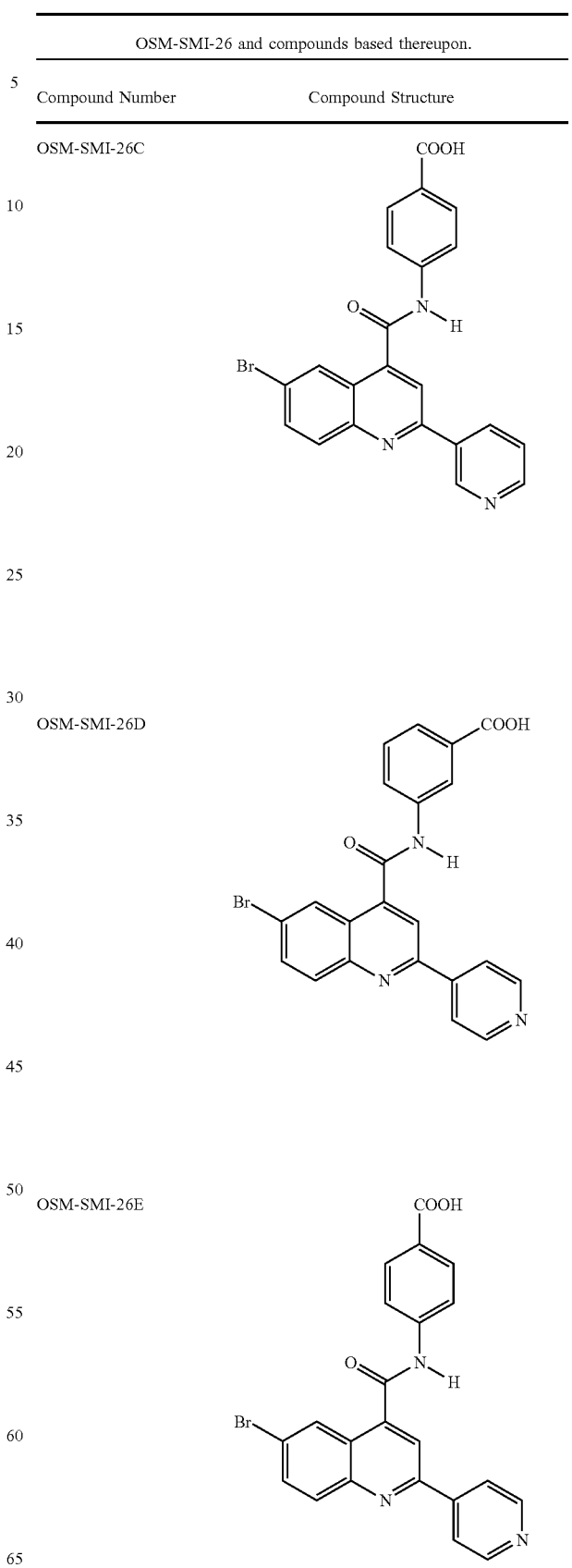 |
| OSM-SMI-26D | 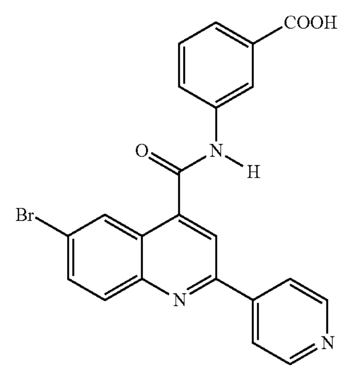 [SMILES: O=C(O)c1cccc(NC(=O)c2cc(-c3ccncc3)nc3ccc(Br)cc23)c1] |
| OSM-SMI-26E | 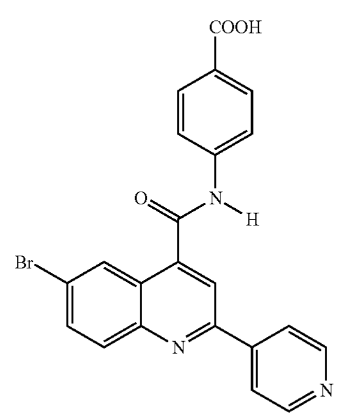 [SMILES: O=C(O)c1ccc(NC(=O)c2cc(-c3ccncc3)nc3ccc(Br)cc23)cc1] |

TABLE 4-continued

OSM-SMI-26 and compounds based thereupon.

| Compound Number | Compound Structure |
|---|---|
| OSM-SMI-26F | 3-(6-fluoro-2-(3,4-dimethylphenyl)quinoline-4-carboxamido)benzoic acid |
| OSM-SMI-26G | 4-(6-fluoro-2-(3,4-dimethylphenyl)quinoline-4-carboxamido)benzoic acid |
| OSM-SMI-26H | 3-(6-fluoro-2-(pyridin-3-yl)quinoline-4-carboxamido)benzoic acid |
| OSM-SMI-26I | 4-(6-fluoro-2-(pyridin-3-yl)quinoline-4-carboxamido)benzoic acid |
| OSM-SMI-26J | 3-(6-fluoro-2-(pyridin-4-yl)quinoline-4-carboxamido)benzoic acid |
| OSM-SMI-26K | 4-(6-fluoro-2-(pyridin-4-yl)quinoline-4-carboxamido)benzoic acid |
| OSM-SMI-26L | 3-(6-chloro-2-(3,4-dimethylphenyl)quinoline-4-carboxamido)benzoic acid |

TABLE 4-continued
OSM-SMI-26 and compounds based thereupon.
| Compound Number | Compound Structure |
|---|---|
| OSM-SMI-26M | 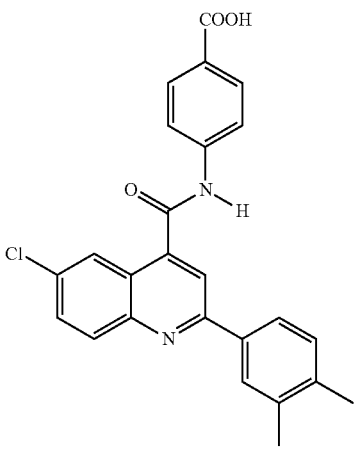 [SMILES: Cc1ccc(-c2cc(C(=O)Nc3ccc(C(=O)O)cc3)c3cc(Cl)ccc3n2)cc1C] |
| OSM-SMI-26N | 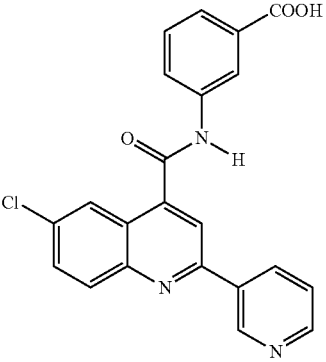 |
| OSM-SMI-26O | 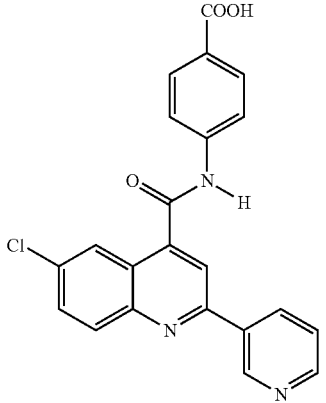 |
| OSM-SMI-26P | |
| OSM-SMI-26Q | |
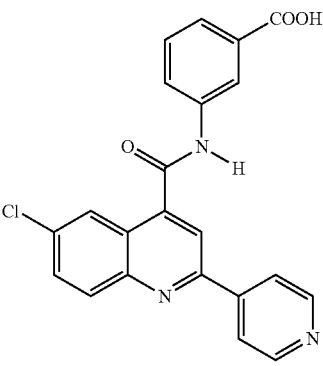 [SMILES: O=C(O)c1cccc(NC(=O)c2cc(-c3ccncc3)nc3ccc(Cl)cc23)c1]

TABLE 5

OSM-SMI-27 and compounds based thereupon.

| Compound Number | Compound Structure |
|---|---|
| OSM-SMI-27 | 2-phenyl-N-benzylquinazoline-4-carboxamide |
| OSM-SMI-27-A0 | 2-(p-tolyl)quinazoline-4-carboxylic acid |
| OSM-SMI-27-A1 | 2-(p-tolyl)-N-benzylquinazoline-4-carboxamide |
| OSM-SMI-27-A2 | 2-(p-tolyl)-N-(pyridin-3-ylmethyl)quinazoline-4-carboxamide |
| OSM-SMI-27-A3 | 2-(p-tolyl)-N-(4-(trifluoromethyl)benzyl)quinazoline-4-carboxamide |
| OSM-SMI-27-A4 | 2-(p-tolyl)-N-((6-(trifluoromethyl)pyridin-3-yl)methyl)quinazoline-4-carboxamide |

TABLE 5-continued

OSM-SMI-27 and compounds based thereupon.

| Compound Number | Compound Structure |
| --- | --- |
| OSM-SMI-27-A5 | 2-(p-tolyl)-N-phenylquinazoline-4-carboxamide |
| OSM-SMI-27-A6 | 2-(p-tolyl)-N-(4-(trifluoromethyl)phenyl)quinazoline-4-carboxamide |
| OSM-SMI-27-A7 | 2-(p-tolyl)-N-phenethylquinazoline-4-carboxamide |
| OSM-SMI-27-A8 | 2-(p-tolyl)-N-(4-(trifluoromethyl)phenethyl)quinazoline-4-carboxamide |
| OSM-SMI-27-A9 | 2-(p-tolyl)-N-(4-(trifluoromethyl)benzyl)-6-(trifluoromethyl)quinazoline-4-carboxamide |
| OSM-SMI-27-A10 | 2-(p-tolyl)-N-phenyl-6-(trifluoromethyl)quinazoline-4-carboxamide |

TABLE 5-continued
OSM-SMI-27 and compounds based thereupon.
| Compound Number | Compound Structure |
|---|---|
| OSM-SMI-27-A11 | 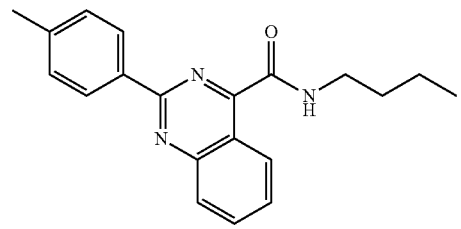 [SMILES: CCCCNC(=O)c1nc(-c2ccc(C)cc2)nc2ccccc12] |
| OSM-SMI-27-B0 | 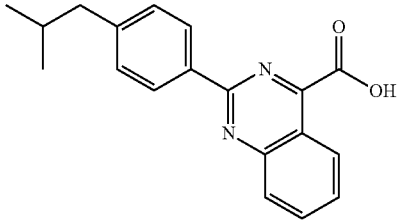 [SMILES: CC(C)Cc1ccc(-c2nc(C(=O)O)c3ccccc3n2)cc1] |
| OSM-SMI-27-B1 | 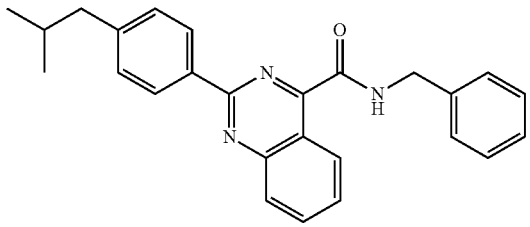 [SMILES: CC(C)Cc1ccc(-c2nc(C(=O)NCc3ccccc3)c3ccccc3n2)cc1] |
| OSM-SMI-27-B2 | 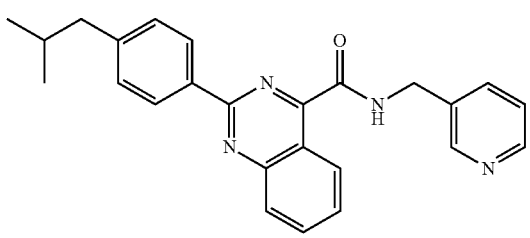 [SMILES: CC(C)Cc1ccc(-c2nc(C(=O)NCc3cccnc3)c3ccccc3n2)cc1] |
| OSM-SMI-27-B3 | 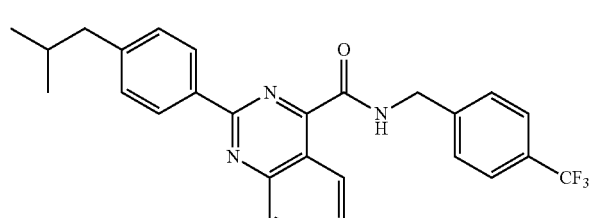 |
| OSM-SMI-27-B4 | 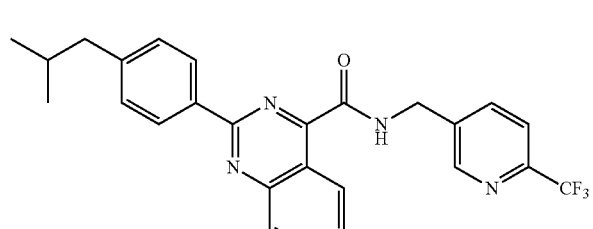 |

TABLE 5-continued
OSM-SMI-27 and compounds based thereupon.
| Compound Number | Compound Structure |
|---|---|
| OSM-SMI-27-B5 | 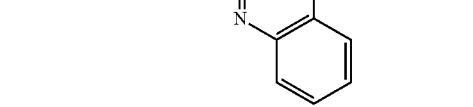 |
| OSM-SMI-27-B6 | 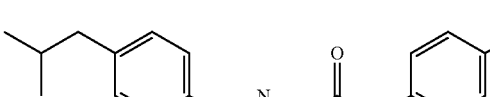 |
| OSM-SMI-27-B7 | 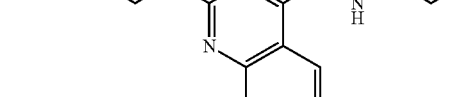 |
| OSM-SMI-27-B8 | 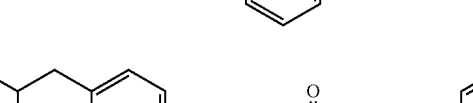 |
| OSM-SMI-27-B9 | 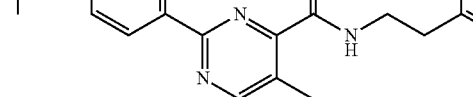 |
| OSM-SMI-27-B10 | 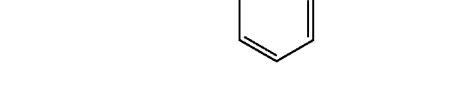 |

TABLE 5-continued

OSM-SMI-27 and compounds based thereupon.

| Compound Number | Compound Structure |
| --- | --- |
| OSM-SMI-27-B11 | 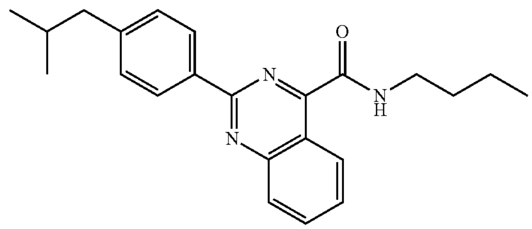 [SMILES: CCCCNC(=O)c1nc(-c2ccc(CC(C)C)cc2)nc2ccccc12] |
| OSM-SMI-27-C0 | 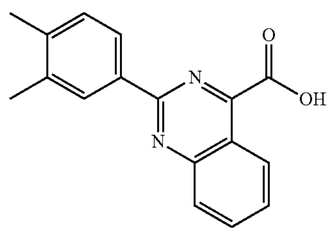 [SMILES: Cc1ccc(-c2nc(C(=O)O)c3ccccc3n2)cc1C] |
| OSM-SMI-27-C1 | 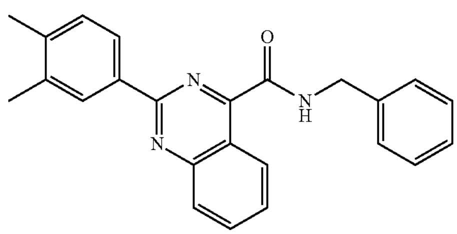 [SMILES: Cc1ccc(-c2nc(C(=O)NCc3ccccc3)c3ccccc3n2)cc1C] |
| OSM-SMI-27-C2 | 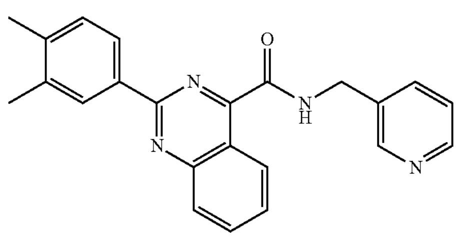 [SMILES: Cc1ccc(-c2nc(C(=O)NCc3cccnc3)c3ccccc3n2)cc1C] |
| OSM-SMI-27-C3 | 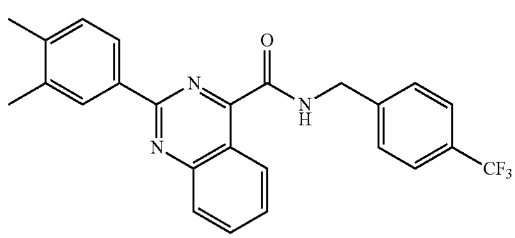 [SMILES: Cc1ccc(-c2nc(C(=O)NCc3ccc(C(F)(F)F)cc3)c3ccccc3n2)cc1C] |
| OSM-SMI-27-C4 | 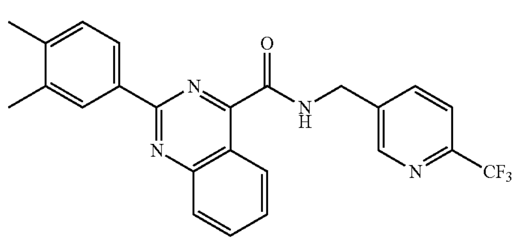 [SMILES: Cc1ccc(-c2nc(C(=O)NCc3ccc(C(F)(F)F)nc3)c3ccccc3n2)cc1C] |

TABLE 5-continued

OSM-SMI-27 and compounds based thereupon.

| Compound Number | Compound Structure |
| --- | --- |
| OSM-SMI-27-C5 | 2-(3,4-dimethylphenyl)-N-phenylquinazoline-4-carboxamide |
| OSM-SMI-27-C6 | 2-(4-isobutylphenyl)-N-(4-(trifluoromethyl)phenyl)quinazoline-4-carboxamide |
| OSM-SMI-27-C7 | 2-(3,4-dimethylphenyl)-N-phenethylquinazoline-4-carboxamide |
| OSM-SMI-27-C8 | 2-(3,4-dimethylphenyl)-N-(4-(trifluoromethyl)phenethyl)quinazoline-4-carboxamide |
| OSM-SMI-27-C9 | 2-(3,4-dimethylphenyl)-6-(trifluoromethyl)-N-(4-(trifluoromethyl)benzyl)quinazoline-4-carboxamide |
| OSM-SMI-27-C10 | 2-(3,4-dimethylphenyl)-N-phenyl-6-(trifluoromethyl)quinazoline-4-carboxamide |

TABLE 5-continued

OSM-SMI-27 and compounds based thereupon.

| Compound Number | Compound Structure |
|---|---|
| OSM-SMI-27-C11 | |
| OSM-SMI-27-Z1<br>Previously<br>OSM-SMI-27 | |
| OSM-SMI-27-Y1<br>Previously<br>OSM-SMI-27Z-1 | |
| OSM-SMI-27-Y2<br>Previously<br>OSM-SMI-27Z-2 | |
| OSM-SMI-27-X1<br>Previously<br>OSM-SMI-27A-1 | |

TABLE 5-continued
OSM-SMI-27 and compounds based thereupon.
| Compound Number | Compound Structure |
| --- | --- |
| OSM-SMI-27-X2<br>Previously<br>OSM-SMI-27A-2 | 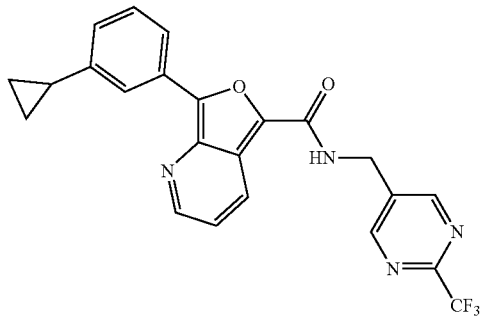 [SMILES: O=C(NCc1cnc(C(F)(F)F)nc1)c1oc(-c2cccc(C3CC3)c2)c2ncccc12] |
| OSM-SMI-27-X3<br>Previously<br>OSM-SMI-27A-3 | 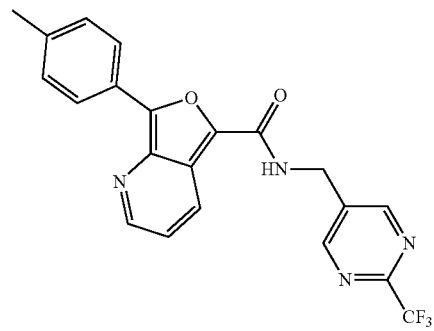 [SMILES: Cc1ccc(-c2oc(C(=O)NCc3cnc(C(F)(F)F)nc3)c3cccnc23)cc1] |
| OSM-SMI-27-X4<br>Previously<br>OSM-SMI-27A-4 | 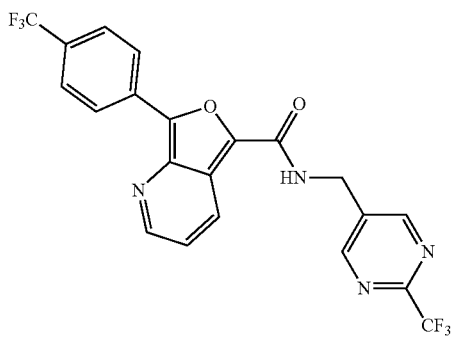 [SMILES: O=C(NCc1cnc(C(F)(F)F)nc1)c1oc(-c2ccc(C(F)(F)F)cc2)c2ncccc12] |
| OSM-SMI-27-W1<br>Previously<br>OSM-SMI-27B-1 | 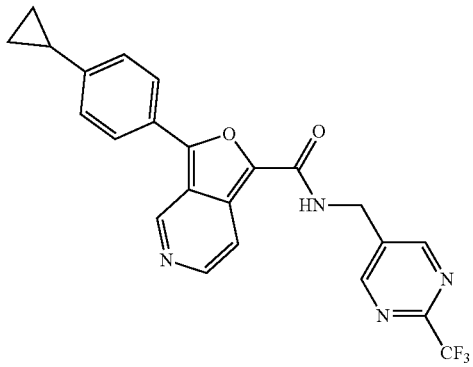 [SMILES: O=C(NCc1cnc(C(F)(F)F)nc1)c1oc(-c2ccc(C3CC3)cc2)c2cnccc12] |

TABLE 5-continued
OSM-SMI-27 and compounds based thereupon.
| Compound Number | Compound Structure |
|---|---|
| OSM-SMI-27-W2<br>Previously<br>OSM-SMI-27B-2 | 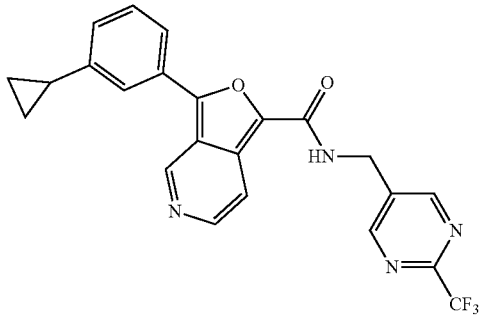 |
| OSM-SMI-27-W3<br>Previously<br>OSM-SMI-27C-1 | 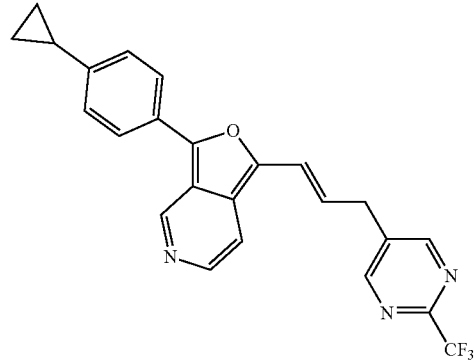 [SMILES: FC(F)(F)c1ncc(C/C=C/c2oc(-c3ccc(C4CC4)cc3)c3cnccc23)cn1] |
| OSM-SMI-27-W4<br>Previously<br>OSM-SMI-27C-2 | 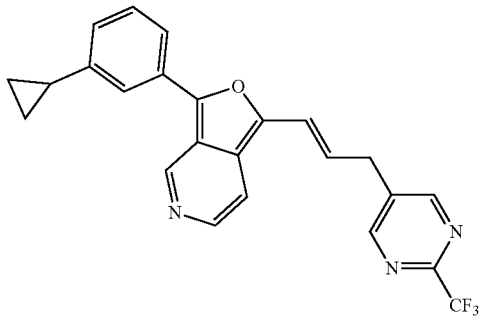 [SMILES: FC(F)(F)c1ncc(C/C=C/c2oc(-c3cccc(C4CC4)c3)c3cnccc23)cn1] |
| OSM-SMI-27-W5<br>Previously<br>OSM-SMI-27C-3 | 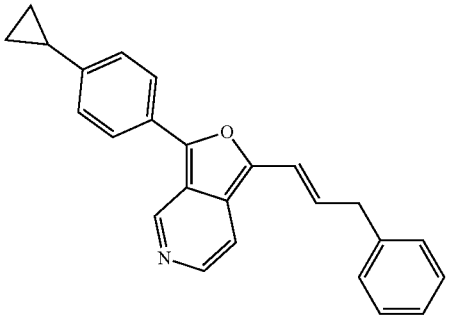 [SMILES: C(=C\c1oc(-c2ccc(C3CC3)cc2)c2cnccc12)/Cc1ccccc1] |

TABLE 5-continued
OSM-SMI-27 and compounds based thereupon.
| Compound Number | Compound Structure |
|---|---|
| OSM-SMI-27-W6<br>Previously<br>OSM-SMI-27C-4 | 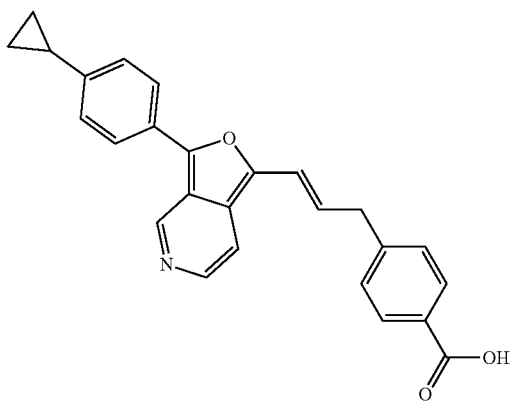 [SMILES: O=C(O)c1ccc(C/C=C/c2oc(-c3ccc(C4CC4)cc3)c3cnccc23)cc1] |
| OSM-SMI-27-V1<br>Previously<br>OSM-SMI-27D-1 | 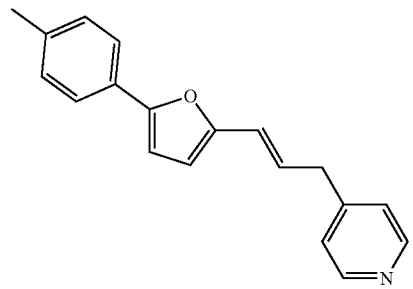 [SMILES: Cc1ccc(-c2ccc(/C=C/Cc3ccncc3)o2)cc1] |
| OSM-SMI-27-V2<br>Previously<br>OSM-SMI-27E-1 | 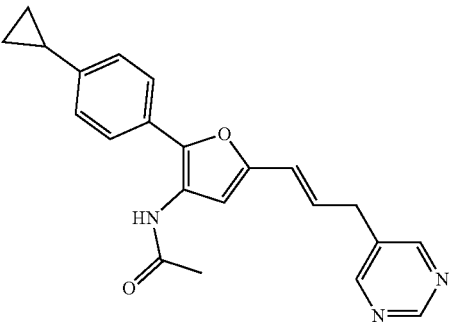 [SMILES: CC(=O)Nc1cc(/C=C/Cc2cncnc2)oc1-c1ccc(C2CC2)cc1] |
| OSM-SMI-27-V3<br>Previously<br>OSM-SMI-27E-2 | 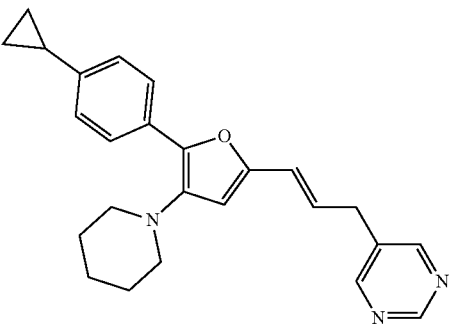 [SMILES: C(=C\c1cc(N2CCCCC2)c(-c2ccc(C3CC3)cc2)o1)/Cc1cncnc1] |

TABLE 5-continued

OSM-SMI-27 and compounds based thereupon.

| Compound Number | Compound Structure |
| --- | --- |
| OSM-SMI-27-V4<br>Previously<br>OSM-SMI-27E-3 | |
| OSM-SMI-27-V5<br>Previously<br>OSM-SMI-27E-4 | |
| OSM-SMI-27-V6<br>Previously<br>OSM-SMI-27F-1 | |
| OSM-SMI-27-U1<br>Previously<br>OSM-SMI-27G-1 | |

TABLE 5-continued
OSM-SMI-27 and compounds based thereupon.
| Compound Number | Compound Structure |
|---|---|
| OSM-SMI-27-U2<br>Previously<br>OSM-SMI-27G-2 | 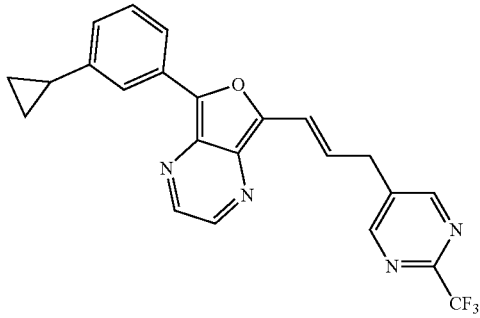 [SMILES: FC(F)(F)c1ncc(C/C=C/c2oc(-c3cccc(C4CC4)c3)c3nccnc23)cn1] |
| OSM-SMI-27-U3<br>Previously<br>OSM-SMI-27H-1 | 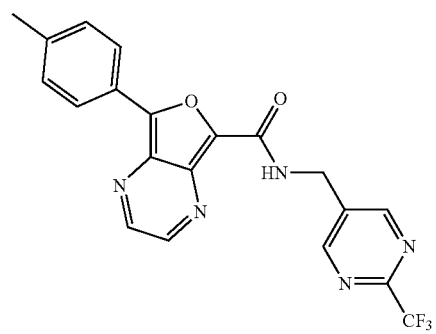 [SMILES: Cc1ccc(-c2oc(C(=O)NCc3cnc(C(F)(F)F)nc3)c3nccnc23)cc1] |
| OSM-SMI-27-U4<br>Previously<br>OSM-SMI-27H-2 | 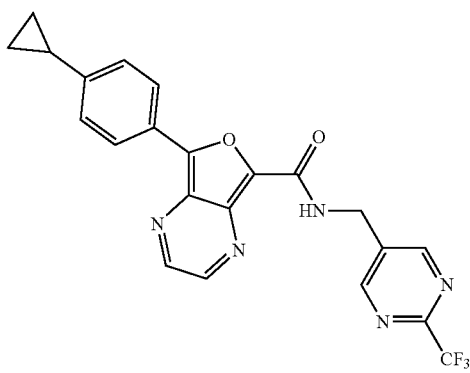 [SMILES: O=C(NCc1cnc(C(F)(F)F)nc1)c1oc(-c2ccc(C3CC3)cc2)c2nccnc12] |
| OSM-SMI-27-T1<br>Previously<br>OSM-SMI-27I-1 | 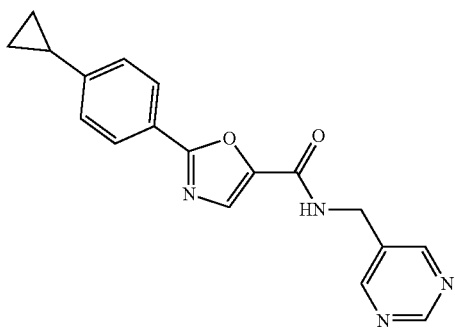 [SMILES: O=C(NCc1cncnc1)c1cnc(-c2ccc(C3CC3)cc2)o1] |

TABLE 5-continued

OSM-SMI-27 and compounds based thereupon.

| Compound Number | Compound Structure |
|---|---|
| OSM-SMI-27-T2<br>Previously<br>OSM-SMI-27I-2 | (structure) |
| OSM-SMI-27-T3<br>Previously<br>OSM-SMI-27J-1 | (structure) |
| OSM-SMI-27-T4<br>Previously<br>OSM-SMI-27K-1 | (structure) |

B. OSM Antibodies

The term "antibody" is used in the broadest-sense and includes fully assembled antibodies, monoclonal antibodies, polyclonal antibodies, multispecific antibodies (e.g., bispecific antibodies), antibody fragments that can bind antigen (e.g., Fab', F'(ab)2, Fv, single chain antibodies, diabodies), and recombinant peptides comprising the forgoing as long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that are typically include different antibodies directed against different determinants (epitopes), each monoclonal antibody is directed against a single determinant on the antigen. In addition to their specificity, the monoclonal antibodies are advantageous in that they are synthesized by the homogeneous culture, uncontaminated by other immunoglobulins with different specificities and characteristics.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 [1975], or may be made by recombinant DNA methods (see, e.g., U.S. Pat. No. 4,816,567). The "monoclonal antibodies" may also be isolated from phage antibody libraries using the techniques described in Clackson et al., Nature, 352:624628[1991] end Marks et al., J. Mol. Biol., 222.1581-597 (1991), for example. Depending on the amino acid sequence of the constant domain of their heavy chains, immunoglobulins can be assigned to different classes. There are five major classes, IgA, IgD, IgE, IgG and IgM, and several of these may be further divided into subclasses or isotypes, e.g. IgG1, IgG2, IgG3, IgG4, IgA1 and IgA2. The heavy-chain constant domains that correspond to the different classes of immunoglobulins are called alpha, delta, epsilon, gamma- and mu respectively. The subunit structures and three-dimensional configurations of different classes of immunoglobulins are well known. Different isotypes have different effector functions; for example, IgG1 and IgG3 isotypes have ADCC activity.

In certain embodiments, the monoclonal, human, humanized, Human Engineered™ or variant anti-OSM antibody is an antibody fragment, such as an RX1, 5H4, MC1, or MC3 antibody fragment. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science 229:81 (1985)). However, these fragments can now be produced directly by recombinant host cells. Better et al., Science 240: 1041-1043 (1988) disclose secretion of functional antibody fragments from bacteria (see, e.g., Better et al., Skerra et al., Science 240: 1038-1041 (1988)). For example, Fab'-SH fragments can be directly recovered from E. coli and chemically coupled to form F(ab')2 fragments (Carter et al., Bio/Technology 10:163-167 (1992)). In another embodiment, the F(ab')2 is formed using the leucine zipper GCN4 to promote assembly of the F(ab')2 molecule. According to another approach, Fv, Fab or F(ab')2 fragments can be isolated directly from recombinant host cell culture. Other techniques for the production of antibody fragments will be apparent to the skilled practitioner.

An "isolated" antibody is one that has been identified and separated and for recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

For a detailed description of the structure and generation of antibodies, see Roth, D. B., and Craig, N. L., Cell, 94:411-414 (1998), and U.S. Pat. No. 6,255,458, herein incorporated by reference in its entirety. Briefly, the process for generating DNA encoding the heavy and light chain immunoglobulin genes occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged heavy and light immunoglobulin genes. This gene segment rearrangement process appears to be sequential. First, heavy chain D-to-J joints are made, followed by heavy chain V-to-DJ joints and light chain V-to-J joints.

As provided herein, the compositions for and methods of treating or preventing tumor cell detachment, proliferation and/or metastasis may utilize one or more antibody used singularly or in combination with other therapeutics to achieve the desired effects. Antibodies according to the present invention may be isolated from an animal producing the antibody as a result of either direct contact with an environmental antigen or immunization with the antigen. Alternatively, antibodies may be produced by recombinant DNA methodology using one of the antibody expression systems well known in the art (See, e.g., Harlow and Lane, Antibodies: A Laboratory Manual, Cold Spring Harbor Laboratory (1988)). Such antibodies may include recombinant IGs, chimeric fusion-proteins having immunoglobulin derived sequences or "Human Engineered" antibodies that may all be used for the treatment and prevention of tumor cell detachment, proliferation and/or metastasis according to the present invention. In addition to intact, full-length molecules, the term "antibody" also refers to fragments thereof (such as, e.g., scFv, Fv, Fd, Fab, Fab' and F(ab)'2 fragments) or multimers or aggregates of intact molecules and/or fragments that bind to OSM (or OSMR). These antibody fragments bind antigen and may be derivatized to exhibit structural features that facilitate clearance and uptake, e.g., by incorporation of galactose residues.

In one embodiment of the present invention, OSM monoclonal antibodies may be prepared essentially as described in Halenbeck et al. U.S. Pat. No. 5,491,065 (1997), incorporated herein by reference. Exemplary OSM monoclonal antibodies include those that bind to an apparent conformational epitope associated with recombinant or native dimeric OSM with concomitant neutralization of biological activity. These antibodies are substantially unreactive with biologically inactive forms of OSM including monomeric and chemically derivatized dimeric OSM.

In other embodiments of the present invention, Human Engineered anti-OSM monoclonal antibodies are provided. The phrase "Human Engineered antibody" refers to an antibody derived from a non-human antibody, typically a mouse monoclonal antibody. Alternatively, a Human Engineered antibody may be derived from a chimeric antibody that retains or substantially retains the antigen binding properties of the parental, non-human, antibody but which exhibits diminished immunogenicity as compared to the parental antibody when administered to humans. The phrase "chimeric antibody," as used herein, refers to an antibody containing sequence derived from two different antibodies (see, e.g., U.S. Pat. No. 4,816,567) which typically originate from different species. Most typically, chimeric antibodies comprise human and murine antibody fragments, generally human constant and mouse variable regions.

The phrase "complementarity determining region" or the term "CDR" refers to amino acid sequences which together define the binding affinity and specificity of the natural Fv region of a native immunoglobulin binding site (See, e.g., Chothia et al., J. Mol. Biol. 196:901 917 (1987); Kabat et al., U.S. Dept. of Health and Human Services NIH Publication No. 91 3242 (1991)). The phrase "constant region" refers to the portion of the antibody molecule that confers effector functions. In the present invention, mouse constant regions are preferably substituted by human constant regions. The constant regions of the subject antibodies are derived from human immunoglobulins. The heavy chain constant region can be selected from any of the five isotypes: alpha, delta, epsilon, gamma or mu.

The antibodies of the present invention are said to be immunospecific or specifically binding if they bind to antigen with a Ka of greater than or equal to about 106M-1 preferably greater than or equal to about $10^7 M^{-1}$, more preferably greater than or equal to about 108M-1, and most preferably greater than or equal to about 109M-1, 1010M-1, 1011M-1 or 1012M-1. The anti-OSM antibodies may bind to different naturally occurring forms of OSM, including those expressed by the host's/subject's tissues as well as that expressed by the tumor. The monoclonal antibodies disclosed herein, such as RX1, 5H4, MC1, or MC3 antibody, have affinity for OSM and are characterized by a dissociation equilibrium constant (Kd) of at least 10-4 M, preferably at least about 10-7 M to about 10-8 M, more preferably at least about 108M, 1010M, 10-11M or 10-12M. Such affinities may be readily determined using conventional techniques, such as by equilibrium dialysis; by using the BIAcore 2000 instrument, using general procedures outlined by the manufacturer; by radioimmunoassay using 125I labeled OSM; or by another method known to the skilled artisan. The affinity data may be analyzed, for example, by the method of Scatchard et al., Ann N.Y. Acad. Sci., 51:660 (1949). Thus, it will be apparent that preferred OSM antibodies will exhibit a high degree of specificity for OSM and will bind with substantially lower affinity to other molecules.

The antigen to be used for production of antibodies may be, e.g., intact OSM or a fragment of OSM that retains the desired epitope, optionally fused to another polypeptide that allows the epitope to be displayed in its native conformation. Alternatively, cells expressing OSM at their cell surface can be used to generate antibodies. Such cells can be transformed to express OSM or may be other naturally occurring cells that express OSM. Other forms of OSM useful for generating antibodies will be apparent to those skilled in the art.

Anti-OSM antibodies are known in the art and disclosed in US20130251724 and US20140099315, the disclosures of which are incorporated herein by reference.

C. OSM Muteins

The invention further provides OSM muteins that may be used as OSM antagonists according to the methods of the invention.

"Fragment" as used herein means a portion of the intact native molecule; for example, a fragment polypeptide is a fragment of the native polypeptide in which one or more amino acids from either the N-terminal or C-terminal have been deleted.

"Mutein" as used herein with respect to polypeptides means a variant of the intact native molecule or a variant of a fragment of the native molecule, in which one or more amino acids have been substituted, inserted or deleted. Such substitutions, insertions or deletions can be at the N-terminus, C-terminus or internal to the molecule. Thus the term "muteins" includes within its scope fragments of the native molecule. Insertional muteins include fusions at the N- or C-terminus, e.g. fusion to the Fc portion of an immunoglobulin to increase half-life.

Preferred muteins according to the invention exhibit at least about 65%, 70%. 75%, 80%, 85%, 90%, 95%, 97% or more sequence identity (homology) to the native polypeptide, as determined by the Smith-Waterman homology search algorithm (Meth. Mol. Biol. 70:173-187 (1997)) as implemented in the MSPRCH program (Oxford Molecular) using an affine gap search with the following search parameters: gap open penalty of 12, and gap extension penalty of 1. Other well-known and routinely used homology/identity scanning algorithm programs include Pearson and Lipman, PNAS USA, 85:2444-2448 (1988); Lipman and Pearson, Science, 222:1435 (1985); Devereaux et al., Nuc. Acids Res., 12:387-395 (1984); or the BLASTP, BLASTN or BLASTX algorithms of Altschul, et al., Mol. Biol., 215:403-410 (1990). Computerized programs using these algorithms are also available and include, but are not limited to: GAP, BESTFIT, BLAST, FASTA and TFASTA, which are commercially available from the Genetics Computing Group (GCG) package, Version 8, Madison Wis., USA; and CLUSTAL in the PC/Gene program by Intellegenetics, Mountain View Calif. Preferably, the percentage of sequence identity is determined by using the default parameters determined by the program.

"Modification" as used herein means any modification of the native polypeptide, fragment or mutein, such as glycosylation, phosphorylation, polymer conjugation (such as with polyethylene glycol), or other addition of foreign moieties, so long as the desired activity (agonist or antagonist) is retained.

In yet another embodiment, the OSM mutein comprises one or more of binding sites 1, 2, or 3, or portions thereof involved in receptor-binding, alone or fused to other polypeptides that allow display of the fragments in proper three-dimensional conformation.

Muteins containing any desired conservative and/or non-conservative muteins are readily prepared using techniques well known in the art, including recombinant production or chemical synthesis.

Conservative substitutions, particularly substitutions outside of regions directly involved in ligand-receptor binding, are not expected to significantly change the binding properties of the OSM muteins (or OSMR muteins). Amino acids can be classified according to physical properties and contribution to secondary and tertiary protein structure. A conservative substitution is recognized in the art as a substitution of one amino acid for another amino acid that has similar properties. Exemplary conservative substitutions are set out in Table 2 (from WO 97/09433, page 10, published Mar. 13, 1997 (PCT/GB96/02197, filed Sep. 6, 1996), immediately below.

The availability of a DNA sequence encoding OSM permits the use of various expression systems to produce the desired polypeptides. Construction of expression vectors and recombinant production from the appropriate DNA sequences are performed by methods well known in the art. These techniques and various other techniques are generally performed according to Sambrook et al., Molecular Cloning—A Laboratory Manual, Cold Spring Harbor Laboratory, Cold Spring Harbor, N.Y. (1989), and Kriegler, M., Gene Transfer and Expression, A Laboratory Manual, Stockton Press, New York (1990), both of which are incorporated herein by reference.

Certain modifications to the primary sequence of OSM can be made by deletion, addition, or alteration of the amino acids encoded by the DNA sequence without destroying the desired structure (e.g., the receptor binding ability of OSM) in accordance with well-known recombinant DNA techniques. Further, a skilled artisan will appreciate that individual amino acids may be substituted or modified by oxidation, reduction or other modification, and the polypeptide may be cleaved to obtain fragments that retain the active binding site and structural information. Such substitutions and alterations result in polypeptides having an amino acid sequence which falls within the definition of polypeptide "having substantially the same amino acid sequence" as the mature OSM SEQ ID NO:1 and 2.

Polypeptides may be produced by chemical synthesis or recombinant production techniques known in the art.

The relatedness of proteins can also be characterized through the relatedness of their encoding nucleic acids. Methods to determine identity and/or similarity of polynucleotide sequences are described above. In addition, methods to determine similarity of polynucleotide sequences through testing their ability to hybridize under moderately or highly stringent conditions may be determined as follows. Exemplary moderately stringent hybridization conditions are as follows: hybridization at 42° C. in a hybridization solution comprising 50% formamide, 1% SDS, 1 M NaCl, 10% Dextran sulfate, and washing twice for 30 minutes at 60° C. in a wash solution comprising 0.1×SSC and 1% SDS.

Highly stringent conditions include washes at 68° C. in a wash solution comprising 0.1×SSC and 1% SDS. It is understood in the art that conditions of equivalent stringency can be achieved through variation of temperature and buffer, or salt concentration as described in the art (Ausubel, et al. (Eds.), Protocols in Molecular Biology, John Wiley & Sons (1994), pp. 6.0.3 to 6.4.10). Modifications in hybridization conditions can be empirically determined or precisely calculated based on the length and the percentage of guanosine/cytosine (GC) base pairing of the probe. The hybridization conditions can be calculated as described in Sambrook et al., (Eds.), Molecular Cloning: A Laboratory Manual, Cold Spring Harbor Laboratory Press: Cold Spring Harbor, N.Y. (1989), pp. 9.47 to 9.51.

D. OSM Gene Therapy

Delivery of a therapeutic protein to appropriate cells can be effected via gene therapy ex vivo, in situ, or in vivo by use of any suitable approach known in the art, including by use of physical DNA transfer methods (e.g., liposomes or chemical treatments) or by use of viral vectors (e.g., adenovirus, adeno-associated virus, or a retrovirus). Antisense compounds and methods of using them are also provided by the present invention. The level of OSM or OSMR activity may be reduced by using well-known antisense, gene "knock-out," ribozyme, triple helix or RNAi methods to decrease the level gene expression. Techniques for the production and use of such molecules are well known to those of skill in the art.

As used herein, the term "peptidomimetic" is a non-peptide compound that comprises an assembly of amino acid side chains, or pharmacophores, or suitable derivatives thereof, that are supported on a scaffold such that the spatial orientation of the pharmacophores substantially mimic the bioactive conformation of a natural peptide. For example, a peptidomimetic may lack amino acids or peptide bonds but retain the particular three-dimensional arrangement of peptide chain groups from the parent peptide that is required for binding activity. The scaffold may comprise a bicyclic, tricyclic or higher polycyclic carbon or heteroatom skeleton, or may be based on one or more ring structures (e.g., pyridine, imidazole, etc.) or amide bonds. This scaffold may be linked by spacers to an acidic group (e.g. a carboxylic acid functional group) at one end and a basic group (e.g. an N-containing moiety such as amidine or guanidine) at the other end of the core. Exemplary techniques for synthesizing peptidomimetics are described in U.S. patent application no. 20030199531 published Oct. 23, 2003, U.S. Patent Application No. 20030139348 published Jul. 24, 2003.

In addition to antibodies and other proteins, this invention also contemplates alternative OSM antagonists including, but not limited to, peptides or small organic molecules that are also effective in inhibiting the interaction between OSM and OSMR or the activation of OSMR.

II). Combination Therapy

Concurrent administration of two therapeutic agents according to the present invention, such as an OSM antagonist and a second anti-osteoclast agent, does not require that the agents be administered at the same time or by the same route, as long as there is an overlap in the time period during which the agents are exerting their therapeutic effect. Simultaneous or sequential administration is contemplated, as is administration on different days or weeks.

The discovery of a significant time lag to observe therapeutic effect after commencing treatment with an OSM antibody (an exemplary OSM antagonist) makes desirable the co-administration of a second anti-osteoclast agent with quicker onset of action during this transition period. During the transition period, the two agents must be administered at a monotherapeutically effective amount. Subsequent to the transition period, the second anti-osteoclast agent may be discontinued or reduced in dosage. If the OSM antagonist and second anti-osteoclast agent exert synergistic effects, the dose of one or both may be lowered after the transition period. Compositions of the invention are administered to a mammal already suffering from, or predisposed to, cancer and associated tumor cell detachment, proliferation and/or metastasis, in an amount sufficient to prevent or at least partially arrest the development of such disease. An amount of a therapeutic agent adequate to accomplish this when the therapeutic agent is given alone (not in combination with a second therapeutic agent) is defined as a "monotherapeutically effective dose."

In the combination therapy methods of the present invention, the OSM antagonist, such as the OSM antibody, and the second anti-osteoclast agent may be administered simultaneously or at different time. The two agents can be administered, for example, within 8 hours, 1 day, 14 days, 30 days, 3 months, 6 months, 9 months or 1 year of each other.

Exemplary second anti-osteoclast agents include bisphosphonates, including but not limited to zoledronate, pamidronate, clodronate, etidronate, tiludronate, alendronate, ibandronate or risedronate. Exemplary other anti-osteoclast agents include bisphosphonates, PTHrP neutralizing agents (e.g., antibody, antisense, siRNA), cathepsin K inhibitors, MIP-1-á antagonists, RANK/RANKL neutralizing agents (e.g., anti-RANK antibody, such as AMG-162, or antisense, soluble RANKL receptor or muteins thereof), RANKL vaccine, osteoprotegrin (OPG), platelet-derived growth factors (PDGF), src kinase inhibitors, gallium maltolate, and matrix metalloproteinase (MMP) inhibitors.

Exemplary doses of bisphosphonates include the intravenous administration of 4 mg. Lesser dosages may also be administered including 3.5 mg, 3.3 mg or 3.0 mg. Other routes of administration are possible including subcutaneous and as described in WO 02/087555. Effective amounts of a OSM antibody will vary and depend on the severity of the disease and the weight and general state of the patient being treated, but generally range from about 1.0 mg/kg to about 100 mg/kg body weight, or about 10 mg/kg to about 30 mg/kg, with dosages of from about 0.1 mg/kg to about 10 mg/kg or about 1 mg/kg to about 10 mg/kg per application being more commonly used. For example, about 10 mg/kg to 5 mg/kg or about 30 mg/kg to 1 mg/kg of antibody is an initial candidate dosage for administration to the patient, whether, for example, by one or more separate administrations, or by continuous infusion. Administration is daily, on alternating days, weekly or less frequently, as necessary depending on the response to the disease and the patient's tolerance of the therapy. Maintenance dosages over a longer period of time, such as 4, 5, 6, 7, 8, 10 or 12 weeks or longer may be needed until a desired suppression of disease symptoms occurs, and dosages may be adjusted as necessary. The progress of this therapy is easily monitored by conventional techniques and assays.

Although the methods of the present invention may be useful for all stages of cancers, they may be particularly appropriate in advanced or metastatic cancers. Combining the therapy method with a chemotherapeutic or radiation regimen may be preferred in patients that have not received chemotherapeutic treatment, whereas treatment with the therapy method of the present invention may be indicated for patients who have received one or more chemotherapies. Additionally, the therapy methods of the present invention can also enable the use of reduced dosages of concomitant chemotherapy, particularly in patients that do not tolerate the toxicity of the chemotherapeutic agent very well.

The method of the invention contemplates the administration of single anti-OSM antibodies, as well as combinations, or "cocktails", of different antibodies. Such antibody cocktails may have certain advantages in as much as they contain antibodies which exploit different effector mechanisms or combine directly cytotoxic antibodies with antibodies that rely on immune effector functionality. Such antibodies in combination may exhibit synergistic therapeutic effects.

The methods of the invention can be used in combination with yet other therapeutics, such as cancer therapeutics. Exemplary cancer therapeutic agents and/or procedures, include but are not limited to various chemotherapeutic agents, androgen-blockers, and immune modulators (e.g., IL-2, GOSM, SLC), Bisphosphonate(s) (e.g., Aredia (i.e., pamidronate, pamidronic acid, disodium pamidronate, pamidronate disodium pentahydrate); Zometa (i.e., Aclasta, zoledronic acid, zoledronate); Clondronate (i.e., Bonefos, Loron, clodronate disodium, sodium clondronate); Fosamax (i.e., alendronate, alendronate sodium salt trihydrate, alendronic acid); Fosavance (i.e., Fosamax formulated with vitamin D); Bondronat or Bonviva or Boniva (i.e., ibandronate, ibandronic acid, ibandronate sodium); Actonel (i.e., risedronate, risedronate sodium, risendronic acid); Didronel or Didrocal (i.e., etidronate, etidronic acid, etidronate disodium); Nerixia (i.e., neridronate, neridronic acid); Skelid (i.e., tiludronate, tiludronic acid); dimethyl-APD (i.e., olpadronate, olpadronic acid); and medronic acid or medronate), surgery, radiation, cytotoxic chemotherapy, hormone therapy (e.g., Tamoxifen; anti-Androgen therapy), antibody therapy (e.g., antibodies to RANKL/RANK neutralizing; PTHrP neutralizing, anti-Her2, anti-CD20, anti-CD40, CD22, VEGF, IGFR-1, EphA2, HAAH, TMEFF2, CAIX antibodies), therapeutic protein therapy (e.g., soluble RANKL receptor; OPG, and PDGF and MMP inhibitors), small molecule drug therapy (e.g., Src-kinase inhibitor), kinase inhibitors of growth factor receptors, or RANKL inhibitors, oligonucleotides therapy (e.g., RANKL or RANK or PTHrP Anti-sense), gene therapy (e.g. RANKL or RANK inhibitors, such as anti-RANKL antibodies), peptide therapy (e.g. muteins of RANKL) as well as those proteins, peptides, compounds, and small molecules described herein.

Cancer chemotherapeutic agents include, without limitation, alkylating agents, such as carboplatin and cisplatin; nitrogen mustard alkylating agents; nitrosourea alkylating agents, such as carmustine (BCNU); antimetabolites, such as methotrexate; folinic acid; purine analog antimetabolites, mercaptopurine; pyrimidine analog antimetabolites, such as fluorouracil (5-FU) and gemcitabine (Gemzar®); hormonal antineoplastics, such as goserelin, leuprolide, and tamoxifen; natural antineoplastics, such as aldesleukin, interleukin-2, docetaxel, eloposide (VP-16), interferon alfa, paclitaxel (Taxol®), and tretinoin (ATRA); antibiotic natural antineoplastics, such as bleomycin, dactinomycin, daunorubicin, doxorubicin, daunomycin and mitomycins including mitomycin C; and vinca alkaloid natural antineoplastics, such as vinblastine, vincristine, vindesine; hydroxyurea; aceglatone, adriamycin, ifosfamide, enocitabine, epitiostanol, aclarubicin, ancitabine, nimustine, procarbazine hydrochloride, carboquone, carboplatin, carmofur, chromomycin A3, antitumor polysaccharides, antitumor platelet factors, cyclophosphamide (Cytoxin®); Schizophyllan, Cytarabine® (cytosine arabinoside), dacarbazine, thioinosine, thiotepa, tegafur, dolastatins, dolastatin analogs such as auristatin, CPT-11 (irinotecan), mitozantrone, vinorelbine, teniposide, aminopterin, caminomycin, esperamicins (See, e.g., U.S. Pat. No. 4,675,187), neocarzinostatin, OK-432, bleomycin, furtulon, broxuridine, busulfan, honvan, peplomycin, bestatin (Ubenimex®), interferon-0, mepitiostane, mitobronitol, melphalan, laminin peptides, lentinan, *Coriolus versicolor* extract, tegafur/uracil, estramustine (estrogen/mechlorethamine).

Further, additional agents used as therapy for cancer patients include EPO, G-CSF, ganciclovir; antibiotics, leuprolide; meperidine; zidovudine (AZT); interleukins 1 through 18, including mutants and analogues; interferons or cytokines, such as interferons α, β, and γ hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α & (3); invasion inhibiting factor-2 (IIF-2); bone morphogenetic proteins 1-7 (BMP 1-7); somatostatin; thymosin-α-1; γ-globulin; superoxide dismutase (SOD); complement factors; anti-angiogenesis factors: antigenic materials; and pro-drugs.

Prodrug refers to a precursor or derivative form of a pharmaceutically active substance that is less cytotoxic or non-cytotoxic to tumor cells compared to the parent drug and is capable of being enzymatically activated or converted into an active or the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use herein include, but are not limited to, those chemotherapeutic agents described above.

III). Compositions Comprising OSM Antagonists

Compositions for inhibiting or reducing tumor cell detachment, proliferation and/or metastasis are provided. Preferred compositions are those that interfere, inhibit, reduce or block OSM protein function. In one embodiment the composition includes an antagonist of OSM, or its target gp130 or a combination thereof. A preferred OSM protein antagonist includes but is not limited to a small molecule that sterically interacts with binding site 1 of OSM.

Other embodiments provide compositions for inhibiting or reducing OSM activity, such as antibodies which bind and thus inhibit OSM activity, proteins, muteins, and/or nucleic acid compositions which may interfere with OSM production or may encode antibodies and other protein inhibitors themselves.

Another embodiment is directed to compositions comprising an OSM antagonist in an amount effective to inhibit OSM activity relative to a control. It will be appreciated that a control includes cells or organisms that are not treated with the disclosed compositions.

In another embodiment, the disclosed OSM protein antagonists selectively interact with a region disclosed herein as active site 1 of the OSM protein.

The compositions are administered to an individual in need of treatment or prophylaxis of at least one symptom or manifestation (since disease can occur/progress in the absence of symptoms) of cancer or cellular hyperproliferation. In one embodiment, the compositions are administered in an effective amount to inhibit OSM mediated cellular activity and thereby inhibit or reduce tumor cell detachment, proliferation and/or metastasis. The amount of inhibition can be determined relative to a control, for example cells that are not treated with the inhibitor. Methods for measuring inhibition OSM activity are provided in the Examples.

A. Formulations

The compounds are preferably employed for therapeutic uses in combination with a suitable pharmaceutical carrier. Such compositions include an effective amount of the compound, and a pharmaceutically acceptable carrier or excipient. The formulation is made to suit the mode of administration. Pharmaceutically acceptable carriers are determined in part by the particular composition being administered, as well as by the particular method used to administer the composition. Accordingly, there is a wide variety of suitable formulations of pharmaceutical compositions containing the nucleic acids some of which are described herein. The compounds may be in a formulation for administration topically, locally or systemically in a suitable pharmaceutical carrier. Remington's Pharmaceutical Sciences, 15th Edition by E. W. Martin (Mark Publishing Company, 1975), discloses typical carriers and methods of preparation. The compound may also be encapsulated in suitable biocompatible microcapsules, microparticles or microspheres formed of biodegradable or non-biodegradable polymers or proteins or liposomes for targeting to cells. Such systems are well known to those skilled in the art and may be optimized for use with the appropriate nucleic acid.

Formulations for topical administration may include ointments, lotions, creams, gels, drops, suppositories, sprays, liquids and powders. Conventional pharmaceutical carriers, aqueous, powder or oily bases, or thickeners can be used as desired.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions, solutions or emulsions that can include suspending agents, solubilizers, thickening agents, dispersing agents, stabilizers, and preservatives. Formulations for injection may be presented in unit dosage form, e.g., in ampules or in multi-dose containers, with an added preservative.

Preparations include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation can be found in Remington's Pharmaceutical Sciences, Mack Publishing Co., Easton, Pa. Those of skill in the art can readily determine the various parameters for preparing and formulating the compositions without resort to undue experimentation.

The compound alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like. For administration by inhalation, the compounds are conveniently delivered in the form of an aerosol spray presentation from pressurized packs or a nebulizer, with the use of a suitable propellant.

In some embodiments, the compound described above may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers. In one embodiment, the compounds are conjugated to lipophilic groups like cholesterol and lauric and lithocholic acid derivatives with C32 functionality to improve cellular uptake. For example, cholesterol has been demonstrated to enhance uptake and serum stability of siRNA in vitro (Lorenz, et al., Bioorg. Med. Chem. Lett. 14(19):4975-4977 (2004)) and in viva (Soutschek, et al., Nature 432 (7014):173-178 (2004)). Other groups that can be attached or conjugated to the compounds described above to increase cellular uptake, include acridine derivatives; cross-linkers such as psoralen derivatives, azidophenacyl, proflavin, and azidoproflavin; artificial endonucleases; metal complexes such as EDTA-Fe(II) and porphyrin-Fe(II); alkylating moieties; enzymes such as alkaline phosphatase; terminal transferases; abzymes; cholesteryl moieties; lipophilic carriers; peptide conjugates; long chain alcohols; phosphate esters; radioactive markers; non-radioactive markers; carbohydrates; and polylysine or other polyamines. U.S. Pat. No. 6,919,208 to Levy, et al., also described methods for enhanced delivery. These pharmaceutical formulations may be manufactured in a manner that is itself known, e.g., by means of conventional mixing, dissolving, granulating, levigating, emulsifying, encapsulating, entrapping or lyophilizing processes.

B. Methods of Administration

In general, methods of administering compounds are well known in the art. The compositions can be administered by a number of routes including, but not limited to: oral, intravenous, intraperitoneal, intramuscular, transdermal, subcutaneous, topical, sublingual, or rectal means. Compounds can also be administered via liposomes. Such administration routes and appropriate formulations are generally known to those of skill in the art.

Administration of the formulations described herein may be accomplished by any acceptable method which allows the compounds to reach its target. The particular mode selected will depend of course, upon factors such as the particular formulation, the severity of the state of the subject being treated, and the dosage required for therapeutic efficacy. As generally used herein, an "effective amount" is that amount which is able to treat one or more symptoms of age related disorder, reverse the progression of one or more symptoms of age related disorder, halt the progression of one or more symptoms of age related disorder, or prevent the occurrence of one or more symptoms of age related disorder in a subject to whom the formulation is administered, as compared to a matched subject not receiving the compound. The actual effective amounts of compound can vary according to the specific compound or combination thereof being utilized, the particular composition formulated, the mode of administration, and the age, weight, condition of the individual, and severity of the symptoms or condition being treated. Any acceptable method known to one of ordinary skill in the art may be used to administer a formulation to the subject. The administration may be localized (i.e., to a particular region, physiological system, tissue, organ, or cell type) or systemic, depending on the condition being treated.

Injections can be e.g., intravenous, intradermal, subcutaneous, intramuscular, or intraperitoneal. The composition can be injected intradermally for treatment or prevention of age related disorder, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

The formulations may be delivered using a bioerodible implant by way of diffusion or by degradation of the polymeric matrix. In certain embodiments, the administration of the formulation may be designed so as to result in sequential exposures to the active agent over a certain time period, for example, hours, days, weeks, months or years. This may be accomplished, for example, by repeated administrations of a formulation or by a sustained or controlled release delivery system in which the active agent is delivered over a prolonged period without repeated administrations. Administration of the formulations using such a delivery system may be, for example, by oral dosage forms, bolus injections, transdermal patches or subcutaneous implants. Maintaining a substantially constant concentration of the composition may be preferred in some cases.

Other delivery systems suitable include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include erosional systems in which the OSM protein antagonist is contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133, 974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the OSM protein antagonist. In addition, a pump-based hardware delivery system may be used to deliver one or more embodiments.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

C. Effective Dosages

Dosages for a particular individual can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to an individual is sufficient to effect a beneficial therapeutic response in the individual over time, or, e.g., to reduce symptoms, or other appropriate activity, depending on the application. The dose is determined by the efficacy of the particular formulation, and the activity, stability or serum half-life of the OSM protein antagonist employed and the condition of the individual, as well as the body weight or surface area of the individual to be treated. The size of the dose is also determined by the existence, nature, and extent of any adverse side-effects that accompany the administration of a particular vector, formulation, or the like in a particular individual.

Formulations are administered at a rate determined by the LD50 of the relevant formulation, and/or observation of any side-effects of the compositions at various concentrations, e.g., as applied to the mass and overall health of the individual. Administration can be accomplished via single or divided doses.

In vitro models can be used to determine the effective doses of the compositions as a potential cancer treatment, as described in the examples. In determining the effective amount of the compound to be administered in the treatment or prophylaxis of disease the physician evaluates circulating plasma levels, formulation toxicities, and progression of the disease. For the disclosed compositions, the dose administered to a 70 kilogram individual is typically in the range equivalent to dosages of currently-used therapeutic antibodies such as Avastin®, Erbitux® and Herceptin®.

The formulations described herein can supplement treatment conditions by any known conventional therapy, including, but not limited to, antibody administration, vaccine administration, administration of cytotoxic agents, natural amino acid polypeptides, nucleic acids, nucleotide analogues, and biologic response modifiers. Two or more combined compounds may be used together or sequentially. For example, the compositions can also be administered in therapeutically effective amounts as a portion of an anti-cancer cocktail. Anti-cancer cocktails can include therapeutics to treat cancer or angiogenesis of tumors.

IV). Methods of Treatment

The disclosed compositions can be administered to a subject in need thereof to treat, alleviate, or reduce one or more symptoms associated with cancer or other forms of cellular hyperproliferation. The compositions can be administered locally or systemically to inhibit tumor cell detachment, proliferation and/or metastasis. The types of cancer that can be treated with the provided compositions and methods include, but are not limited to, the following: bladder, brain, breast, cervical, colorectal, esophageal, kidney, liver, lung, nasopharangeal, pancreatic, prostate, skin, stomach, uterine, ovarian, and testicular. In a preferred embodiment the cancer is prostate or breast cancer. Administration is not limited to the treatment of an existing tumor but can also be used to prevent or lower the risk of developing such diseases in an individual, i.e., for prophylactic use. Potential candidates for treatment include individuals with a high risk of developing cancer, i.e., with a personal or familial history of certain types of cancer.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

In one embodiment, the subject is subjected to primary surgery related to the cancer. In another embodiment, administering the pharmaceutical formulation takes place before, during or after the primary surgery. In yet another embodiment, the cancer comprises a solid cancer. In yet another embodiment, the solid cancer is selected from the group consisting of breast cancer and prostate cancer.

V). Methods for Screening for Inhibitors of Tumor Cell Detachment, Proliferation and Metastasis Methods for identifying inhibitors of tumor cell detachment, proliferation and/or metastasis are provided and utilize well known techniques and reagents. The inhibitor reduces, inhibits, blocks, or interferes with OSM protein function, expression, or bioavailability.

In some embodiments, the assays can include random screening of large libraries of test compounds. The test compounds are, in a preferred embodiment, non-protein small molecule. The term "small molecule" refers to compounds less than 1,000 daltons, typically less than 500 daltons. Alternatively, the assays may be used to focus on particular classes of compounds suspected of inhibiting OSM activity in cells, tissues, organs, or systems.

Assays can include determinations of OSM protein expression, protein expression, protein activity, signal transduction, or binding activity. Other assays can include determinations of OSM protein nucleic acid transcription or translation, for example mRNA levels, mRNA stability, mRNA degradation, transcription rates, and translation rates.

In one embodiment, the identification of an inhibitor of tumor cell detachment, proliferation and/or metastasis is based on the function of OSM in the presence and absence of a test compound. The test compound or modulator can be any substance that alters or is believed to alter the function of OSM. Typically, an inhibitor will be selected that reduces, eliminates, or inhibits OSM and the OSM initiated regulatory pathway.

One exemplary method includes contacting OSM protein with at least a first test compound and assaying for an interaction between OSM protein and the first test compound with an assay. The assaying can include determining inhibition of OSM interaction with gp-130. Specific assay endpoints or interactions that may be measured in the disclosed embodiments include assaying for OSM, modulation, down or up regulation or turnover. These assay endpoints may be assayed using standard methods such as FACS, FACE, ELISA, Northern blotting and/or Western blotting. Moreover, the assays can be conducted in cell free systems, in isolated cells, genetically engineered cells, immortalized cells, or in organisms such as transgenic animals.

Other screening methods include using labeled OSM protein to identify a test compound. OSM can be labeled using standard labeling procedures that are well known and used in the art. Such labels include, but are not limited to, radioactive, fluorescent, biological and enzymatic tags.

Another embodiment provides a method for identifying an inhibitor of tumor cell detachment, proliferation and/or metastasis by determining the effect a test compound has OSM activity. For example, isolated cells or whole organisms expressing OSM or both can be contacted with a test compound. OSM activity can be determined using standard biochemical techniques such as immunodetection. Suitable cells for this assay include, but are not limited to, cancer cells, immortalized cell lines, primary cell culture, or cells engineered to express OSM proteins, for example cells from mammals such as humans. Compounds that inhibit OSM activity can be selected.

Another embodiment provides for in vitro assays for the identification of inhibitors of tumor cell detachment, proliferation and/or metastasis. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. Such a molecule can bind to OSM protein and inhibit its biological functions. The binding of a molecule to a target may, in and of itself, be inhibitory, due to steric, allosteric or charge-charge interactions or inactivation of OSM protein. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods. Other embodiments include methods of screening compounds for their ability to inhibit the function of OSM proteins. Various cell lines can be utilized for such screening assays, including cells specifically engineered for this purpose. Furthermore, those of skill in the art will appreciate that stable or transient transfections, which are well known and used in the art, may be used in the disclosed embodiments.

For example, a transgenic cell comprising an expression vector can be generated by introducing the expression vector into the cell. The introduction of DNA into a cell or a host cell is well known technology in the field of molecular biology and is described, for example, in Sambrook et al., Molecular Cloning 3rd Ed. (2001). Methods of transfection of cells include calcium phosphate precipitation, liposome mediated transfection, DEAE dextran mediated transfection, electroporation, ballistic bombardment, and the like. Alternatively, cells may be simply transfected with the disclosed expression vector using conventional technology described in the references and examples provided herein. The host cell can be a prokaryotic or eukaryotic cell, or any transformable organism that is capable of replicating a vector and/or expressing a heterologous gene encoded by the vector. Numerous cell lines and cultures are available for use as a host cell, and they can be obtained through the American Type Culture Collection (ATCC), which is an organization that serves as an archive for living cultures and genetic materials (www.atcc.org).

A host cell can be selected depending on the nature of the transfection vector and the purpose of the transfection. A plasmid or cosmid, for example, can be introduced into a prokaryote host cell for replication of many vectors. Bacterial cells used as host cells for vector replication and/or expression include DH5.alpha., JM109, and KC8, as well as a number of commercially available bacterial hosts such as SURE® Competent Cells and SOLOPACK Gold Cells (STRATAGENE, La Jolla, Calif.). Alternatively, bacterial cells such as *E. coli* LE392 could be used as host cells for phage viruses. Eukaryotic cells that can be used as host cells include, but are not limited to, yeast, insects and mammals. Examples of mammalian eukaryotic host cells for replication and/or expression of a vector include, but are not limited to, HeLa, NIH3T3, Jurkat, 293, Cos, CHO, Saos, and PC12. Examples of yeast strains include YPH499, YPH500 and YPH501. Many host cells from various cell types and organisms are available and would be known to one of skill in the art. Similarly, a viral vector may be used in conjunction with either an eukaryotic or prokaryotic host cell, particularly one that is permissive for replication or expression of the vector. Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

In vivo assays involve the use of various animal models, including non-human transgenic animals that have been engineered to have specific defects, or carry markers that can be used to measure the ability of a test compound to reach and affect different cells within the organism. Due to their size, ease of handling, and information on their physiology and genetic make-up, mice are a preferred embodiment, especially for transgenic animals. However, other animals are suitable as well, including *C. elegans*, rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

Determining the effectiveness of a compound in vivo may involve a variety of different criteria. Also, measuring toxicity and dose response can be performed in animals in a more meaningful fashion than in in vitro or in cyto assays.

VI). The Role of OSM and Metastasis

The role of inflammation in invasion and metastasis, particularly of prostate tumors, is not well understood. However, several studies show a correlation between serum levels of the interleukin-6 (IL-6) family inflammatory cytokines and distant metastases. Oncostatin M (OSM) is an inflammatory modulator in the interleukin-6 (IL-6) cytokine family that can be associated with the metastatic potential of prostate carcinomas. OSM promotes human prostate cancer cell proliferation, epithelial-mesenchymal transition (EMT) and detachment in vitro. In prostate cancer cells, OSM can induce vascular endothelial growth factor (VEGF) and urokinase-type plasminogen activator (u-PA), two proteins suspected to be involved in tumor progression. In addition, a pattern of increased OSM expression can occur in high grade Gleason (aggressive) carcinomas. OSM's influence on prostate cancer has only been minimally studied in vitro. It has been determined that OSM promotes invasive capacity of prostate tumor cells and their metastasizing potential.

Androgen deprivation therapy is the standard course of treatment for prostate cancer. However, most prostate cancers treated through androgen deprivation therapy eventually recur. Moreover, prostate tumors with high Gleason scores can be metastatic and/or refractory to androgen deprivation therapy. Therefore, alternative therapies, such as the OSM inhibitors disclosed herein may be advantageous.

OSM may play a role in prostate cancer. OSM expression can be directly associated with metastatic potential in clinical prostate carcinoma, with increasing OSM and OSM receptor expression being found in higher Gleason grade tumors. In vitro studies have shown that OSM induces both vascular endothelial growth factor (VEGF) and urokinase-type plasminogen-activator (u-PA) expression in DU-145 PCa cells, each of which are implicated in tumor progression. In addition, the proliferation of the DU-145 and 22Rv1 prostate cancer cell lines increases with increasing OSM values. OSM can also induce the epithelial to the mesenchymal transition (EMT), cell detachment, and invasive capacity of DU-145 cells.

OSM has been implicated in tumor invasion and metastasis of other tumors as well. These other types of tumors can include, for example, ovarian and breast cancer. Hereinafter, the inventors describe their detailed findings in relation to breast cancer, as these results can be readily extended to the understanding and treatment of prostate cancer.

We have studied the role of Oncostatin M (OSM) promoting the metastasis of breast tumors. OSM is a pro-inflammatory pleiotropic IL-6 family cytokine that plays a role in development, neurogenesis, liver regeneration, and haematopoiesis. OSM activates signaling pathways by binding its receptors, OSM receptor β (OSMRβ) or leukemia inhibitory factor receptor β (LIFRβ) dimerized with a common gp130 subunit. OSM also activates the JAK/STAT, MAPK, and PI3K/AKT pathways via binding its receptors. Moreover, OSM activates the stress-activated mitogen-activated protein kinases p38 and JNK.

In vitro studies examining the role of OSM signaling in breast cancer have suggested that this cytokine may increase the metastatic potential for breast epithelial cells. While OSM inhibits proliferation of various carcinomas including lung cancer, multiple myeloma and breast cancer, in other cancer types it actually increases proliferation. Though OSM's effect of tumor cell proliferation is not the same for any carcinoma, recent research suggests that this cytokine can promote invasion and metastasis. Specifically, OSM can function on various cancer cells in vitro to: 1) promote the transition from an epithelial to mesenchymal phenotype (EMT), 2) upregulate expression of proteases such as cathepsins, and matrix metalloproteinases (MMPs), 3) promote tumor cell-substrate invasion and detachment, and 4) induce the expression of vascular endothelial growth factor (VEGF), HIF1α and other proangiogenic factors, and 5) induce increased cancer cell stemness, suppress ER alpha expression, and promote S100A7 expression.

A role for OSM produced by tumor-associated immune cells can promote a metastatic phenotype in breast cancer cells in vitro. In response to breast cancer cells in vitro, macrophages and neutrophils collected from healthy human volunteers can express and secrete high levels of OSM, thereby supporting a role for OSM in the breast tumor microenvironment. Additionally, breast cancer cells alone secrete high levels of OSM in culture in addition to the immune cells. Taken together, these in vitro studies suggest a role for both autocrine and paracrine signaling by OSM in tumor metastatic potential, particularly during early stages of the metastatic cascade. Transgenic and other mouse models of OSM can show its importance in the production of red blood cells and platelets, wound-healing in the heart and liver, bone homeostasis, inflammatory cell migration and infiltration into injured tissue, and leukocyte activation.

We discovered that in vivo OSM can increase mammary tumor metastases to bone and increase bone metastatic osteolysis. Thus, OSM can influence normal bone homeostatis and in the bone metastatic microenvironment during later stages of breast cancer metastasis. Increased OSM expression can also lead to changes in ECM remodeling during breast tissue involution.

More specifically, we investigated the effect of OSM on early stages of breast cancer metastasis. First, we established the expression pattern of OSM in human breast tissue using tissue microarrays. We showed that OSM is expressed at higher levels in Invasive Ductal Carcinoma (IDC) than the adjacent normal breast tissue, but at highest levels in ductal carcinoma in situ (DCIS), suggesting that OSM may play an important role in the early stages of breast tumor invasion and metastasis. In order to further investigate this feature in vivo, we utilized the syngeneic model of 4T1.2 mouse mammary tumor cells that when injected into Balb/c mice established a metastatic pattern similar to that seen in breast cancer patients. We showed that a reduced OSM expression in 4T1.2 cells (4T1.2-shOSM) is sufficient to inhibit the progression and final number and volume of metastases in the lung. In this orthotopic model, our results demonstrate that reduced OSM significantly increases survival post-primary tumor resection; however, bypassing the early stages of metastasis by injecting cells directly into the systemic circulation, did not. We confirmed OSM increases early stage metastatic potential in vitro by showing OSM induces 4T1.2 tumor cell detachment and migration. These findings were corroborated with an in vivo study demonstrating that when OSM is injected peri-tumorally in a mice harboring MDA-MB-231 mammary tumors, there is an increase in the number of circulating tumor cells as well as spontaneous metastasis to lung. Findings from these studies suggest that autocrine and paracrine OSM in the tumor microenvironment acts as a potent initiator of invasion and the early stages of metastasis. Therefore, modification of OSM levels in the tumor microenvironment can be a highly effective therapeutic strategy for halting the invasion and metastasis of breast cancer.

An intriguing finding of this study is that OSM epithelial expression is higher in earlier stages of ductal carcinoma of the breast (DCIS and IDC) compared to metastatic disease, which is consistent with the proposed role of OSM in vitro that it promotes the initiation of invasiveness of breast cancer. Higher levels of OSM and OSMR are seen in breast tissue as it progresses from ductal carcinoma in situ to invasive ductal carcinoma. Although OSM expression has been studied in various human tumors such as prostate cancer, ovarian cancer and keratocanthoma, the present study may provide additional insights into the role of OSM in breast cancer and in these other types of cancers. In breast cancer, in vivo research suggests a role for OSM in metastasis. OSM can promote bone metastases and bone destruction from the metastases and can promote the protein expression of EMT markers.

We investigated the role of OSM during the earliest stages of invasion and metastasis in an animal model. Our orthotopic injection studies have shown that OSM promotes maximum metastatic burden in lung and bone. Additionally, utilizing a modified human breast cancer cell line, the MDA-MB-231 cells, in an athymic, immunocompromised mouse, OSM applied directly to the tumor microenvironment increases the number of circulating tumor cells and number of metastasis to the lung. However, when we bypass the early stages of metastasis or those preceding colonization at a secondary metastatic site by implanting 4T1.2 mouse mammary tumor cells via intracardiac injection, there is no change in metastasis to the lung or survival time driven by OSM.

The difference between using a Balb/c mouse with mouse mammary tumor cells versus an athymic mouse with human breast cancer cells is not insignificant and one major difference between the two models. Application of human OSM directly to the tumor microenvironment did not affect primary tumor growth with the human MDA-MB-231 cells-DH3LN-luc., while loss of OSM from the mouse cells increased tumor growth. An explanation for this could be that full-length OSM may be less effective on growth inhibition in vivo due to its need for processing and its differential ability to signal when bound to proteins in the extracellular matrix of the tumor micron environment. Human OSM gene encodes a 252 amino acid (aa) polypeptide: the first 25 aa encode a signal sequence for secretion; the remaining 227 aa are the precursor protein named pro-OSM or full-length OSM. Cleavage of the c-terminis at a trypsin-like cleavage site yields the mature (aka active or truncated) 196 aa form. Both full-length and truncated OSM display similar receptor binding affinity, but full-length OSM was found to be 5 to 60-fold less effective on growth inhibition. Processing of OSM may regulate OSM activities in vivo. This differential growth effect between the two forms explains why peri-tumor injection of full-length OSM had no effect on primary tumor growth, but still maintained the functional properties of increased metastatic burden.

To explain the role of OSM in early stages of metastasis, we showed that 4T1.2 cells can detach, invade, and migrate in response to the cytokine. Epithelial cells, from which the majority of cancer cells such as 4T1.2 cells arise from, are not normally motile or invasive. In order for cancer cells to detach, invade, and become mobile through the ECM, they are thought to transform from an epithelial phenotype to a more mesenchymal phenotype. This phenomenon known as EMT involves reorganization of the cytoskeleton to allow cells to become mobile and thus migrate. As the cells become mesenchymal, they can produce proteinases such as matrix metalloproteinases to detach and invade into the ECM. Our results suggest that OSM's activity is primarily focused within the primary tumor and does not have an effect once the cells escape into the circulatory system. This is seen as OSM promotes tumor detachment and invasion in vitro, and metastasis in vivo when breast tumor cells are injected orthotopically.

It has been thought that tumor cell EMT, detachment, and invasion promote tumor cell propagation into the circulation and are thought to be precursors for intravasation and circulating tumor cells (CTC). Specifically, the cell's propensity to intravasate into circulation directly correlates to the level of CTC's. CTC's have also been linked clinically to enhanced metastatic burden in patients and a reduced 5-year survival rate. While the exact mechanisms that regulate CTC generation is unclear, factors such as transforming growth factor beta (TGF-beta), IL-6, and interleukin-8 may act as promoters of CTCs either by increasing tumor cell invasion, detachment, or EMT. Additionally, CTCs in general can tend to have a heterogeneous expression of genes and mixed epithelial/mesenchymal phenotypes, which complicate detection, and prognostic prediction. Results suggest that tumor cells that intravasate into circulation and become CTCs undergo EMT, invade through the ECM, and detach. Our data shows that OSM injection increases the number of CTCs in tumor bearing mice and this increase may be caused by OSM's effects on the early stages of metastases. Inflammatory cytokines such as IL-6, IL-17, and M-CSF at the site of the secondary lung metastasis, as well as in systemic circulation may foster their ability to proliferate, survive, and migrate. To date, it is not believed that investigation of OSM as a cellular cue in primary breast tumor environment promoting metastasis to the lung, despite several studies of the very closely related IL-6 cytokine.

OSM's pivotal role in the metastasis of primary cancers of the breast to sites such as bone and lung, and the known properties of OSM in the progression of inflammatory diseases, including arthritis and lung fibrosis give insight into the mechanisms that might drive OSM in the metastatic cascade. Tumors often appear to have chronic inflammation mediated by tumor-associated macrophages (TAMs). TAMs generally exhibit an M2 phenotype in which they produce growth factors and cytokines, promote ECM remodeling through the expression of proteases, and increase angiogenesis through the production of VEGF. Both tumor-infiltrating macrophages and neutrophils express and release OSM in response to breast carcinoma cells in vitro. OSM can also play a role in the switch from the M1 phenotype to M2 phenotype. OSM can also be both pro and anti-inflammatory in vivo but in the absence of tumor cells, OSM can trigger inflammatory cell recruitment when expressed in joints and lungs and enhance dendritic cell homing to regional lymph nodes. In addition, OSM can promote changes in the ECM by increasing collagen deposition and increasing expression of proteases. In arthritic models, OSM can promote bone and cartilage production at higher levels than IL-6. Inflammatory cytokines such as IL-6, IL-17, and M-CSF can promote mammary tumor metastasis to the lung in the PyV MT mouse model when an arthritic disease state is induced with Type II collagen. In studies of skin inflammation, OSM can contribute to keratinocyte hyperplasia in psoriasis and dermatitis.

OSM can also promote inflammation and fibrosis in lung tissue and currently, and if chronic inflammation in the lung is present from either smoking or disease, breast cancer metastasis to the lung may be promoted. In both our in vivo models with either decreased OSM expression (4T1.2 mouse mammary tumor cells in a healthy Balb/c mouse) or application of OSM directly to the tumor microenvironment (MDA-MB-231 human breast cancer cells in an immunocompromised nude mouse), there is no increased basal inflammation in the lung microenvironment. Therefore, we can assume that inflammation is not the driving force for our observed differences in metastatic burden by OSM. However, OSM appears to be more important for initiating the early steps in the metastatic cascade preceding colonization in the lung.

OSM also increased IL-6 expression only in the ER-breast cancer cell lines MDA-MB231, MDA-MB-468, and 4T1.2 cells. IL-6 can increase breast cancer migration, invasion, and detachment. IL-6 can also induces EMT, and high serum IL-6 levels can be associated with poor prognosis in breast cancer patients. OSM's effect on tumor progression may also be magnified by the induction of IL-6, as IL-6 can also promote further induction of IL-6 production in a feed forward system.

In the bone microenvironment, OSM expression by metastatic cells can directly interfere with the homeostasis of the osteogenic cells, and lead to increased osteolysis, suggesting a role for OSM in the metastatic niche during later stages of metastasis.

Returning to prostate cancer, the inventors now describe their further findings in relation to this tumor. FIG. 1 shows a schematic of a mechanism by which OSM is presumed to promote the metastasis and progression of prostate tumors. OSM produced by prostate tumor cells promotes the expression of proteases, such as MMPs and cathepsins that in turn stimulate EMT, detachment, and invasiveness of tumor cells. In addition, OSM can induce tumor cell expression of proangiogenic factors such as VEGF and u-PA that promote angiogenesis and metastasis.

OSM can play a role in the initial stages of prostate cancer metastasis. DU-145 prostate cancer cells can undergo increased proliferation, EMT, detachment, and invasive potential in response to OSM treatment. Previous studies suggest that OSM's effects on proliferation and cell detachment work through a STAT3 signaling mechanism, but that its effects on invasive potential may work through a different pathway. In vitro studies indicate that OSM can induce vascular endothelial growth factor (VEGF) and urokinase-type plasminogen activator (u-PA) in prostate cancer cells.

Given the role of OSM in the metastases of prostate cancer and other types of cancer, and the previous results of several small molecules showing the inhibition of OSM induced phosphorylation of various signaling peptides, further small molecule inhibitors of OSM were assayed for similar inhibition. It is our assumption that increased inhibition of OSM may be correlated with a decreased degree of cancer metastases, particularly prostate cancer metastases. Several small molecules were investigated in this regard and are summarized in Tables 1 and 2.

Methods for inhibiting OSM can include exposing OSM or a cell line expressing OSM to a small molecule inhibitor of OSM, including those found in Tables 1 and 2 or various derivatives thereof.

Methods for treating cancer can include administering a pharmaceutical composition containing a small molecule OSM inhibitor to a patient with prostate cancer. Administration can be orally, parenterally, rectally, topically, intravenously, and the like under a suitable dosing schedule compatible with the metabolic clearance of the active compound. The active compound is included in a pharmaceutically acceptable carrier in an amount sufficient to exert a therapeutically useful effect in the patient being treated. The therapeutically effective concentration may be determined empirically by testing the compounds in in vitro and in vivo systems described herein and then extrapolated therefrom for dosages for humans. The concentration of active compound in the pharmaceutical composition will depend on absorption, inactivation and excretion rates of the active compound, the physicochemical characteristics of the compound, the dosage schedule, and amount administered as well as other factors known to those of skill in the art.

Unless defined otherwise, all technical and scientific terms used herein have the same meanings as commonly understood by one of skill in the art to which the disclosed invention belongs. Patent publications cited herein and the materials for which they are cited are specifically incorporated by reference. To facilitate a better understanding of the embodiments of the present disclosure, the following examples are given. In no way should the following examples be read to limit, or to define, the scope of the invention.

EXAMPLES

Example 1: Modified OSM-SMI-8 Small Molecule Inhibitors

A previous study suggests that OSM mediates its effect on proliferation and detachment through a STAT3 signaling pathway and suggests that the increased invasive potential mediated by OSM uses a signaling pathway distinct from that of proliferation and cell detachment and one that does not use STAT3. Therefore, the phosphyloration of various signaling pathways was assayed using an ELISA both with and without inhibitors and at various concentrations.

All human breast carcinoma cell lines used in this aim were purchased from the American Type Culture Collection (ATCC) or Caliper Life Sciences, and the growth of frozen cell aliquots will be initiated on a periodic basis to remove the possibility of cross-cell contamination. The cell lines were regularly tested for mycoplasma contamination by both DAPI staining and PCR. Four invasive ductal carcinoma cell lines, T47D, MCF7, MDA-MB-231 and MDA-MB-468, were used. These include the less aggressive, estrogen receptor-positive (ER+), progesterone receptor positive (PR+), HER2−, luminal T47D and MCF7-luc cell lines, as well as the triple negative breast cancer (TNBC) basal-like cell line, MDA-MB-231-LN-luc, that is metastatic in orthotopic xenografts and the less metastatic TNBC cell line MDA-MB-468. All cell lines express OSMRb, LIFRb, and gp130, as well as various levels of OSM, by RT-PCR An enzyme-linked immunosorbent assay (ELISA) was used for analyzing initial OSM-induced phosphorylation of STAT3 on Tyr-705 (pSTAT3). T47D, MCF7, and MDA-MB-231 human breast cancer cells induced pSTAT3 upon stimulation with OSM (25 ng/ml) for 30 minutes. OSM-SMI-8 modified inhibitors were used to pretreat the cells in order to assay their ability to inhibit OSM-OSMR interactions. Pretreatment consisted of administering to the cells either 5, 10, 50, or 100 µM of the modified OSM-SMI-8 based inhibitor for 2 hours prior to administration of OSM.

Figure 2:
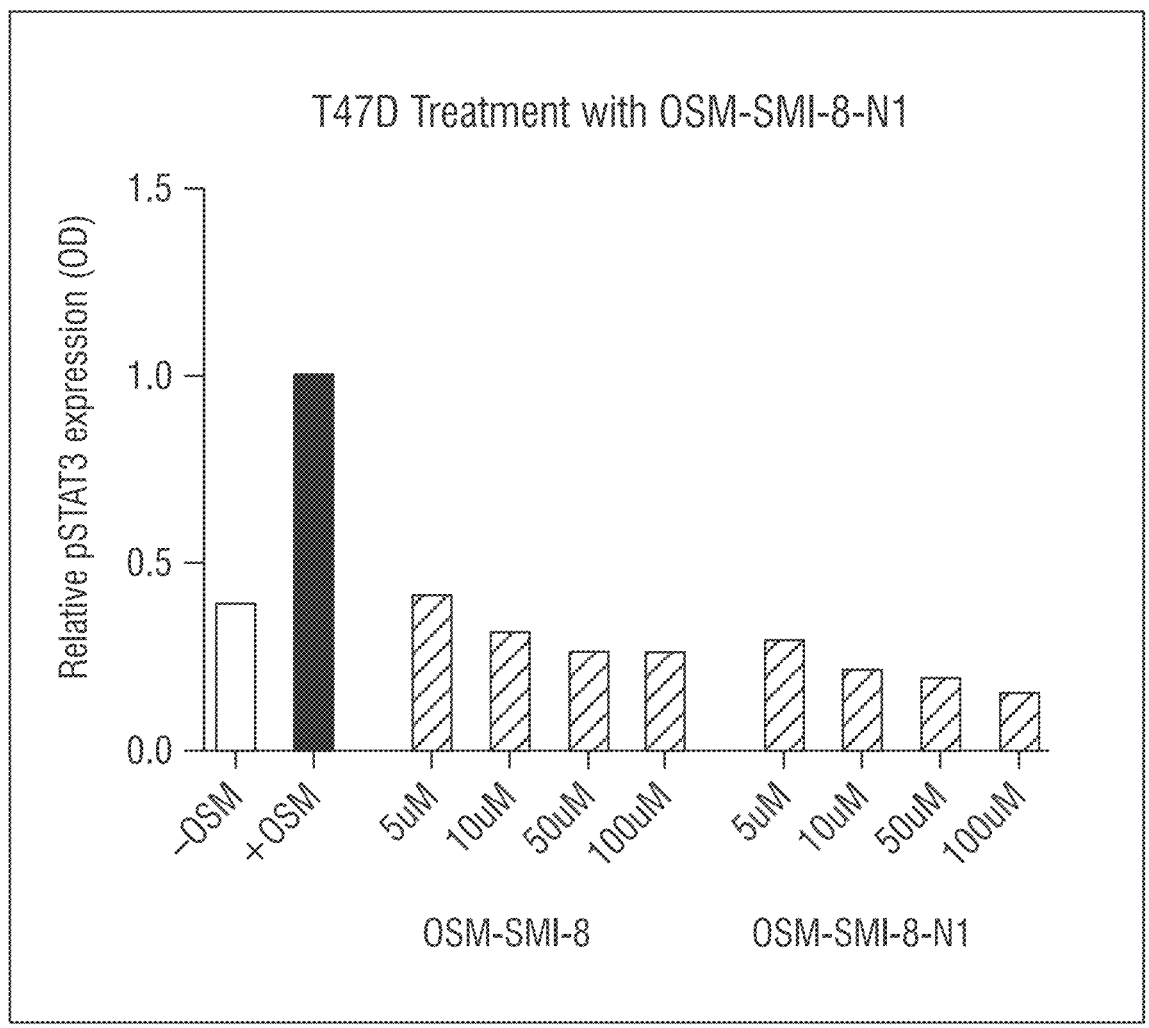
FIG. 2 is a graphical representation of the effect of OSM induced pSTAT3 expression by two different OSM inhibitors, OSM-SMI-8 and OSM-SMI-8N1, in T47D cells at varying concentrations.

The compounds in Table 1 were assayed using a pSTAT ELISA test in T47D breast cancer cells (FIG. 2). Surprisingly, a nitro modified OSM-SMI-8 compound, OSM-SMI-8N1, demonstrated a significant inhibition of pSTAT3 after treatment with OSM at every administered dosage. Further, this compound showed an increased inhibition over OSM-SMI-8. Actual physiological levels of OSM may be much lower than the nanogram levels used here. Healthy humans have been shown to have OSM serum levels of 6-13 pg/ml, cancer patients with hepatocellular carcinoma have serum levels of 39-121 pg/ml, and mice with MDA-MB-231 mammary tumors contain 6 to 85 pg/ml in their serum. Therefore, testing inhibitors using lower concentrations of OSM may better allow for the detection of effects at physiologically relevant concentrations.

As it has been shown earlier that pSTAT3 is related to detachment and metastasis in various cancers, OSM-SMI-8N1 and other of the modified OSM-SMI-8 compounds are more efficient OSM inhibitors than OSM-SMI-8.

Example 2: Modified OSM-SMI-10 Small Molecule Inhibitors

Figure 3:
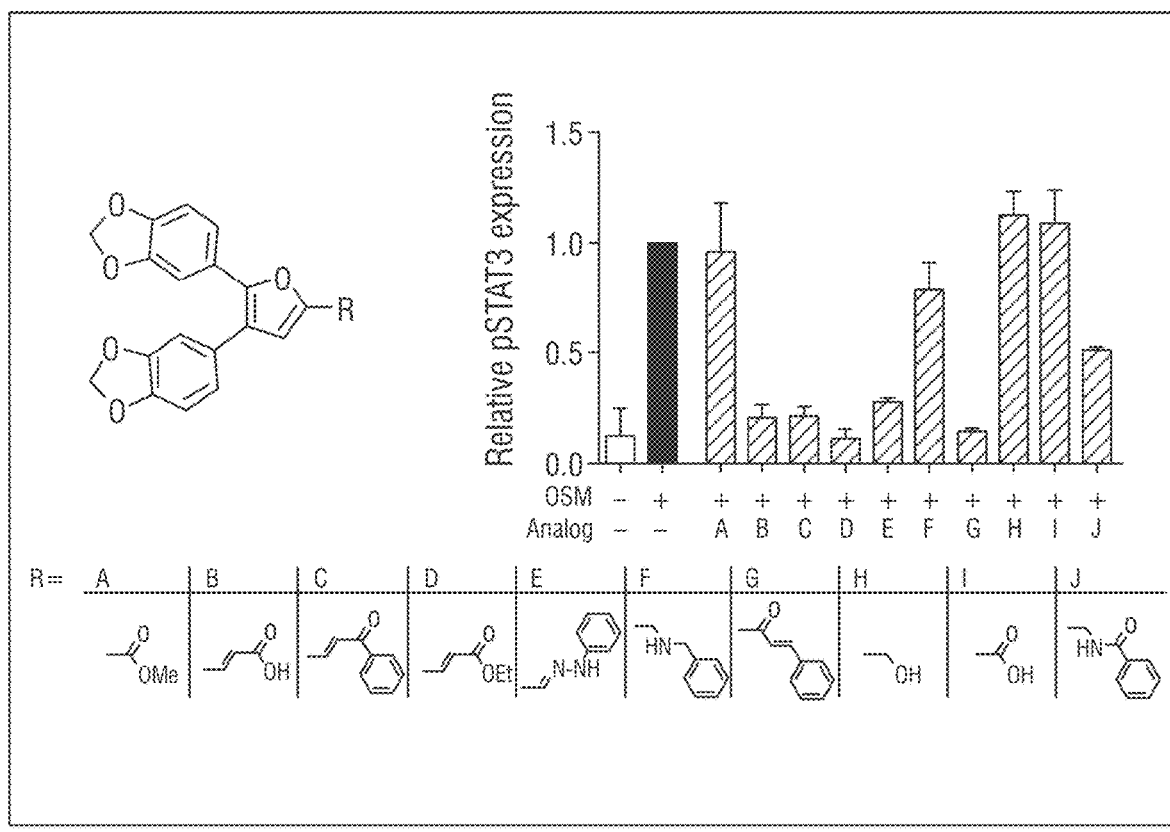
FIG. 3 is a graphical representation of the effect of OSM induced pSTAT3 expression by ten different OSM inhibitors, OSM-SMI-10A-J.

Similar to Example 1, OSM-SMI-10 was modified both in the two aryl regions and the R group off the furan ring (FIG. 3 and Table 2) to generate new compounds which may have an increased inhibitor effect on OSM induced metastasis. As in Example 1, the level of pSTAT3 was assayed using OSM with or without inhibitor pretreatment by ELISA for OSM-SMI-10A, OSM-SMI-10B, OSM-SMI-10C, OSM-SMI-10D, OSM-SMI-10E, OSM-SMI-10F, OSM-SMI-10G, OSM-SMI-10H, OSM-SMI-10I, and OSM-SMI-10J. Initial tests showed that OSM-SMI-10B, OSM-SMI-10C, OSM-SMI-10D, OSM-SMI-10E, OSM-SMI-10G, and OSM-SMI-10J had an inhibitory effect on OSM induced pSTAT3 phosphorylation (FIG. 3).

Figure 4A:
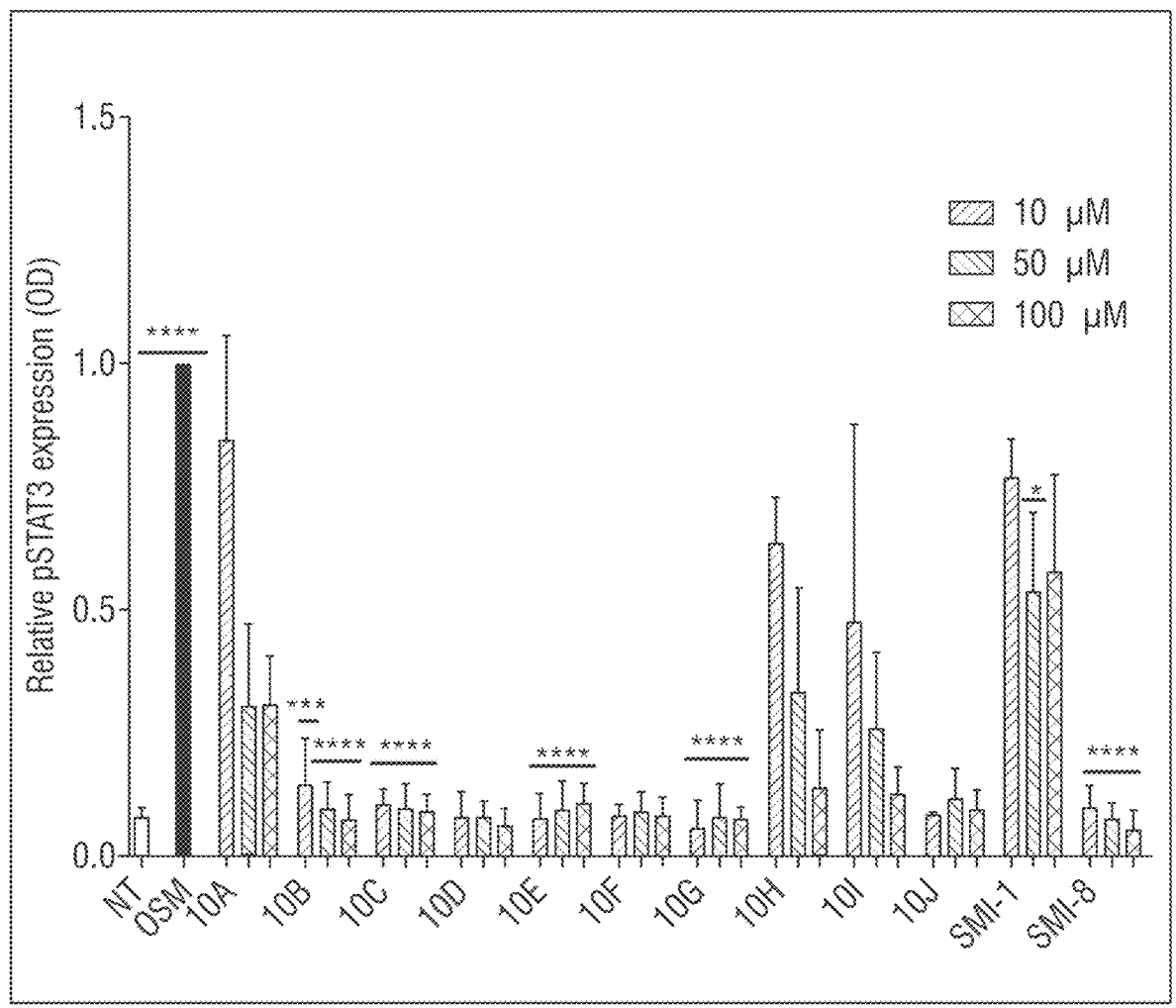
FIG. 4 is a graphical representation of the effect of OSM induced pSTAT3 expression by various OSM inhibitors at 10, 50, and 100 μM concentrations. Data expressed as mean±SEM, *P<0.05, P<0.01, *P<0.001, **P<0.0001, ***P<0.00001, t-test.
FIG. 4B is a representative gel image of the pSTAT3 expression for the graph of FIG. 3A.
Figure 4B:
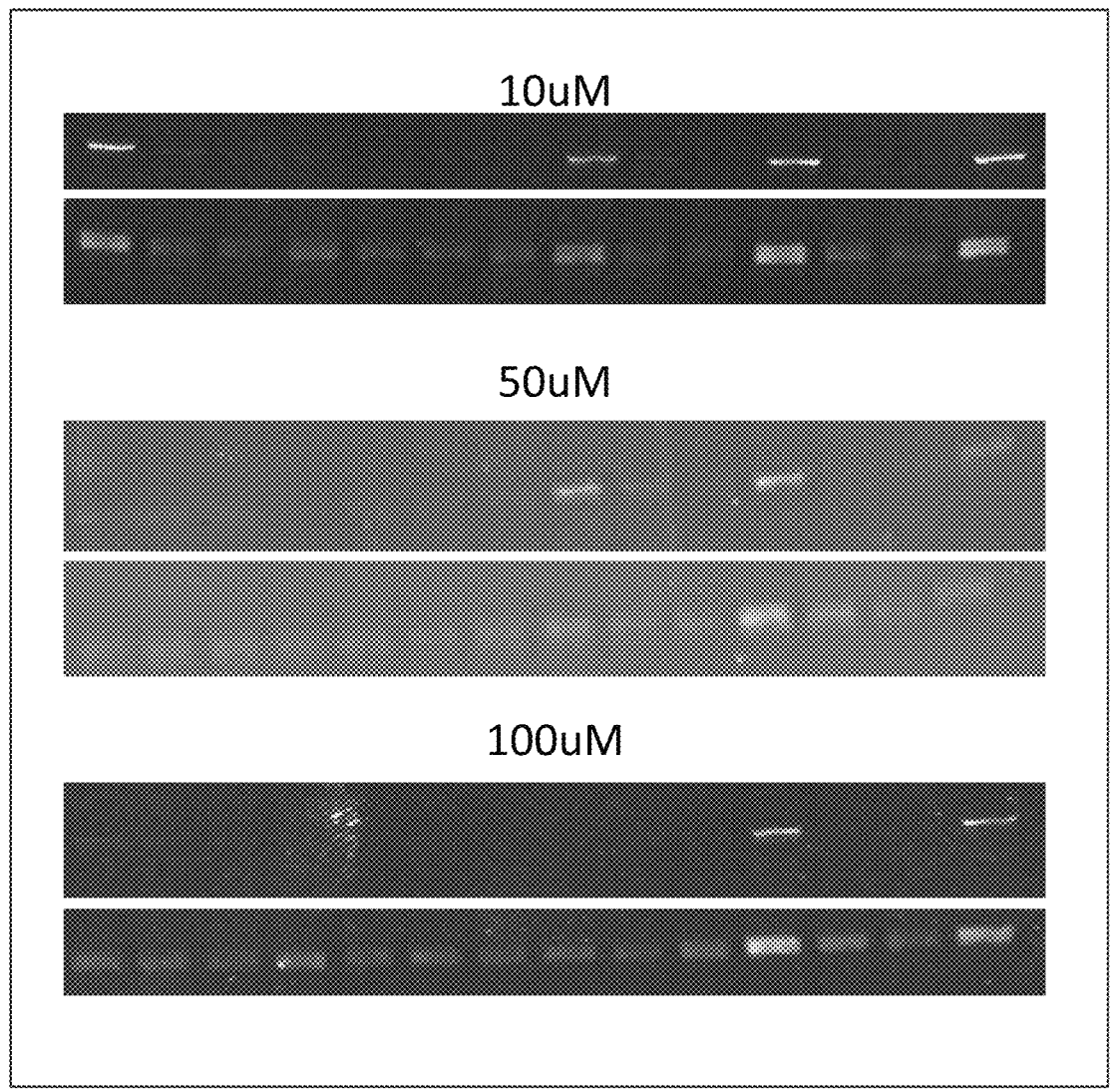

Testing the inhibition at three different levels, 10, 50, and 100 µM per the method of Example 1, resulted in significant decreases in OSM induced phosphorylation of STAT3 (FIGS. 4A and 4B). Specifically, OSM-SMI-10B, OSM-SMI-10C, OSM-SMI-10E, and OSM-SMI-10G all had a significant reduction in pSTAT3 at every treatment level.

Figure 5:
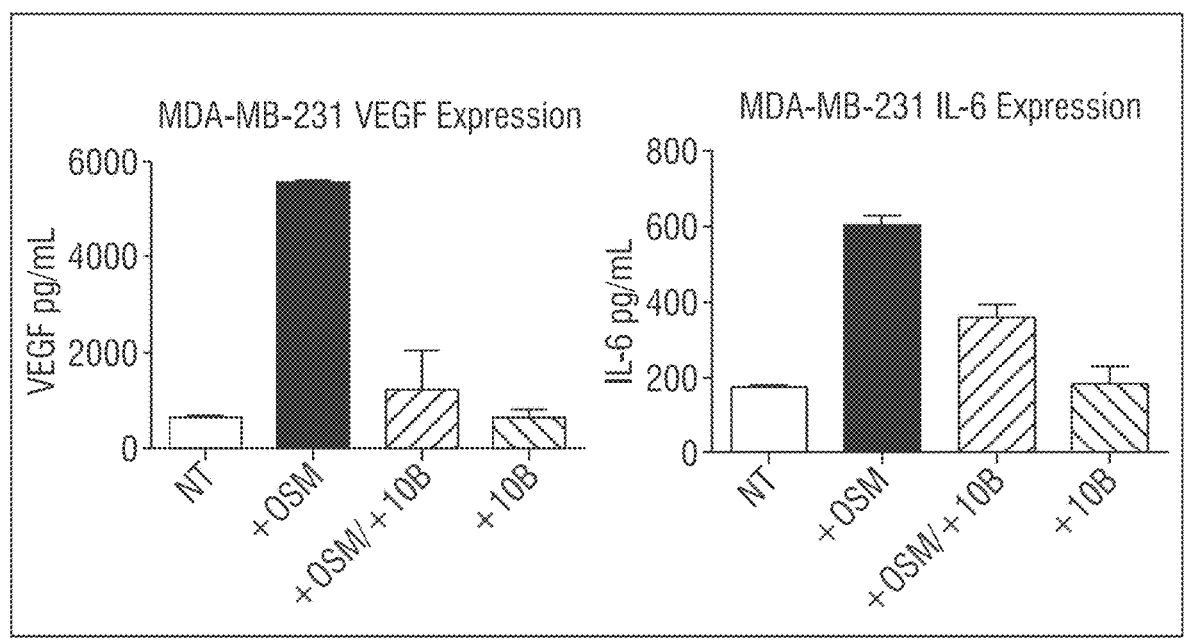
FIG. 5 is a graphical representation showing the decrease in secretion of OSM induced VEGF and IL-6 secretion by OSM-SMI-10B.

OSM-SMI-10B was also assayed for its effect on OSM induced secretions of both VEGF and IL-6 by ELISA (FIG. 5). Pretreatment with OSM-SMI-10B showed a large reduction in the OSM induction of both VEGF and IL-6 secretion.

As it has been shown earlier that pSTAT3 is related to detachment and metastasis in various cancers, OSM-SMI-10B, OSM-SMI-10C, OSM-SMI-10E, and OSM-SMI-10G and other of the modified OSM-SMI-10 compounds may be efficient OSM inhibitors.

Previous studies have shown that pSTAT3, IL-6, and VEGF are related to the progression and metastasis of cancer. Therefore, modified OM-SMI-10 compounds, including OSM-SMI-10B, OSM-SMI-10C, OSM-SMI-10E, and OSM-SMI-10G, due to their effectiveness at reducing OSM induced phosphorylation and secretion, these compounds would also be effective at slowing the progression and proliferation of cancers and reducing metastasis.

Example 3: OSM-SMI-23 and OSM-SMI-26 Small Molecule Inhibitors

Figure 6:
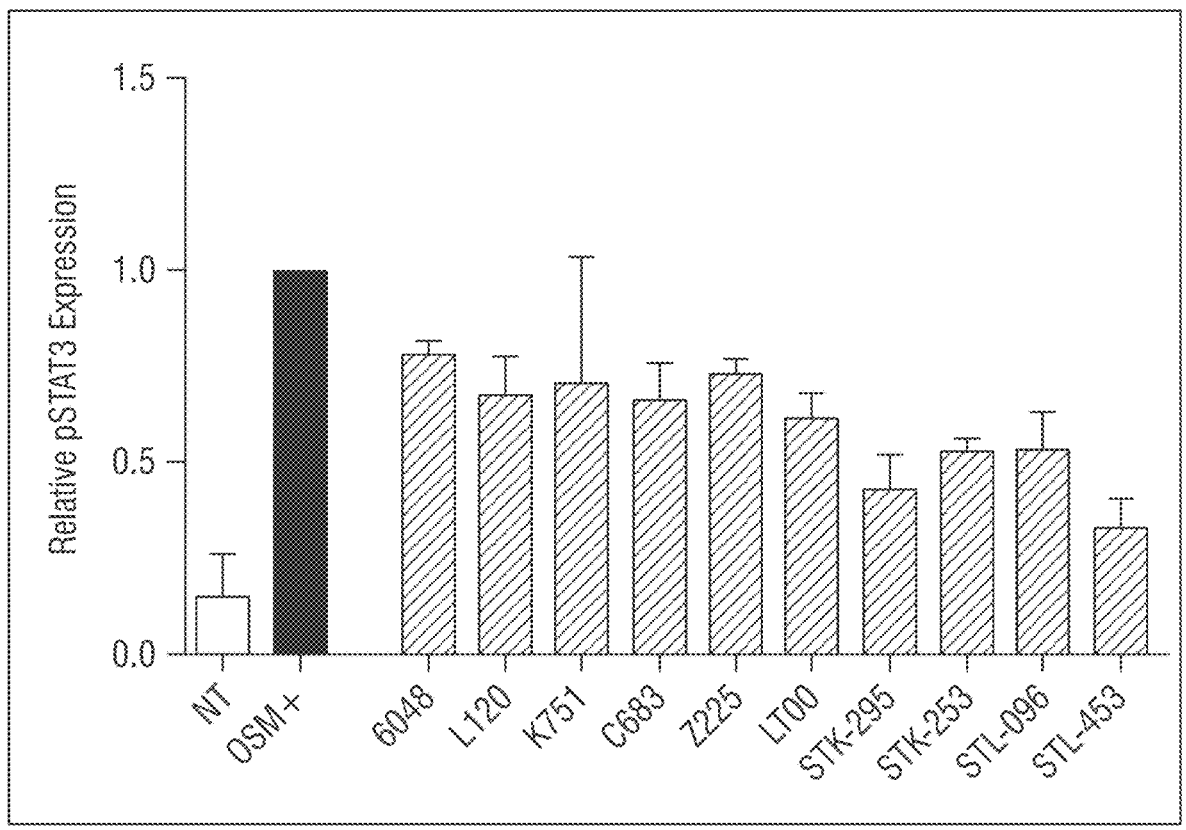
FIG. 6 is a graphical representation showing the effect of OSM induced pSTAT3 expression by various OSM inhibitors, where STK-295 is OSM-SMI-23 and STK-453 is OSM-SMI-26.
Figure 7:
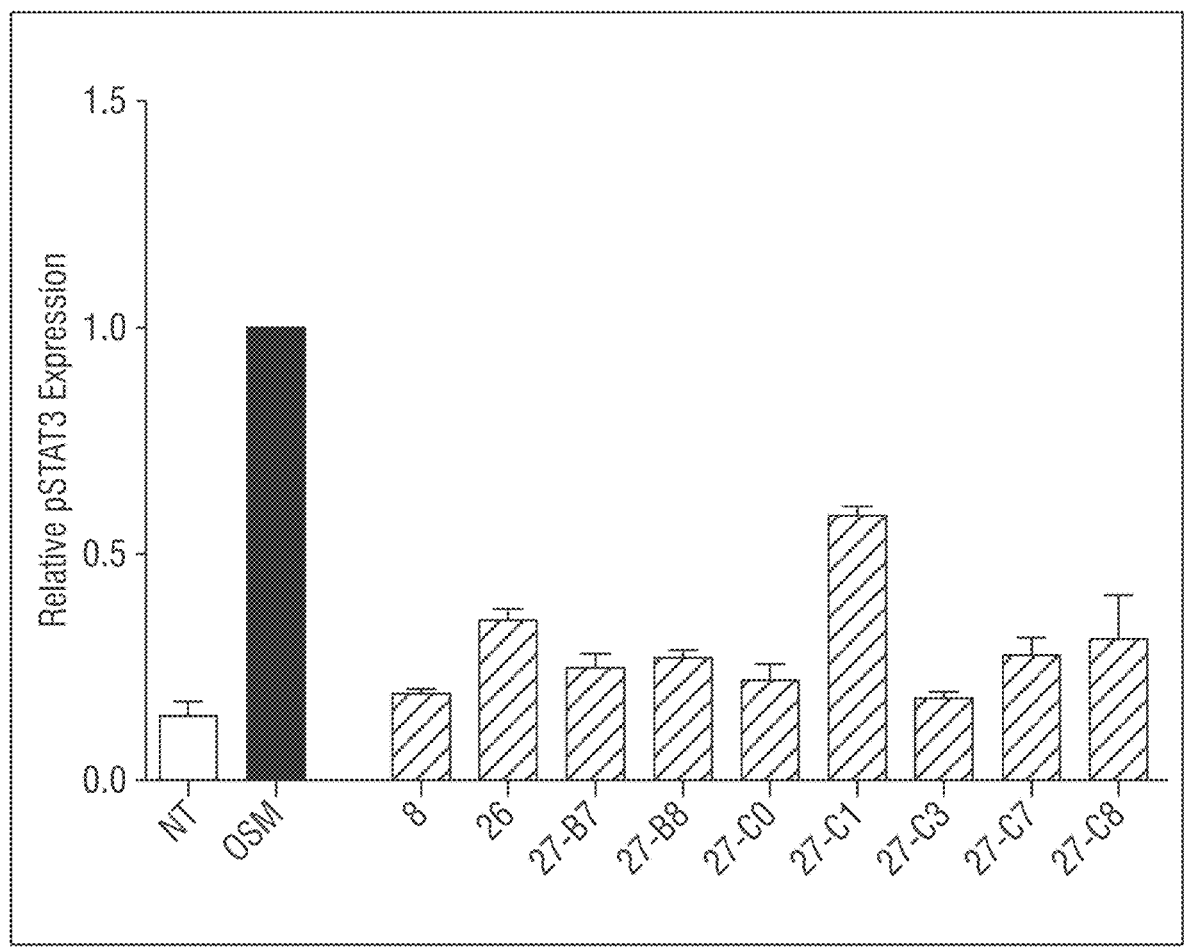
FIG. 7 is a graphical representation showing the effect of OSM induced pSTAT3 expression in T47D cells by various OSM inhibitors.
Figure 8:
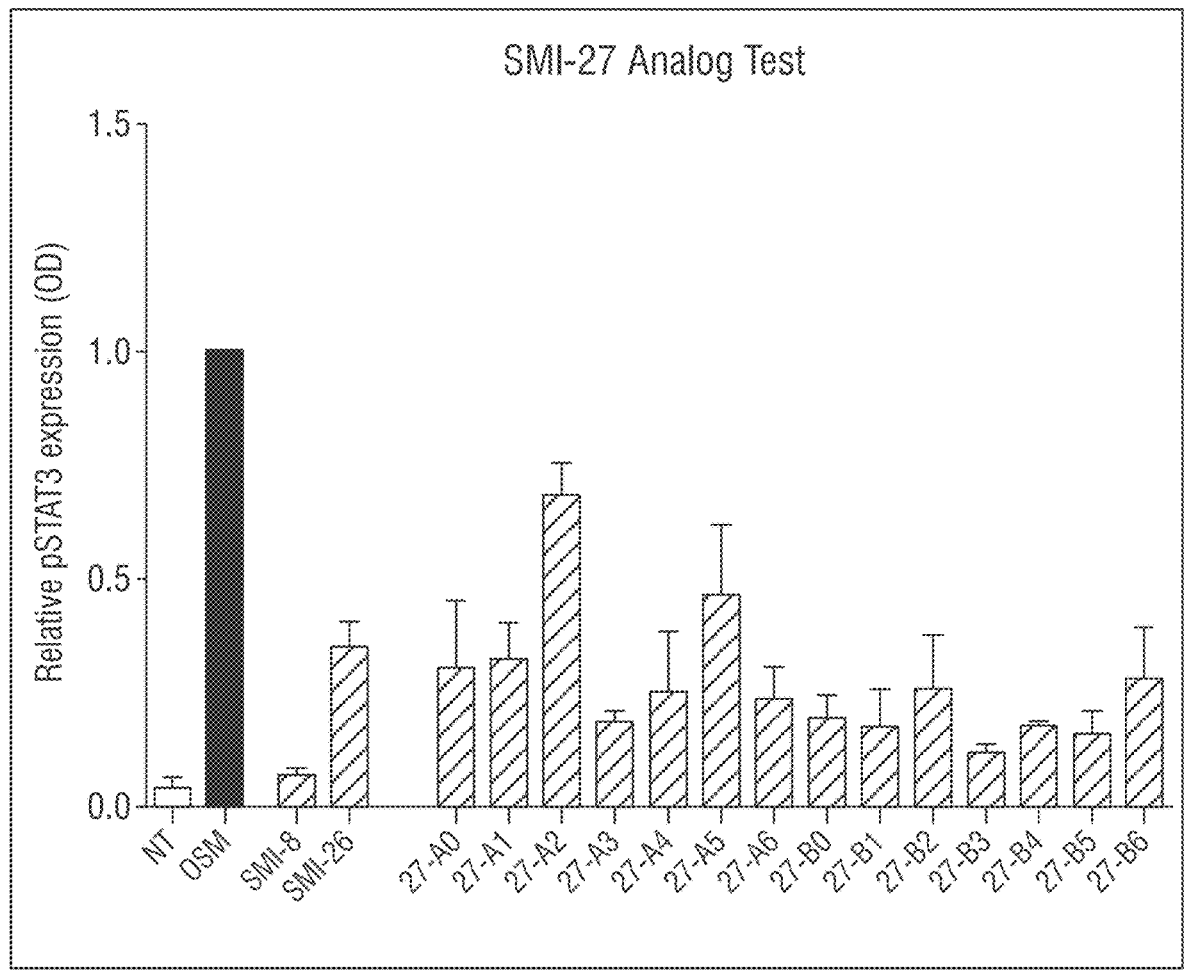
FIG. 8 is a graphical representation showing the effect of OSM induced pSTAT3 expression by various OSM inhibitors.

Similar to Example 1, OSM-SMI-23 (labeled STK-295 in FIG. 6) and OSM-SMI-26 (labeled as STK-453 in FIG. 6)

were modified to generate new compounds (Table 3) which may have an inhibitory effect on OSM induced cellular changes. As in Example 1, the level of pSTAT3 was assayed using OSM with or without inhibitor pretreatment by ELISA for the OSM-SMI-23 and OSM-SMI-26. Initial testing shows that both OSM-SMI-23 and OSM-SMI-26 reduced the OSM induced increase in pSTAT3 expression by more than about half (FIG. 6). Therefore, similarly to OSM-SMI-8 and OSM-SMI-10 and their modified compounds, OSM-SMI-23 and OSM-SMI-26 would be effective at reducing the detachment and metastasis of cancerous cells, as well as slowing the progression and proliferation of cancers.

Example 4: OSM Protein and DNA Sequences

```
Protein Oncostatin M GENBANK
AAH11589
                                                         (SEQ ID NO: 1)
MGVLLTQRTL LSLVLALLFP SMASMAAIGS CSKEYRVLLG QLQKQTDLMQ

DTSRLLDPYI RIQGLDVPKL REHCRERPGA FPSEETLRGL GRRGFLQTLN

ATLGCVLHRL ADLEQRLPKA QDLERSGLNI EDLEKLQMAR PNILGLRNNI

YCMAQLLDNS DTAEPTKAGR GASQPPTPTP ASDAFQRKLE GCRFLHGYHR

FMHSVGRVFS KWGESPNRSR RHSPHQALRK GVRRTRPSRK GKRLMTRGQL PR

DNA Oncostatin M GENBANK
BC011589.1
                                                         (SEQ ID NO: 2)
    1  gtcaccccca gcgggcgcgg gccggagcac gggcacccag catgggggta ctgctcacac 61  agaggacgct gctcagtctg gtccttgcac tcctgtttcc aagcatggcg agcatggcgg 121  ctataggcag ctgctcgaaa gagtaccgcg tgctccttgg ccagctccag aagcagacag 181  atctcatgca ggacaccagc agactcctgg accctatat acgtatccaa ggcctggatg 241  ttcctaaact gagagagcac tgcagggagc gccccggggc cttccccagt gaggagaccc 301  tgaggggct gggcaggcgg ggcttcctgc agaccctcaa tgccacactg ggctgcgtcc 361  tgcacagact ggccgactta gagcagcgcc tccccaaggc ccaggatttg gagaggtctg 421  ggctgaacat cgaggacttg gagaagctgc agatggcgag gccgaacatc ctcgggctca 481  ggaacaacat ctactgcatg gcccagctgc tggacaactc agacacggct gagcccacga 541  aggctggccg gggggcctct cagccgccca ccccacccc tgcctcggat gcttttcagc 601  gcaagctgga gggctgcagg ttcctgcatg gctaccatcg cttcatgcac tcagtggggc 661  gggtcttcag caagtggggg gagagcccga accggagccg gagacacagc ccccaccagg 721  ccctgaggaa gggggtgcgc aggaccagac cctccaggaa aggcaagaga ctcatgacca 781  ggggacagct gccccggtag cctcgagagc accccttgcc ggtgaaggat gcggcaggtg 841  ctctgtggat gagaggaacc atcgcaggat gacagctccc gggtcccaa acctgttccc 901  ctctgctact agccactgag aagtgcactt taagaggtgg gagctgggca gacccctcta 961  cctcctccag gctgggagac agagtcaggc tgttgcgctc ccacctcagc cccaagttcc 1021  ccaggcccag tggggtggcc gggcgggcca cgcgggaccg actttccatt gattcagggg 1081  tctgatgaca caggctgact catggccggg ctgactgccc ccctgccttg ctccccgagg 1141  cctgccggtc cttccctctc atgacttgca gggccgttgc ccccagactt cctcctttcc 1201  gtgtttctga aggggaggtc acagcctgag ctggcctcct atgcctcatc atgtcccaaa 1261  ccagacacct ggatgtctgg gtgacctcac tttaggcagc tgtaacagcg gcagggtgtc 1321  ccaggagccc tgatccgggg gtccagggaa tggagctcag gtcccaggcc agccccgaag 1381  tcgccacgtg gcctggggca ggtcacttta cctctgtgga cctgttttct ctttgtgaag 1441  ctagggagtt agaggctgta caaggccccc actgcctgtc ggttgcttgg attccctgac 1501  gtaaggtgga tattaaaaat ctgtaaatca ggacaggtgg tgcaaatggc gctgggaggt 1561  gtacacggag gtctctgtaa aagcagaccc acctcccagc gccgggaagc ccgtcttggg
```

-continued

```
1621  tcctcgctgc tggctgctcc ccctggtggt ggatcctgga attttctcac gcaggagcca 1681  ttgctctcct agagggggtc tcagaaactg cgaggccagt tccttggagg gacatgacta 1741  atttatcgat ttttatcaat ttttatcagt tttatattta taagccttat ttatgatgta 1801  tatttaatgt taatattgtg caaacttata tttaaaactt gcctggtttc taaaaaaaaa 1861  aaaaaaaaa
```

Therefore, the present disclosure is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed:

1. A method of inhibiting or reducing tumor cell detachment, progression, proliferation and/or metastasis comprising:
administering to a subject an effective amount of one or more OSM small molecule antagonists from the group of: OSM-SMI-8A, OSM-SMI-8B, OSM-SMI-8C, OSM-SMI-8D, OSM-SMI-8E, OSM-SMI-8F, OSM-SMI-8G, OSM-SMI-8H, OSM-SMI-8I, OSM-SMI-8J, OSM-SMI-8N1, OSM-SMI-10A, OSM-SMI-10B, OSM-SMI-10B-2, OSM-SMI-10B-3, OSM-SMI-10B-4, OSM-SMI-10B-5, OSM-SMI-10B-6, OSM-SMI-10B-7, OSM-SMI-10B-8, OSM-SMI-10B-9, OSM-SMI-10B-10, OSM-SMI-10B-11, OSM-SMI-10B-12, OSM-SMI-10B-13, OSM-SMI-10B-14, OSM-SMI-10B-15, OSM-SMI-10B-16, OSM-SMI-10B-17, OSM-SMI-10B-18, OSM-SMI-10B-19, OSM-SMI-10B-20, OSM-SMI-10B-21, OSM-SMI-10B-22, OSM-SMI-10B-23, OSM-SMI-10B-24, OSM-SMI-10B-25, OSM-SMI-10B-26, OSM-SMI-10B-27, OSM-SMI-10B-28, OSM-SMI-10B-29, OSM-SMI-10B-30, OSM-SMI-10B-31, OSM-SMI-10B-32, OSM-SMI-10B-33, OSM-SMI-10B-34, OSM-SMI-10B-35, OSM-SMI-10B-36, OSM-SMI-10B-37, OSM-SMI-10C, OSM-SMI-10D, OSM-SMI-10E, OSM-SMI-10F, OSM-SMI-10G, OSM-SMI-10H, OSM-SMI-10I, OSM-SMI-10J, OSM-SMI-10K, OSM-SMI-10L, OSM-SMI-10M, OSM-SMI-10N, OSM-SMI-10O, OSM-SMI-10P, OSM-SMI-10Q, OSM-SMI-10R, OSM-SMI-10S, OSM-SMI-23, OSM-SMI-23A, OSM-SMI-23B, OSM-SMI-23C, OSM-SMI-23D, OSM-SMI-23E, OSM-SMI-23F, OSM-SMI-23G, OSM-SMI-23H, OSM-SMI-23I, OSM-SMI-23J, OSM-SMI-23K, OSM-SMI-23L, OSM-SMI-23M, OSM-SMI-23N, OSM-SMI-23O, OSM-SMI-23P, OSM-SMI-23R, OSM-SMI-26, OSM-SMI-26A, OSM-SMI-26B, OSM-SMI-26C, OSM-SMI-26D, OSM-SMI-26E, OSM-SMI-26F, OSM-SMI-26G, OSM-SMI-26H, OSM-SMI-26I, OSM-SMI-26J, OSM-SMI-26K, OSM-SMI-26L, OSM-SMI-26M, OSM-SMI-26N, OSM-SMI-26O, OSM-SMI-26P, OSM-SMI-26Q, OSM-SMI-27, OSM-SMI-27-A1, OSM-SMI-27-A2, OSM-SMI-27-A3, OSM-SMI-27-A4, OSM-SMI-27-A5, OSM-SMI-27-A6, OSM-SMI-27-A7, OSM-SMI-27-A8, OSM-SMI-27-A9, OSM-SMI-27-A10, OSM-SMI-27-A11, OSM-SMI-27-B0, OSM-SMI-27-B1, OSM-SMI-27-B2, OSM-SMI-27-B3, OSM-SMI-27-B4, OSM-SMI-27-B5, OSM-SMI-27-B6, OSM-SMI-27-B7, OSM-SMI-27-B8, OSM-SMI-27-B9, OSM-SMI-27-B10, OSM-SMI-27-B11, OSM-SMI-27-C0, OSM-SMI-27-C1, OSM-SMI-27-C2, OSM-SMI-27-C3, OSM-SMI-27-C4, OSM-SMI-27-C5, OSM-SMI-27-C6, OSM-SMI-27-C7, OSM-SMI-27-C8, OSM-SMI-27-C9, OSM-SMI-27-C10, OSM-SMI-27-C11, OSM-SMI-27-Z1, OSM-SMI-27-Y1, OSM-SMI-27-Y2, OSM-SMI-27-X1, OSM-SMI-27-X2, OSM-SMI-27-X3, OSM-SMI-27-X4, OSM-SMI-27-W1, OSM-SMI-27-W2, OSM-SMI-27-W3, OSM-SMI-27-W4, OSM-SMI-27-W5, OSM-SMI-27-W6, OSM-SMI-27-V1, OSM-SMI-27-V2, OSM-SMI-27-V3, OSM-SMI-27-V4, OSM-SMI-27-V5, OSM-SMI-27-V6, OSM-SMI-27-U1, OSM-SMI-27-U2, OSM-SMI-27-U3, OSM-SMI-27-U4, OSM-SMI-27-T1, OSM-SMI-27-T2, and/or OSM-SMI-27-T3.

2. The method of claim 1, wherein the OSM antagonist inhibits or reduces the spread of a primary tumor to a pre-metastatic organ of the subject.

3. The method of claim 1, wherein reducing tumor cell detachment, progression, proliferation and/or metastasis comprises reducing size or number of lung metastases.

4. The method of claim 1, wherein inhibiting or reducing tumor cell detachment, progression, proliferation and/or metastasis comprises reducing one or more expression levels of OSM, gp130, LIFRα subunit or OSMRβ, in a pre-metastatic organ of the subject.

5. The method of claim 1, wherein inhibiting or reducing tumor cell detachment, progression, proliferation, and/or metastasis comprises reducing expression levels of OSM in a pre-metastatic organ of the subject.

6. The method of claim 1 further comprising administering to the subject an effective amount of gp-130 antagonist.

7. The method of claim 1 wherein said small molecule is one or more or OSM-SMI-8A, OSM-SMI-8B, OSM-SMI-8C, OSM-SMI-8D, OSM-SMI-8E, OSM-SMI-8F, OSM-SMI-8G, OSM-SMI-8H, OSM-SMI-8I, OSM-SMI-8J, and/or OSM-SMI-8N1.

8. The method of claim 1 wherein said small molecule is one or more of OSM-SMI-10A, OSM-SMI-10B, OSM-SMI-10C, OSM-SMI-10D, OSM-SMI-10E, OSM-SMI-10F, OSM-SMI-10G, OSM-SMI-10H, OSM-SMI-10I, OSM-SMI-10J, OSM-SMI-10K, OSM-SMI-10L, OSM-SMI-10M, OSM-SMI-10N, OSM-SMI-10O, OSM-SMI-10P, OSM-SMI-10Q, OSM-SMI-10R, and/or OSM-SMI-10S.

9. The method of claim 1, wherein said small molecule is OSM-SMI-10B-1, OSM-SMI-10B-2, OSM-SMI-10B-3, OSM-SMI-10B-4, OSM-SMI-10B-5, OSM-SMI-10B-6, OSM-SMI-10B-7, OSM-SMI-10B-8, OSM-SMI-10B-9, OSM-SMI-10B-10, OSM-SMI-10B-11, OSM-SMI-10B-12, OSM-SMI-10B-13, OSM-SMI-10B-14, OSM-SMI-10B-15, OSM-SMI-10B-16, OSM-SMI-10B-17, OSM-SMI-10B-18, OSM-SMI-10B-19, OSM-SMI-10B-20, OSM-SMI-10B-21, OSM-SMI-10B-22, OSM-SMI-10B-23, OSM-SMI-10B-24, OSM-SMI-10B-25, OSM-SMI-10B-26, OSM-SMI-10B-27, OSM-SMI-10B-28, OSM-SMI-10B-29, OSM-SMI-10B-30, OSM-SMI-10B-31, OSM-SMI-10B-32, OSM-SMI-10B-33, OSM-SMI-10B-34, OSM-SMI-10B-35, OSM-SMI-10B-36, and/or OSM-SMI-10B-37.

10. The method of claim 1, wherein said small molecule is one or more of OSM-SMI-23, OSM-SMI-23A, OSM-SMI-23B, OSM-SMI-23C, OSM-SMI-23D, OSM-SMI-23E, OSM-SMI-23F, OSM-SMI-23G, OSM-SMI-23H, OSM-SMI-23I, OSM-SMI-23J, OSM-SMI-23K, OSM-SMI-23L, OSM-SMI-23M, OSM-SMI-23N, OSM-SMI-23O, OSM-SMI-23P, and/or OSM-SMI-23R.

11. The method of claim 1, wherein said small molecule is one or more of OSM-SMI-26, OSM-SMI-26A, OSM-SMI-26B, OSM-SMI-26C, OSM-SMI-26D, OSM-SMI-26E, OSM-SMI-26F, OSM-SMI-26G, OSM-SMI-26H, OSM-SMI-26I, OSM-SMI-26J, OSM-SMI-26K, OSM-SMI-26L, OSM-SMI-26M, OSM-SMI-26N, OSM-SMI-26O, OSM-SMI-26P, and/or OSM-SMI-26Q.

12. The method of claim 1, wherein said small molecule is one or more of OSM-SMI-27, OSM-SMI-27-A1, OSM-SMI-27-A2, OSM-SMI-27-A3, OSM-SMI-27-A4, OSM-SMI-27-A5, OSM-SMI-27-A6, OSM-SMI-27-A7, OSM-SMI-27-A8, OSM-SMI-27-A9, OSM-SMI-27-A10, OSM-SMI-27-A11, OSM-SMI-27-B0, OSM-SMI-27-B1, OSM-SMI-27-B2, OSM-SMI-27-B3, OSM-SMI-27-B4, OSM-SMI-27-B5, OSM-SMI-27-B6, OSM-SMI-27-B7, OSM-SMI-27-B8, OSM-SMI-27-B9, OSM-SMI-27-B10, OSM-SMI-27-B11, OSM-SMI-27-C0, OSM-SMI-27-C1, OSM-SMI-27-C2, OSM-SMI-27-C3, OSM-SMI-27-C4, OSM-SMI-27-C5, OSM-SMI-27-C6, OSM-SMI-27-C7, OSM-SMI-27-C8, OSM-SMI-27-C9, OSM-SMI-27-C10, OSM-SMI-27-C11, OSM-SMI-27-Z1, OSM-SMI-27-Y1, OSM-SMI-27-Y2, OSM-SMI-27-X1, OSM-SMI-27-X2, OSM-SMI-27-X3, OSM-SMI-27-X4, OSM-SMI-27-W1, OSM-SMI-27-W2, OSM-SMI-27-W3, OSM-SMI-27-W4, OSM-SMI-27-W5, OSM-SMI-27-W6, OSM-SMI-27-V1, OSM-SMI-27-V2, OSM-SMI-27-V3, OSM-SMI-27-V4, OSM-SMI-27-V5, OSM-SMI-27-V6, OSM-SMI-27-U1, OSM-SMI-27-U2, OSM-SMI-27-U3, OSM-SMI-27-U4, OSM-SMI-27-T1, OSM-SMI-27-T2, and/or OSM-SMI-27-T3.

13. A method of inhibiting migration of metastatic tumor cells or neutrophils to a pre-metastatic organ comprising administering to the subject an effective amount of an OSM or OSM receptor (gp-130) antagonist of claim 1.

14. The method of claim 13, wherein the pre-metastatic organ is lung or liver.

15. The method of claim 13 wherein said small molecule is OSM-SMI-8N1.

16. The method of claim 13 further comprising administering to the subject an effective amount of a chemotherapeutic agent.

17. The method of claim 13, wherein the subject is human.

18. A pharmaceutical composition comprising a unit dose of at least 1 mg of a small molecule antagonist to oncostatin M (OSM), wherein the small molecule antagonist of oncostatin M is selected from the group consisting of OSM-SMI-8A, OSM-SMI-8B, OSM-SMI-8C, OSM-SMI-8D, OSM-SMI-8E, OSM-SMI-8F, OSM-SMI-8G, OSM-SMI-8H, OSM-SMI-8I, OSM-SMI-8J, OSM-SMI-8N1, OSM-SMI-10A, OSM-SMI-10B, OSM-SMI-10B-2, OSM-SMI-10B-3, OSM-SMI-10B-4, OSM-SMI-10B-5, OSM-SMI-10B-6, OSM-SMI-10B-7, OSM-SMI-10B-8, OSM-SMI-10B-9, OSM-SMI-10B-10, OSM-SMI-10B-11, OSM-SMI-10B-12, OSM-SMI-10B-13, OSM-SMI-10B-14, OSM-SMI-10B-15, OSM-SMI-10B-16, OSM-SMI-10B-17, OSM-SMI-10B-18, OSM-SMI-10B-19, OSM-SMI-10B-20, OSM-SMI-10B-21, OSM-SMI-10B-22, OSM-SMI-10B-23, OSM-SMI-10B-24, OSM-SMI-10B-25, OSM-SMI-10B-26, OSM-SMI-10B-27, OSM-SMI-10B-28, OSM-SMI-10B-29, OSM-SMI-10B-30, OSM-SMI-10B-31, OSM-SMI-10B-32, OSM-SMI-10B-33, OSM-SMI-10B-34, OSM-SMI-10B-35, OSM-SMI-10B-36, OSM-SMI-10B-37, OSM-SMI-10C, OSM-SMI-10D, OSM-SMI-10E, OSM-SMI-10F, OSM-SMI-10G, OSM-SMI-10H, OSM-SMI-10I, OSM-SMI-10J, OSM-SMI-10K, OSM-SMI-10L, OSM-SMI-10M, OSM-SMI-10N, OSM-SMI-10O, OSM-SMI-10P, OSM-SMI-10Q, OSM-SMI-10R, OSM-SMI-10S, OSM-SMI-23, OSM-SMI-23A, OSM-SMI-23B, OSM-SMI-23C, OSM-SMI-23D, OSM-SMI-23E, OSM-SMI-23F, OSM-SMI-23G, OSM-SMI-23H, OSM-SMI-23I, OSM-SMI-23J, OSM-SMI-23K, OSM-SMI-23L, OSM-SMI-23M, OSM-SMI-23N, OSM-SMI-23O, OSM-SMI-23P, OSM-SMI-23Q, OSM-SMI-23R, OSM-SMI-26, OSM-SMI-26A, OSM-SMI-26B, OSM-SMI-26C, OSM-SMI-26D, OSM-SMI-26E, OSM-SMI-26F, OSM-SMI-26G, OSM-SMI-26H, OSM-SMI-26I, OSM-SMI-26J, OSM-SMI-26K, OSM-SMI-26L, OSM-SMI-26M, OSM-SMI-26N, OSM-SMI-26O, OSM-SMI-26P, OSM-SMI-26Q, OSM-SMI-27, OSM-SMI-27-A1, OSM-SMI-27-A2, OSM-SMI-27-A3, OSM-SMI-27-A4, OSM-SMI-27-A5, OSM-SMI-27-A6, OSM-SMI-27-A7, OSM-SMI-27-A8, OSM-SMI-27-A9, OSM-SMI-27-A10, OSM-SMI-27-A11, OSM-SMI-27-B0, OSM-SMI-27-B1, OSM-SMI-27-B2, OSM-SMI-27-B3, OSM-SMI-27-B4, OSM-SMI-27-B5, OSM-SMI-27-B6, OSM-SMI-27-B7, OSM-SMI-27-B8, OSM-SMI-27-B9, OSM-SMI-27-B10, OSM-SMI-27-B11, OSM-SMI-27-CO, OSM-SMI-27-C1, OSM-SMI-27-C2, OSM-SMI-27-C3, OSM-SMI-27-C4, OSM-SMI-27-C5, OSM-SMI-27-C6, OSM-SMI-27-C7, OSM-SMI-27-C8, OSM-SMI-27-C9, OSM-SMI-27-C10, OSM-SMI-27-C11, OSM-SMI-27-Z1, OSM-SMI-27-Y 1, OSM-SMI-27-Y2, OSM-SMI-27-X1, OSM-SMI-27-X2, OSM-SMI-27-X3, OSM-SMI-27-X4, OSM-SMI-27-W1, OSM-SMI-27-W2, OSM-SMI-27-W3, OSM-SMI-27-W4, OSM-SMI-27-W5, OSM-SMI-27-W6, OSM-SMI-27-V1, OSM-SMI-27-V2, OSM-SMI-27-V3, OSM-SMI-27-V4, OSM-SMI-27-V5, OSM-SMI-27-V6, OSM-SMI-27-U1, OSM-SMI-27-U2, OSM-SMI-27-U3, OSM-SMI-27-U4, OSM-SMI-27-T1, OSM-SMI-27-T2 and a pharmaceutically acceptable carrier.

19. The pharmaceutical composition according to claim 18 wherein the antagonist is combined with a chemotherapy agent.

20. The pharmaceutical composition of claim 18 wherein said small molecule is OSM-SMI-8N1.

21. The pharmaceutical composition of claim 18, wherein said small molecule is one or more of OSM-SMI-10A, OSM-SMI-10B, OSM-SMI-10C, OSM-SMI-10D, OSM-SMI-10E, OSM-SMI-10F, OSM-SMI-10G, OSM-SMI-10H, OSM-SMI-10I, OSM-SMI-10J, OSM-SMI-10K, OSM-SMI-10L, OSM-SMI-10M, OSM-SMI-10N, OSM-SMI-10O, OSM-SMI-10P, OSM-SMI-10Q, OSM-SMI-10R, and/or OSM-SMI-10S.

22. The pharmaceutical composition of claim 21, wherein said small molecule is OSM-SMI-10B.

23. The pharmaceutical composition of claim 18, wherein said small molecule is one or more of OSM-SMI-23, OSM-SMI-23A, OSM-SMI-23B, OSM-SMI-23C, OSM-SMI-23D, OSM-SMI-23E, OSM-SMI-23F, OSM-SMI-23G, OSM-SMI-23H, OSM-SMI-23I, OSM-SMI-23J, OSM-SMI-23K, OSM-SMI-23L, OSM-SMI-23M, OSM-SMI-23N, OSM-SMI-23O, OSM-SMI-23P, and/or OSM-SMI-23R.

24. The pharmaceutical composition of claim 18, wherein said small molecule is one or more of OSM-SMI-26, OSM-SMI-26A, OSM-SMI-26B, OSM-SMI-26C, OSM-SMI-26D, OSM-SMI-26E, OSM-SMI-26F, OSM-SMI-26G, OSM-SMI-26H, OSM-SMI-26I, OSM-SMI-26J, OSM-SMI-26K, OSM-SMI-26L, OSM-SMI-26M, OSM-SMI-26N, OSM-SMI-26O, OSM-SMI-26P, and/or OSM-SMI-26Q.

25. The pharmaceutical composition of claim 18, wherein said small molecule is one or more of OSM-SMI-27, OSM- SMI-27-A1, OSM-SMI-27-A2, OSM-SMI-27-A3, OSM-SMI-27-A4, OSM-SMI-27-A5, OSM-SMI-27-A6, OSM-SMI-27-A7, OSM-SMI-27-A8, OSM-SMI-27-A9, OSM-SMI-27-A10, OSM-SMI-27-A11, OSM-SMI-27-B0, OSM-SMI-27-B1, OSM-SMI-27-B2, OSM-SMI-27-B3, OSM-SMI-27-B4, OSM-SMI-27-B5, OSM-SMI-27-B6, OSM-SMI-27-B7, OSM-SMI-27-B8, OSM-SMI-27-B9, OSM-SMI-27-B10, OSM-SMI-27-B11, OSM-SMI-27-C0, OSM-SMI-27-C1, OSM-SMI-27-C2, OSM-SMI-27-C3, OSM-SMI-27-C4, OSM-SMI-27-C5, OSM-SMI-27-C6, OSM-SMI-27-C7, OSM-SMI-27-C8, OSM-SMI-27-C9, OSM-SMI-27-C10, OSM-SMI-27-C11, OSM-SMI-27-Z1, OSM-SMI-27-Y1, OSM-SMI-27-Y2, OSM-SMI-27-X1, OSM-SMI-27-X2, OSM-SMI-27-X3, OSM-SMI-27-X4, OSM-SMI-27-W1, OSM-SMI-27-W2, OSM-SMI-27-W3, OSM-SMI-27-W4, OSM-SMI-27-W5, OSM-SMI-27-W6, OSM-SMI-27-V1, OSM-SMI-27-V2, OSM-SMI-27-V3, OSM-SMI-27-V4, OSM-SMI-27-V5, OSM-SMI-27-V6, OSM-SMI-27-U1, OSM-SMI-27-U2, OSM-SMI-27-U3, OSM-SMI-27-U4, OSM-SMI-27-T1, OSM-SMI-27-T2, and/or OSM-SMI-27-T3.

26. The pharmaceutical composition of claim 18, wherein said composition is effective for inhibiting or reducing the spread of a primary tumor to a pre-metastatic organ of the subject.

27. The pharmaceutical composition of claim 18, wherein the antagonist is combined with an effective amount of gp-130 antagonist.

28. The pharmaceutical composition of claim 18, wherein the OSM antagonist is combined with a chemotherapy agent, an immune modulator or an anti-OSM antibody or a fragment thereof.

29. The pharmaceutical composition of claim 18, wherein said composition is effective for reducing tumor cell detachment, progression, proliferation and/or metastasis, wherein reducing tumor cell detachment, progression, proliferation and/or metastasis comprises reducing size or number of lung metastases.

30. A pharmaceutical composition for use in inhibiting or reducing tumor cell detachment, proliferation and/or metastasis, comprising an effective amount of an antagonist to OSM, wherein the OSM antagonist is one or more of OSM-SMI-8A, OSM-SMI-8B, OSM-SMI-8C, OSM-SMI-8D, OSM-SMI-8E, OSM-SMI-8F, OSM-SMI-8G, OSM-SMI-8H, OSM-SMI-8I, OSM-SMI-8J, OSM-SMI-8N1, OSM-SMI-10A, OSM-SMI-10B, OSM-SMI-10B-2, OSM-SMI-10B-3, OSM-SMI-10B-4, OSM-SMI-10B-5, OSM-SMI-10B-6, OSM-SMI-10B-7, OSM-SMI-10B-8, OSM-SMI-10B-9, OSM-SMI-10B-10, OSM-SMI-10B-11, OSM-SMI-10B-12, OSM-SMI-10B-13, OSM-SMI-10B-14, OSM-SMI-10B-15, OSM-SMI-10B-16, OSM-SMI-10B-17, OSM-SMI-10B-18, OSM-SMI-10B-19, OSM-SMI-10B-20, OSM-SMI-10B-21, OSM-SMI-10B-22, OSM-SMI-10B-23, OSM-SMI-10B-24, OSM-SMI-10B-25, OSM-SMI-10B-26, OSM-SMI-10B-27, OSM-SMI-10B-28, OSM-SMI-10B-29, OSM-SMI-10B-30, OSM-SMI-10B-31, OSM-SMI-10B-32, OSM-SMI-10B-33, OSM-SMI-10B-34, OSM-SMI-10B-35, OSM-SMI-10B-36, OSM-SMI-10B-37, OSM-SMI-10C, OSM-SMI-10D, OSM-SMI-10E, OSM-SMI-10F, OSM-SMI-10G, OSM-SMI-10H, OSM-SMI-10I, OSM-SMI-10J, OSM-SMI-10K, OSM-SMI-10L, OSM-SMI-10M, OSM-SMI-10N, OSM-SMI-10O, OSM-SMI-10P, OSM-SMI-10Q, OSM-SMI-10R, OSM-SMI-10S, OSM-SMI-23, OSM-SMI-23A, OSM-SMI-23B, OSM-SMI-23C, OSM-SMI-23D, OSM-SMI-23E, OSM-SMI-23F, OSM-SMI-23G, OSM-SMI-23H, OSM-SMI-23I, OSM-SMI-23J, OSM-SMI-23K, OSM-SMI-23L, OSM-SMI-23M, OSM-SMI-23N, OSM-SMI-23O, OSM-SMI-23P, OSM-SMI-23R, OSM-SMI-26, OSM-SMI-26A, OSM-SMI-26B, OSM-SMI-26C, OSM-SMI-26D, OSM-SMI-26E, OSM-SMI-26F, OSM-SMI-26G, OSM-SMI-26H, OSM-SMI-26I, OSM-SMI-26J, OSM-SMI-26K, OSM-SMI-26L, OSM-SMI-26M, OSM-SMI-26N, OSM-SMI-26O, OSM-SMI-26P, OSM-SMI-26Q, OSM-SMI-27, OSM-SMI-27-A1, OSM-SMI-27-A2, OSM-SMI-27-A3, OSM-SMI-27-A4, OSM-SMI-27-A5, OSM-SMI-27-A6, OSM-SMI-27-A7, OSM-SMI-27-A8, OSM-SMI-27-A9, OSM-SMI-27-A10, OSM-SMI-27-A11, OSM-SMI-27-B0, OSM-SMI-27-B1, OSM-SMI-27-B2, OSM-SMI-27-B3, OSM-SMI-27-B4, OSM-SMI-27-B5, OSM-SMI-27-B6, OSM-SMI-27-B7, OSM-SMI-27-B8, OSM-SMI-27-B9, OSM-SMI-27-B10, OSM-SMI-27-B11, OSM-SMI-27-C0, OSM-SMI-27-C1, OSM-SMI-27-C2, OSM-SMI-27-C3, OSM-SMI-27-C4, OSM-SMI-27-C5, OSM-SMI-27-C6, OSM-SMI-27-C7, OSM-SMI-27-C8, OSM-SMI-27-C9, OSM-SMI-27-C10, OSM-SMI-27-C11, OSM-SMI-27-Z1, OSM-SMI-27-Y1, OSM-SMI-27-Y2, OSM-SMI-27-X1, OSM-SMI-27-X2, OSM-SMI-27-X3, OSM-SMI-27-X4, OSM-SMI-27-W1, OSM-SMI-27-W2, OSM-SMI-27-W3, OSM-SMI-27-W4, OSM-SMI-27-W5, OSM-SMI-27-W6, OSM-SMI-27-V1, OSM-SMI-27-V2, OSM-SMI-27-V3, OSM-SMI-27-V4, OSM-SMI-27-V5, OSM-SMI-27-V6, OSM-SMI-27-U1, OSM-SMI-27-U2, OSM-SMI-27-U3, OSM-SMI-27-U4, OSM-SMI-27-T1, OSM-SMI-27-T2, and/or OSM-SMI-27-T3; and a pharmaceutically acceptable carrier.

31. A small molecule antagonist to oncostatin M (OSM), comprising OSM-SMI-8A, OSM-SMI-8B, OSM-SMI-8C, OSM-SMI-8D, OSM-SMI-8E, OSM-SMI-8F, OSM-SMI-8G, OSM-SMI-8H, OSM-SMI-8I, OSM-SMI-8J, OSM-SMI-8N1, OSM-SMI-10A, OSM-SMI-10B, OSM-SMI-10B-2, OSM-SMI-10B-3, OSM-SMI-10B-4, OSM-SMI-10B-5, OSM-SMI-10B-6, OSM-SMI-10B-7, OSM-SMI-10B-8, OSM-SMI-10B-9, OSM-SMI-10B-10, OSM-SMI-10B-11, OSM-SMI-10B-12, OSM-SMI-10B-13, OSM-SMI-10B-14, OSM-SMI-10B-15, OSM-SMI-10B-16, OSM-SMI-10B-17, OSM-SMI-10B-18, OSM-SMI-10B-19, OSM-SMI-10B-20, OSM-SMI-10B-21, OSM-SMI-10B-22, OSM-SMI-10B-23, OSM-SMI-10B-24, OSM-SMI-10B-25, OSM-SMI-10B-26, OSM-SMI-10B-27, OSM-SMI-10B-28, OSM-SMI-10B-29, OSM-SMI-10B-30, OSM-SMI-10B-31, OSM-SMI-10B-32, OSM-SMI-10B-33, OSM-SMI-10B-34, OSM-SMI-10B-35, OSM-SMI-10B-36, OSM-SMI-10B-37, OSM-SMI-10C, OSM-SMI-10D, OSM-SMI-10E, OSM-SMI-10F, OSM-SMI-10G, OSM-SMI-10H, OSM-SMI-10I, OSM-SMI-10J, OSM-SMI-10K, OSM-SMI-10L, OSM-SMI-10M, OSM-SMI-10N, OSM-SMI-10O, OSM-SMI-10P, OSM-SMI-10Q, OSM-SMI-10R, OSM-SMI-10S, OSM-SMI-23, OSM-SMI-23A, OSM-SMI-23B, OSM-SMI-23C, OSM-SMI-23D, OSM-SMI-23E, OSM-SMI-23F, OSM-SMI-23G, OSM-SMI-23H, OSM-SMI-23I, OSM-SMI-23J, OSM-SMI-23K, OSM-SMI-23L, OSM-SMI-23M, OSM-SMI-23N, OSM-SMI-23O, OSM-SMI-23P, OSM-SMI-23R, OSM-SMI-26, OSM-SMI-26A, OSM-SMI-26B, OSM-SMI-26C, OSM-SMI-26D, OSM-SMI-26E, OSM-SMI-26F, OSM-SMI-26G, OSM-SMI-26H, OSM-SMI-26I, OSM-SMI-26J, OSM-SMI-26K, OSM-SMI-26L, OSM-SMI-26M, OSM-SMI-26N, OSM-SMI-26O, OSM-SMI-26P, OSM-SMI-26Q, OSM-SMI-27, OSM-SMI-27-A1, OSM-SMI-27-A2, OSM-SMI-27-A3, OSM-SMI-27-A4, OSM-SMI-27-A5, OSM-SMI-27-A6, OSM-SMI-27-A7, OSM-SMI-27-A8, OSM-SMI-27-A9, OSM-SMI-27-A10, OSM-SMI-27-A11, OSM-SMI-27-B0, OSM-SMI-27-B1, OSM-SMI-27-B2, OSM-SMI-27-B3, OSM-SMI-27-B4, OSM-SMI-27-B5, OSM-SMI-27-B6, OSM-SMI-27-B7, OSM-SMI-27-B8, OSM-SMI-27-B9, OSM-SMI-27-B10, OSM-SMI-27-B11, OSM-SMI-27-C0, OSM-SMI-27-C1, OSM-SMI-27-C2, OSM-SMI-27-C3, OSM-SMI-27-C4, OSM-SMI-27-C5, OSM-SMI-27-C6, OSM-SMI-27-C7, OSM-SMI-27-C8, OSM-SMI-27-C9, OSM-SMI-27-C10, OSM-SMI-27-C11, OSM-SMI-27-Z1, OSM-SMI-27-Y1, OSM-SMI-27-Y2, OSM-SMI-27-X1, OSM-SMI-27-X2, OSM-SMI-27-X3, OSM-SMI-27-X4, OSM-SMI-27-W1, OSM-SMI-27-W2, OSM-SMI-27-W3, OSM-SMI-27-W4, OSM-SMI-27-W5, OSM-SMI-27-W6, OSM-SMI-27-V1, OSM-SMI-27-V2, OSM-SMI-27-V3, OSM-SMI-27-V4, OSM-SMI-27-V5, OSM-SMI-27-V6, OSM-SMI-27-U1, OSM-SMI-27-U2, OSM-SMI-27-U3, OSM-SMI-27-U4, OSM-SMI-27-T1, OSM-SMI-27-T2, and/or OSM-SMI-27-T3.

* * * * *

SEQUENCE LISTING

```
<160> NUMBER OF SEQ ID NOS: 2

<210> SEQ ID NO 1
<211> LENGTH: 252
<212> TYPE: PRT
<213> ORGANISM: Homo sapiens

<400> SEQUENCE: 1

Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
            20                  25                  30

Lys Glu Tyr Arg Val Leu Leu Gly Gln Leu Gln Lys Gln Thr Asp Leu
        35                  40                  45

Met Gln Asp Thr Ser Arg Leu Leu Asp Pro Tyr Ile Arg Ile Gln Gly
    50                  55                  60

Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
            100                 105                 110

Leu Glu Gln Arg Leu Pro Lys Ala Gln Asp Leu Glu Arg Ser Gly Leu
        115                 120                 125

Asn Ile Glu Asp Leu Glu Lys Leu Gln Met Ala Arg Pro Asn Ile Leu
    130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
                165                 170                 175
```

```
         Thr Pro Thr Pro Ala Ser Asp Ala Phe Gln Arg Lys Leu Glu Gly Cys
                     180                 185                 190

Arg Phe Leu His Gly Tyr His Arg Phe Met His Ser Val Gly Arg Val
                 195                 200                 205

Phe Ser Lys Trp Gly Glu Ser Pro Asn Arg Ser Arg His Ser Pro
             210                 215                 220

His Gln Ala Leu Arg Lys Gly Val Arg Arg Thr Arg Pro Ser Arg Lys
         225                 230                 235                 240

Gly Lys Arg Leu Met Thr Arg Gly Gln Leu Pro Arg
                         245                 250

<210> SEQ ID NO 2
<211> LENGTH: 1869
<212> TYPE: DNA
<213> ORGANISM: Homo sapiens

<400> SEQUENCE: 2 gtcacccca  gcgggcgcgg  gccggagcac  gggcacccag  catgggggta  ctgctcacac      60
agaggacgct  gctcagtctg  gtccttgcac  tcctgtttcc  aagcatggcg  agcatggcgg     120
ctataggcag  ctgctcgaaa  gagtaccgcg  tgctccttgg  ccagctccag  aagcagacag     180
atctcatgca  ggacaccagc  agactcctgg  accctatat   acgtatccaa  ggcctggatg     240
ttcctaaact  gagagagcac  tgcagggagc  gccccgggc   cttccccagt  gaggagaccc     300 tgaggggct   gggcaggcgg  ggcttcctgc  agaccctcaa  tgccacactg  gctgcgtcc     360 tgcacagact  ggccgactta  gagcagcgcc  tccccaaggc  ccaggatttg  agaggtctg     420 ggctgaacat  cgaggacttg  gagaagctgc  agatggcgag  gccgaacatc  ctcgggctca     480 ggaacaaat   ctactgcatg  gcccagctgc  tggacaactc  agacacggct  gagcccacga     540
aggctggccg  gggggcctct  cagccgccca  ccccacccc   tgcctcggat  gcttttcagc     600
gcaagctgga  gggctgcagg  ttcctgcatg  gctaccatcg  cttcatgcac  tcagtggggc     660
gggtcttcag  caagtggggg  gagagcccga  accggagccg  gagacacagc  ccccaccagg     720
ccctgaggaa  gggggtgcgc  aggaccagac  cctccaggaa  aggcaagaga  ctcatgacca     780
ggggacagct  gccccggtag  cctcgagagc  accccttgcc  ggtgaaggat  gcggcaggtg     840
ctctgtggat  gagaggaacc  atcgcaggat  gacagctccc  gggtccccaa  acctgttccc     900
ctctgctact  agccactgag  aagtgcactt  taagaggtgg  gagctgggca  gacccctcta     960
cctcctccag  gctgggagac  agagtcaggc  tgttgcgctc  ccacctcagc  ccaagttcc    1020 ccaggcccag  tggggtggcc  gggcgggcca  cgcgggaccg  actttccatt  gattcagggg    1080
tctgatgaca  caggctgact  catggccggg  ctgactgccc  cctgccttg   ctccccgagg    1140 cctgccggtc  cttccctctc  atgacttgca  gggccgttgc  cccagacttc  ctccttccc    1200 gtgtttctga  agggagtc   acagcctgag  ctggcctcct  atgcctcatc  atgtcccaaa    1260
ccagacacct  ggatgtctgg  gtgacctcac  tttaggcagc  tgtaacagcg  gcagggtgtc    1320
ccaggagccc  tgatccgggg  gtccagggaa  tggagctcag  gtcccaggcc  agccccgaag    1380
tcgccacgtg  gcctggggca  ggtcacttta  cctctgtgga  cctgttttct  ctttgtgaag    1440
ctagggagtt  agaggctgta  caaggccccc  actgcctgtc  ggttgcttgg  attccctgac    1500
gtaaggtgga  tattaaaaat  ctgtaaatca  ggacaggtgg  tgcaaatggc  gctgggaggt    1560
gtacacggag  gtctctgtaa  aagcagaccc  acctcccagc  gccgggaagc  ccgtcttggg    1620
tcctcgctgc  tggctgctcc  ccctggtggt  ggatcctgga  attttctcac  gcaggagcca    1680
```

```
ttgctctcct agaggggtc tcagaaactg cgaggccagt tccttggagg gacatgacta    1740
atttatcgat ttttatcaat ttttatcagt tttatattta taagccttat ttatgatgta    1800
tatttaatgt taatattgtg caaacttata tttaaaactt gcctggtttc taaaaaaaaa    1860
aaaaaaaaa                                                             1869
```